United States Patent
Schwarz et al.

(10) Patent No.: US 11,602,629 B2
(45) Date of Patent: Mar. 14, 2023

(54) SYSTEMS AND METHODS FOR TREATMENT OF A PATIENT INCLUDING RF AND ELECTRICAL ENERGY

(71) Applicant: BTL Healthcare Technologies A.S., Prague (CZ)

(72) Inventors: Tomás Schwarz, Prague (CZ); Ondrej Prouza, Ricany u Prahy (CZ)

(73) Assignee: BTL Healthcare Technologies A.S., Prague (CZ)

( * ) Notice: Subject to any disclaimer, the term of this patent is extended or adjusted under 35 U.S.C. 154(b) by 0 days.

(21) Appl. No.: 17/671,273

(22) Filed: Feb. 14, 2022

(65) Prior Publication Data

US 2022/0211997 A1 Jul. 7, 2022

Related U.S. Application Data

(63) Continuation of application No. 17/098,638, filed on Nov. 16, 2020, now Pat. No. 11,247,039, and a
(Continued)

(51) Int. Cl.
*A61N 1/04* (2006.01)
*A61N 7/02* (2006.01)
(Continued)

(52) U.S. Cl.
CPC ......... *A61N 1/0452* (2013.01); *A61N 1/0492* (2013.01); *A61N 1/36034* (2017.08);
(Continued)

(58) Field of Classification Search
CPC .............. A61N 1/0452; A61N 1/36034; A61N 1/0492; A61N 5/025
See application file for complete search history.

(56) References Cited

U.S. PATENT DOCUMENTS

| 1,973,387 A | 9/1934 | Neymann et al. |
| 2,021,676 A | 11/1935 | Wood et al. |
| (Continued) | | |

FOREIGN PATENT DOCUMENTS

| AU | 747678 B2 | 5/2002 |
| AU | 2011265424 B2 | 7/2014 |
| (Continued) | | |

OTHER PUBLICATIONS

Jalinous, R., "Technical and Practical Aspects of Magnetic Nerve Stimulation," Journal of Clinical Neurophysiology 8(1):10-25, Lippincott Williams & Wilkins, United States (Jan. 1991).
(Continued)

*Primary Examiner* — Kaitlyn E Smith
(74) *Attorney, Agent, or Firm* — Sterne, Kessler, Goldstein & Fox P.L.L.C.

(57) ABSTRACT

Systems and methods for a soft tissue treatment of a patient are provided herein. The device for a soft tissue treatment may include an applicator having at least one electrode, a fastening mechanism to fix the applicator to a body part of the patient, and a control unit having a microprocessor to control the at least one electrode. The at least one electrode may provide radiofrequency energy and pulsed electric current. The radiofrequency energy may cause a heating of a soft tissue. The electric current may cause contraction of a muscle within the body part. The body part may be a face.

24 Claims, 21 Drawing Sheets

Related U.S. Application Data continuation-in-part of application No. 16/194,800, filed on Nov. 19, 2018, now Pat. No. 11,464,993, and a continuation-in-part of application No. 15/584,747, filed on May 2, 2017, now Pat. No. 10,195,453.

(60) Provisional application No. 63/019,619, filed on May 4, 2020, provisional application No. 62/587,716, filed on Nov. 17, 2017, provisional application No. 62/375,796, filed on Aug. 16, 2016, provisional application No. 62/358,417, filed on Jul. 5, 2016, provisional application No. 62/351,156, filed on Jun. 16, 2016, provisional application No. 62/340,398, filed on May 23, 2016, provisional application No. 62/333,666, filed on May 9, 2016, provisional application No. 62/331,088, filed on May 3, 2016, provisional application No. 62/331,060, filed on May 3, 2016, provisional application No. 62/331,072, filed on May 3, 2016.

(51) Int. Cl.
  *A61N 1/36* (2006.01)
  *A61N 7/00* (2006.01)

(52) U.S. Cl.
  CPC ........ *A61N 7/02* (2013.01); *A61N 2007/0034* (2013.01); *A61N 2007/0073* (2013.01)

(56) References Cited

U.S. PATENT DOCUMENTS

| | | |
|---|---|---|
| 3,163,161 A | 12/1964 | Jacques et al. |
| 3,566,877 A | 3/1971 | Smith et al. |
| 3,658,051 A | 4/1972 | Maclean et al. |
| 3,841,306 A | 10/1974 | Hallgren et al. |
| 3,915,151 A | 10/1975 | Kraus |
| 3,946,349 A | 3/1976 | Haldeman, III |
| 3,952,751 A | 4/1976 | Yarger |
| 3,971,387 A | 7/1976 | Mantell |
| 4,068,292 A | 1/1978 | Berry et al. |
| 4,143,661 A | 3/1979 | LaFORGE et al. |
| 4,197,851 A | 4/1980 | Fellus |
| 4,237,898 A | 12/1980 | Whalley |
| 4,305,115 A | 12/1981 | Armitage |
| 4,315,503 A | 2/1982 | Ryaby et al. |
| 4,392,040 A | 7/1983 | Rand et al. |
| 4,454,883 A | 6/1984 | Fellus |
| 4,456,001 A | 6/1984 | Pescatore |
| 4,550,714 A | 11/1985 | Talish et al. |
| 4,556,056 A | 12/1985 | Fischer et al. |
| 4,665,898 A | 5/1987 | Costa et al. |
| 4,674,482 A | 6/1987 | Waltonen et al. |
| 4,674,505 A | 6/1987 | Pauli et al. |
| 4,723,536 A | 2/1988 | Rauscher et al. |
| 4,850,959 A | 7/1989 | Findl |
| 4,889,526 A | 12/1989 | Rauscher et al. |
| 4,957,480 A | 9/1990 | Morenings |
| 4,989,604 A | 2/1991 | Fang |
| 4,993,413 A | 2/1991 | Mcleod et al. |
| 5,061,234 A | 10/1991 | Chaney |
| 5,067,940 A | 11/1991 | Liboff et al. |
| 5,085,626 A | 2/1992 | Frey |
| 5,143,063 A | 9/1992 | Fellner |
| 5,156,587 A | 10/1992 | Montone |
| 5,181,902 A | 1/1993 | Erickson et al. |
| 5,199,951 A | 4/1993 | Spears |
| 5,334,181 A | 8/1994 | Rubinsky et al. |
| 5,344,384 A | 9/1994 | Ostrow et al. |
| 5,401,233 A | 3/1995 | Erickson et al. |
| 5,415,617 A | 5/1995 | Kraus |
| 5,419,344 A | 5/1995 | Dewitt |
| 5,433,737 A | 7/1995 | Aimone |
| 5,433,740 A | 7/1995 | Yamaguchi |
| 5,584,863 A | 12/1996 | Rauch et al. |
| 5,620,463 A | 4/1997 | Drolet |
| 5,660,836 A | 8/1997 | Knowlton |
| 5,674,218 A | 10/1997 | Rubinsky et al. |
| 5,690,692 A | 11/1997 | Fleming |
| 5,691,873 A | 11/1997 | Masaki |
| 5,718,662 A | 2/1998 | Jalinous |
| 5,725,471 A | 3/1998 | Davey et al. |
| 5,755,753 A | 5/1998 | Knowlton |
| 5,766,124 A | 6/1998 | Polson |
| 5,782,743 A | 7/1998 | Russell |
| 5,807,232 A | 9/1998 | Espinoza et al. |
| 5,857,957 A | 1/1999 | Lin |
| 5,908,444 A | 6/1999 | Azure |
| 5,919,219 A | 7/1999 | Knowlton |
| 5,968,527 A | 10/1999 | Litovitz |
| 5,984,854 A | 11/1999 | Ishikawa et al. |
| 6,017,337 A | 1/2000 | Pira |
| 6,032,675 A | 3/2000 | Rubinsky |
| 6,038,485 A | 3/2000 | Axelgaard |
| 6,047,215 A | 4/2000 | McCLURE et al. |
| 6,063,108 A | 5/2000 | Salansky et al. |
| 6,067,474 A | 5/2000 | Schulman et al. |
| 6,086,525 A | 7/2000 | Davey et al. |
| 6,094,599 A | 7/2000 | Bingham et al. |
| 6,099,459 A | 8/2000 | Jacobson |
| 6,099,523 A | 8/2000 | Kim et al. |
| 6,117,066 A | 9/2000 | Abrams et al. |
| 6,132,361 A | 10/2000 | Epstein et al. |
| 6,141,985 A | 11/2000 | Cluzeau et al. |
| 6,155,966 A | 12/2000 | Parker |
| 6,161,757 A | 12/2000 | Morris |
| 6,179,769 B1 | 1/2001 | Ishikawa et al. |
| 6,179,770 B1 | 1/2001 | Mould |
| 6,179,771 B1 | 1/2001 | Mueller |
| 6,200,259 B1 | 3/2001 | March |
| 6,213,933 B1 | 4/2001 | Lin |
| 6,223,750 B1 | 5/2001 | Ishikawa et al. |
| 6,246,905 B1 | 6/2001 | Mogul |
| 6,255,815 B1 | 7/2001 | Davey |
| 6,261,301 B1 | 7/2001 | Knesch et al. |
| 6,273,862 B1 | 8/2001 | Privitera et al. |
| 6,273,884 B1 | 8/2001 | Altshuler et al. |
| 6,280,376 B1 | 8/2001 | Holcomb |
| 6,282,448 B1 | 8/2001 | Katz et al. |
| D447,806 S | 9/2001 | Davey et al. |
| 6,311,090 B1 | 10/2001 | Knowlton |
| 6,324,430 B1 | 11/2001 | Zarinetchi et al. |
| 6,324,432 B1 | 11/2001 | Rigaux et al. |
| 6,334,069 B1 | 12/2001 | George et al. |
| 6,334,074 B1 | 12/2001 | Spertell |
| 6,350,276 B1 | 2/2002 | Knowlton |
| 6,402,678 B1 | 6/2002 | Fischell et al. |
| 6,413,255 B1 | 7/2002 | Stern |
| 6,418,345 B1 | 7/2002 | Tepper et al. |
| 6,424,864 B1 | 7/2002 | Matsuura |
| 6,425,852 B1 | 7/2002 | Epstein et al. |
| 6,443,883 B1 | 9/2002 | Ostrow et al. |
| 6,445,955 B1 | 9/2002 | Michelson et al. |
| 6,447,440 B1 | 9/2002 | Markoll |
| 6,453,202 B1 | 9/2002 | Knowlton |
| 6,461,375 B1 | 10/2002 | Baudry et al. |
| 6,491,620 B1 | 12/2002 | Davey |
| 6,500,110 B1 | 12/2002 | Davey et al. |
| 6,520,903 B1 | 2/2003 | Yamashiro |
| 6,527,694 B1 | 3/2003 | Ishikawa et al. |
| 6,527,695 B1 | 3/2003 | Davey et al. |
| 6,537,197 B1 | 3/2003 | Ruohonen et al. |
| 6,569,078 B2 | 5/2003 | Ishikawa et al. |
| 6,605,080 B1 | 8/2003 | Altshuler et al. |
| 6,635,053 B1 | 10/2003 | Lalonde et al. |
| 6,658,301 B2 | 12/2003 | Loeb et al. |
| 6,662,054 B2 | 12/2003 | Kreindel et al. |
| 6,663,556 B2 | 12/2003 | Barker |
| 6,663,659 B2 | 12/2003 | McDANIEL |
| 6,701,185 B2 | 3/2004 | Burnett et al. |
| 6,735,481 B1 | 5/2004 | Bingham et al. |
| 6,738,667 B2 | 5/2004 | Deno et al. |
| 6,749,624 B2 | 6/2004 | Knowlton |

(56) References Cited

U.S. PATENT DOCUMENTS

| | | |
|---|---|---|
| 6,827,681 B2 | 12/2004 | Tanner et al. |
| 6,849,040 B2 | 2/2005 | Ruohonen et al. |
| 6,860,852 B2 | 3/2005 | Schonenberger et al. |
| 6,871,099 B1 | 3/2005 | Whitehurst et al. |
| 6,879,859 B1 | 4/2005 | Boveja |
| 6,889,090 B2 | 5/2005 | Kreindel |
| 6,920,883 B2 | 7/2005 | Bessette et al. |
| 6,939,287 B1 | 9/2005 | Ardizzone et al. |
| 6,960,202 B2 | 11/2005 | Cluzeau et al. |
| 6,990,427 B2 | 1/2006 | Kirsch et al. |
| 7,024,239 B2 | 4/2006 | George et al. |
| 7,030,764 B2 | 4/2006 | Smith et al. |
| 7,041,100 B2 | 5/2006 | Kreindel |
| 7,083,580 B2 | 8/2006 | Bernabei |
| 7,186,209 B2 | 3/2007 | Jacobson et al. |
| 7,217,265 B2 | 5/2007 | Hennings et al. |
| 7,276,058 B2 | 10/2007 | Altshuler et al. |
| 7,309,309 B2 | 12/2007 | Wang et al. |
| 7,318,821 B2 | 1/2008 | Lalonde et al. |
| 7,351,252 B2 | 4/2008 | Altshuler et al. |
| 7,367,341 B2 | 5/2008 | Anderson et al. |
| 7,369,895 B2 | 5/2008 | Hurtado |
| 7,372,271 B2 | 5/2008 | Roozen et al. |
| 7,376,460 B2 | 5/2008 | Bernabei |
| 7,396,326 B2 | 7/2008 | Ghiron et al. |
| 7,496,401 B2 | 2/2009 | Bernabei |
| 7,520,849 B1 | 4/2009 | Simon |
| 7,520,875 B2 | 4/2009 | Bernabei |
| 7,532,926 B2 | 5/2009 | Bernabei |
| 7,571,003 B2 | 8/2009 | Pozzato |
| 7,591,776 B2 | 9/2009 | Phillips et al. |
| 7,601,115 B2 | 10/2009 | Riehl |
| 7,608,035 B2 | 10/2009 | Farone |
| 7,618,429 B2 | 11/2009 | Mulholland |
| 7,630,774 B2 | 12/2009 | Karni et al. |
| 7,643,883 B2 | 1/2010 | Kreindel |
| 7,697,998 B2 | 4/2010 | Axelgaard |
| 7,699,768 B2 | 4/2010 | Kishawi et al. |
| 7,740,574 B2 | 6/2010 | Pilla et al. |
| 7,744,523 B2 | 6/2010 | Epstein |
| 7,783,348 B2 | 8/2010 | Gill et al. |
| 7,785,358 B2 | 8/2010 | Lach |
| 7,854,754 B2 | 12/2010 | Ting et al. |
| 7,909,786 B2 | 3/2011 | Bonnefin et al. |
| 7,914,469 B2 | 3/2011 | Torbati |
| 7,945,321 B2 | 5/2011 | Bernabei |
| 7,946,973 B2 | 5/2011 | Peterchev |
| 7,953,500 B2 | 5/2011 | Bingham et al. |
| 7,998,053 B2 | 8/2011 | Aho |
| 8,035,385 B2 | 10/2011 | Tomiha et al. |
| RE43,007 E | 12/2011 | Lalonde et al. |
| 8,088,058 B2 | 1/2012 | Juliana et al. |
| 8,128,549 B2 | 3/2012 | Testani et al. |
| 8,133,191 B2 | 3/2012 | Rosenberg et al. |
| 8,137,258 B1 | 3/2012 | Dennis et al. |
| 8,172,835 B2 | 5/2012 | Leyh et al. |
| 8,192,474 B2 | 6/2012 | Levinson |
| 8,204,446 B2 | 6/2012 | Scheer et al. |
| 8,251,986 B2 | 8/2012 | Chornenky et al. |
| 8,265,763 B2 | 9/2012 | Fahey |
| 8,271,090 B1 | 9/2012 | Hartman et al. |
| 8,275,442 B2 | 9/2012 | Allison |
| 8,285,390 B2 | 10/2012 | Levinson et al. |
| 8,335,566 B2 | 12/2012 | Muller et al. |
| 8,337,539 B2 | 12/2012 | Ting et al. |
| 8,366,756 B2 | 2/2013 | Tucek et al. |
| 8,376,825 B2 | 2/2013 | Guinn et al. |
| 8,376,925 B1 | 2/2013 | Dennis et al. |
| 8,454,591 B2 | 6/2013 | Leyh et al. |
| 8,457,751 B2 | 6/2013 | Pozzato |
| 8,475,354 B2 | 7/2013 | Phillips et al. |
| 8,493,286 B1 | 7/2013 | Agrama |
| 8,523,927 B2 | 9/2013 | Levinson et al. |
| 8,548,599 B2 | 10/2013 | Zarsky et al. |
| 8,565,888 B2 | 10/2013 | Buhlmann et al. |
| 8,579,953 B1 | 11/2013 | Dunbar et al. |
| 8,588,930 B2 | 11/2013 | DiUbaldi et al. |
| 8,593,245 B2 | 11/2013 | Zeng et al. |
| 8,603,073 B2 | 12/2013 | Allison |
| 8,646,239 B2 | 2/2014 | Rulon |
| 8,666,492 B2 | 3/2014 | Muller et al. |
| 8,676,338 B2 | 3/2014 | Levinson |
| 8,684,901 B1 | 4/2014 | Zabara |
| 8,700,176 B2 | 4/2014 | Azar et al. |
| 8,702,774 B2 | 4/2014 | Baker et al. |
| 8,725,270 B2 | 5/2014 | Towe |
| 8,771,326 B2 | 7/2014 | Myeong et al. |
| 8,788,060 B2 | 7/2014 | Nebrigic et al. |
| 8,795,148 B2 | 8/2014 | Schneider et al. |
| 8,834,547 B2 | 9/2014 | Anderson et al. |
| 8,840,608 B2 | 9/2014 | Anderson et al. |
| 8,864,641 B2 | 10/2014 | Riehl et al. |
| 8,868,177 B2 | 10/2014 | Simon et al. |
| 8,906,009 B2 | 12/2014 | Nebrigic et al. |
| 8,915,948 B2 | 12/2014 | Altshuler et al. |
| 8,932,338 B2 | 1/2015 | Lim et al. |
| 8,979,727 B2 | 3/2015 | Ron et al. |
| 8,985,331 B2 | 3/2015 | Guenter et al. |
| 8,998,791 B2 | 4/2015 | Ron Edoute et al. |
| 9,002,477 B2 | 4/2015 | Burnett |
| 9,008,793 B1 | 4/2015 | Cosman, Sr. et al. |
| 9,028,469 B2 | 5/2015 | Jones et al. |
| 9,037,247 B2 | 5/2015 | Simon et al. |
| 9,044,595 B2 | 6/2015 | Araya et al. |
| 9,061,128 B2 | 6/2015 | Hall et al. |
| 9,072,891 B1 | 7/2015 | Rao |
| 9,078,634 B2 | 7/2015 | Gonzales et al. |
| 9,089,719 B2 | 7/2015 | Simon et al. |
| 9,101,524 B2 | 8/2015 | Aghion |
| 9,132,031 B2 | 9/2015 | Levinson et al. |
| 9,149,650 B2 | 10/2015 | Shanks et al. |
| 9,168,096 B2 | 10/2015 | Kreindel |
| 9,233,257 B1 | 1/2016 | Zabara |
| 9,254,395 B1 | 2/2016 | Shambayati |
| 9,261,574 B2 | 2/2016 | Boskamp et al. |
| 9,265,690 B2 | 2/2016 | Kriksunov et al. |
| 9,308,120 B2 | 4/2016 | Anderson et al. |
| 9,314,368 B2 | 4/2016 | Allison et al. |
| 9,326,910 B2 | 5/2016 | Eckhouse et al. |
| 9,339,641 B2 | 5/2016 | Rajguru et al. |
| 9,358,068 B2 | 6/2016 | Schomacker et al. |
| 9,358,149 B2 | 6/2016 | Anderson et al. |
| 9,375,345 B2 | 6/2016 | Levinson et al. |
| 9,387,339 B2 | 7/2016 | Sham et al. |
| 9,398,975 B2 | 7/2016 | Muller et al. |
| 9,408,745 B2 | 8/2016 | Levinson et al. |
| 9,414,759 B2 | 8/2016 | Lang et al. |
| 9,433,797 B2 | 9/2016 | Pilla et al. |
| 9,439,805 B2 | 9/2016 | Gonzales et al. |
| 9,446,258 B1 | 9/2016 | Schwarz |
| 9,468,774 B2 | 10/2016 | {Hacek et al. |
| 9,532,832 B2 | 1/2017 | Ron Edoute et al. |
| 9,545,523 B2 | 1/2017 | Nanda |
| 9,561,357 B2 | 2/2017 | Hall et al. |
| 9,586,057 B2 | 3/2017 | Ladman et al. |
| 9,596,920 B2 | 3/2017 | Shalev et al. |
| 9,610,429 B2 | 4/2017 | Harris et al. |
| 9,610,459 B2 | 4/2017 | Burnett et al. |
| 9,615,854 B2 | 4/2017 | Matsushita |
| 9,636,516 B2 | 5/2017 | Schwarz |
| 9,636,519 B2 | 5/2017 | Ladman et al. |
| 9,649,220 B2 | 5/2017 | Anderson et al. |
| 9,655,770 B2 | 5/2017 | Levinson et al. |
| 9,694,194 B2 | 7/2017 | Ron Edoute et al. |
| 9,737,238 B2 | 8/2017 | Wright et al. |
| 9,737,434 B2 | 8/2017 | Allison |
| 9,757,584 B2 | 9/2017 | Burnett |
| 9,782,324 B2 | 10/2017 | Crunick et al. |
| 9,814,897 B2 | 11/2017 | Ron Edoute et al. |
| 9,844,460 B2 * | 12/2017 | Weber .................. A61F 7/0085 |
| 9,844,461 B2 | 12/2017 | Levinson et al. |
| 9,855,166 B2 | 1/2018 | Anderson et al. |
| 9,861,421 B2 | 1/2018 | O'Neil et al. |
| 9,861,520 B2 | 1/2018 | Baker et al. |

(56) References Cited

U.S. PATENT DOCUMENTS

| | | |
|---|---|---|
| 9,867,996 B2 | 1/2018 | Zarsky et al. |
| 9,901,743 B2 | 2/2018 | Ron Edoute et al. |
| 9,919,161 B2 | 3/2018 | Schwarz |
| 9,937,358 B2 | 4/2018 | Schwarz |
| 9,962,553 B2 | 5/2018 | Schwarz et al. |
| 9,968,797 B2 | 5/2018 | Sham et al. |
| 9,974,519 B1 | 5/2018 | Schwarz |
| 9,974,684 B2 | 5/2018 | Anderson et al. |
| 9,980,765 B2 | 5/2018 | Avram et al. |
| 9,981,143 B2 | 5/2018 | Ron Edoute et al. |
| 9,999,780 B2 | 6/2018 | Weyh et al. |
| 10,037,867 B2 | 7/2018 | Godyak |
| 10,039,929 B1 | 8/2018 | Schwarz et al. |
| 10,080,906 B2 | 9/2018 | Schwarz |
| 10,092,346 B2 | 10/2018 | Levinson |
| 10,111,770 B2 | 10/2018 | Harris et al. |
| 10,111,774 B2 | 10/2018 | Gonzales et al. |
| 10,124,187 B2 | 11/2018 | Schwarz et al. |
| 10,183,172 B2 | 1/2019 | Ghiron et al. |
| 10,195,453 B2 | 2/2019 | Schwarz |
| 10,195,454 B2 | 2/2019 | Yamashiro |
| 10,201,380 B2 | 2/2019 | Debenedictis et al. |
| 10,245,439 B1 | 4/2019 | Schwarz et al. |
| 10,271,900 B2 | 4/2019 | Marchitto et al. |
| 10,342,988 B2 | 7/2019 | Midorikawa et al. |
| 10,413,745 B2 | 9/2019 | Riehl |
| 10,463,869 B2 | 11/2019 | Ron Edoute et al. |
| 10,471,269 B1 | 11/2019 | Schwarz et al. |
| 10,478,588 B2 | 11/2019 | Walpole et al. |
| 10,478,633 B2 | 11/2019 | Schwarz et al. |
| 10,478,634 B2 | 11/2019 | Schwarz et al. |
| 10,493,293 B2 | 12/2019 | Schwarz et al. |
| 10,518,098 B2 | 12/2019 | Hong et al. |
| 10,549,109 B2 | 2/2020 | Schwarz |
| 10,549,110 B1 | 2/2020 | Schwarz et al. |
| 10,556,121 B2 | 2/2020 | Gurfein |
| 10,556,122 B1 | 2/2020 | Schwarz et al. |
| 10,569,094 B2 | 2/2020 | Schwarz |
| 10,569,095 B1 | 2/2020 | Schwarz et al. |
| 10,583,287 B2 | 3/2020 | Schwarz |
| 10,596,386 B2 | 3/2020 | Schwarz et al. |
| 10,610,696 B1 | 4/2020 | Peled |
| 10,632,321 B2 | 4/2020 | Schwarz et al. |
| 10,639,490 B2 | 5/2020 | Simon et al. |
| 10,661,093 B2 | 5/2020 | Ron Edoute et al. |
| 10,675,819 B2 | 6/2020 | Li et al. |
| 10,688,310 B2 | 6/2020 | Schwarz et al. |
| 10,695,575 B1 | 6/2020 | Schwarz et al. |
| 10,695,576 B2 | 6/2020 | Schwarz et al. |
| 10,709,894 B2 | 7/2020 | Schwarz et al. |
| 10,709,895 B2 | 7/2020 | Schwarz et al. |
| 10,806,943 B2 | 10/2020 | Sokolowski |
| 10,821,295 B1 | 11/2020 | Schwarz et al. |
| 10,849,784 B2 | 12/2020 | Jurna et al. |
| 2001/0018547 A1 | 8/2001 | Mechlenburg et al. |
| 2001/0031906 A1 | 10/2001 | Ishikawa et al. |
| 2002/0010414 A1 | 1/2002 | Coston et al. |
| 2002/0049483 A1 | 4/2002 | Knowlton |
| 2002/0082466 A1 | 6/2002 | Han |
| 2002/0128686 A1 | 9/2002 | Minogue et al. |
| 2002/0143365 A1 | 10/2002 | Herbst |
| 2002/0160436 A1 | 10/2002 | Markov et al. |
| 2002/0165590 A1 | 11/2002 | Crowe et al. |
| 2003/0028072 A1 | 2/2003 | Fischell et al. |
| 2003/0032900 A1 | 2/2003 | Ella |
| 2003/0032950 A1 | 2/2003 | Altshuler et al. |
| 2003/0050527 A1 | 3/2003 | Fox et al. |
| 2003/0074037 A1 | 4/2003 | Moore et al. |
| 2003/0078646 A1 | 4/2003 | Axelgaard |
| 2003/0093133 A1 | 5/2003 | Crowe et al. |
| 2003/0130711 A1 | 7/2003 | Pearson et al. |
| 2003/0149451 A1 | 8/2003 | Chomenky et al. |
| 2003/0153958 A1 | 8/2003 | Yamazaki et al. |
| 2003/0158585 A1 | 8/2003 | Burnett |
| 2003/0216729 A1 | 11/2003 | Marchitto et al. |
| 2003/0220674 A1 | 11/2003 | Anderson et al. |
| 2003/0236487 A1 | 12/2003 | Knowlton |
| 2004/0015163 A1 | 1/2004 | Buysse et al. |
| 2004/0034346 A1 | 2/2004 | Stern et al. |
| 2004/0039279 A1 | 2/2004 | Ruohonen |
| 2004/0073079 A1 | 4/2004 | Altshuler et al. |
| 2004/0077977 A1 | 4/2004 | Ella et al. |
| 2004/0093042 A1 | 5/2004 | Altshuler et al. |
| 2004/0102768 A1 | 5/2004 | Cluzeau et al. |
| 2004/0162583 A1 | 8/2004 | Bingham et al. |
| 2004/0193003 A1 | 9/2004 | Mechlenburg et al. |
| 2004/0206365 A1 | 10/2004 | Knowlton |
| 2004/0210214 A1 | 10/2004 | Knowlton |
| 2004/0210282 A1 | 10/2004 | Flock et al. |
| 2004/0210287 A1 | 10/2004 | Greene |
| 2004/0230226 A1 | 11/2004 | Bingham et al. |
| 2005/0038313 A1 | 2/2005 | Ardizzone |
| 2005/0049543 A1 | 3/2005 | Anderson et al. |
| 2005/0075701 A1 | 4/2005 | Shafer |
| 2005/0075702 A1 | 4/2005 | Shafer |
| 2005/0090814 A1 | 4/2005 | Lalonde et al. |
| 2005/0107656 A1 | 5/2005 | Jang et al. |
| 2005/0134193 A1 | 6/2005 | Myers et al. |
| 2005/0187599 A1 | 8/2005 | Sharkey et al. |
| 2005/0203504 A1 | 9/2005 | Wham et al. |
| 2005/0215987 A1 | 9/2005 | Slatkine |
| 2005/0216062 A1 | 9/2005 | Herbst |
| 2005/0251120 A1 | 11/2005 | Anderson et al. |
| 2006/0004244 A1 | 1/2006 | Phillips et al. |
| 2006/0020236 A1 | 1/2006 | Ben-Nun |
| 2006/0036300 A1 | 2/2006 | Kreindel |
| 2006/0094924 A1 | 5/2006 | Riehl |
| 2006/0106375 A1 | 5/2006 | Werneth et al. |
| 2006/0152301 A1 | 7/2006 | Rohwedder |
| 2006/0184214 A1 | 8/2006 | McDANIEL |
| 2006/0187607 A1 | 8/2006 | Mo |
| 2006/0195168 A1 | 8/2006 | Dunbar et al. |
| 2006/0199992 A1 | 9/2006 | Eisenberg et al. |
| 2006/0206103 A1 | 9/2006 | Altshuler et al. |
| 2006/0206180 A1 | 9/2006 | Alcidi |
| 2006/0253176 A1 | 11/2006 | Caruso et al. |
| 2006/0259102 A1 | 11/2006 | Slatkine |
| 2006/0271028 A1 | 11/2006 | Altshuler et al. |
| 2006/0287566 A1 | 12/2006 | Zangen et al. |
| 2006/0293719 A1 | 12/2006 | Naghavi |
| 2007/0010766 A1 | 1/2007 | Gil et al. |
| 2007/0010861 A1 | 1/2007 | Anderson et al. |
| 2007/0016274 A1 | 1/2007 | Boveja et al. |
| 2007/0027411 A1 | 2/2007 | Ella et al. |
| 2007/0083237 A1 | 4/2007 | Teruel |
| 2007/0088413 A1 | 4/2007 | Weber et al. |
| 2007/0088419 A1 | 4/2007 | Fiorina et al. |
| 2007/0135811 A1 | 6/2007 | Hooven |
| 2007/0142886 A1 | 6/2007 | Fischell et al. |
| 2007/0173749 A1 | 7/2007 | Williams et al. |
| 2007/0173805 A1 | 7/2007 | Weinberg et al. |
| 2007/0179534 A1 | 8/2007 | Firlik et al. |
| 2007/0198071 A1 | 8/2007 | Ting et al. |
| 2007/0232966 A1 | 10/2007 | Applebaum et al. |
| 2007/0244530 A1 | 10/2007 | Ren |
| 2007/0255355 A1 | 11/2007 | Altshuler et al. |
| 2007/0255362 A1 | 11/2007 | Levinson et al. |
| 2007/0260107 A1 | 11/2007 | Mishelevich et al. |
| 2007/0270795 A1 | 11/2007 | Francischelli et al. |
| 2007/0270925 A1 | 11/2007 | Levinson |
| 2007/0282156 A1 | 12/2007 | Konings |
| 2007/0293911 A1 | 12/2007 | Crowe et al. |
| 2007/0293918 A1 | 12/2007 | Thompson et al. |
| 2008/0009885 A1 | 1/2008 | Del Giglio |
| 2008/0046053 A1 | 2/2008 | Wagner et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0082094 A1 | 4/2008 | McPHERSON et al. |
| 2008/0082153 A1 | 4/2008 | Gadsby et al. |
| 2008/0103565 A1 | 5/2008 | Altshuler et al. |
| 2008/0132971 A1 | 6/2008 | Pille et al. |
| 2008/0183251 A1 | 7/2008 | Azar et al. |
| 2008/0188915 A1 | 8/2008 | Mills et al. |

(56) References Cited

U.S. PATENT DOCUMENTS

| | | |
|---|---|---|
| 2008/0228520 A1 | 9/2008 | Day et al. |
| 2008/0234534 A1 | 9/2008 | Mikas et al. |
| 2008/0249350 A1 | 10/2008 | Marchitto et al. |
| 2008/0255572 A1 | 10/2008 | Zeller et al. |
| 2008/0255637 A1 | 10/2008 | Oishi |
| 2008/0262287 A1 | 10/2008 | Dussau |
| 2008/0262574 A1 | 10/2008 | Briefs et al. |
| 2008/0287839 A1 | 11/2008 | Rosen et al. |
| 2008/0287948 A1 | 11/2008 | Newton et al. |
| 2008/0306325 A1 | 12/2008 | Burnett et al. |
| 2008/0306326 A1 | 12/2008 | Epstein |
| 2008/0312647 A1 | 12/2008 | Knopp et al. |
| 2009/0005631 A1 | 1/2009 | Simenhaus et al. |
| 2009/0018384 A1 | 1/2009 | Boyden et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0018628 A1 | 1/2009 | Burns et al. |
| 2009/0024192 A1 | 1/2009 | Mulholland |
| 2009/0024193 A1 | 1/2009 | Altshuler et al. |
| 2009/0036958 A1 | 2/2009 | Mehta |
| 2009/0043293 A1 | 2/2009 | Pankratov et al. |
| 2009/0099405 A1 | 4/2009 | Schneider et al. |
| 2009/0108969 A1 | 4/2009 | Sims et al. |
| 2009/0118722 A1 | 5/2009 | Ebbers et al. |
| 2009/0118790 A1 | 5/2009 | Van Herk |
| 2009/0149300 A1 | 6/2009 | Chen |
| 2009/0149929 A1 | 6/2009 | Levinson et al. |
| 2009/0149930 A1 | 6/2009 | Schenck |
| 2009/0156958 A1 | 6/2009 | Mehta et al. |
| 2009/0221938 A1 | 9/2009 | Rosenberg et al. |
| 2009/0227831 A1 | 9/2009 | Burnett et al. |
| 2009/0234423 A1 | 9/2009 | Vetanze |
| 2009/0248004 A1 | 10/2009 | Altshuler et al. |
| 2009/0254154 A1 | 10/2009 | De Taboada et al. |
| 2009/0270945 A1 | 10/2009 | Markoll et al. |
| 2009/0284339 A1 | 11/2009 | Choi et al. |
| 2009/0306648 A1 | 12/2009 | Podhajsky et al. |
| 2009/0326571 A1 | 12/2009 | Mulholland |
| 2010/0004536 A1 | 1/2010 | Rosenberg |
| 2010/0004715 A1 | 1/2010 | Fahey |
| 2010/0016761 A1 | 1/2010 | Rosenberg |
| 2010/0036191 A1 | 2/2010 | Walter et al. |
| 2010/0036368 A1 | 2/2010 | England et al. |
| 2010/0049188 A1 | 2/2010 | Nelson et al. |
| 2010/0069704 A1 | 3/2010 | Peterchev |
| 2010/0081971 A1 | 4/2010 | Allison |
| 2010/0087699 A1 | 4/2010 | Peterchev |
| 2010/0087816 A1 | 4/2010 | Roy |
| 2010/0121131 A1 | 5/2010 | Mathes |
| 2010/0130945 A1 | 5/2010 | Laniado et al. |
| 2010/0145399 A1 | 6/2010 | Johari et al. |
| 2010/0152522 A1 | 6/2010 | Roth et al. |
| 2010/0152824 A1 | 6/2010 | Allison |
| 2010/0160712 A1 | 6/2010 | Burnett et al. |
| 2010/0168501 A1 | 7/2010 | Burnett et al. |
| 2010/0179372 A1 | 7/2010 | Glassman |
| 2010/0185042 A1 | 7/2010 | Schneider et al. |
| 2010/0217253 A1 | 8/2010 | Mehta |
| 2010/0222629 A1 | 9/2010 | Burnett et al. |
| 2010/0228250 A1 | 9/2010 | Brogna |
| 2010/0256438 A1 | 10/2010 | Mishelevich et al. |
| 2010/0256439 A1 | 10/2010 | Schneider et al. |
| 2010/0261992 A1 | 10/2010 | Axelgaard |
| 2010/0274327 A1 | 10/2010 | Carroll et al. |
| 2010/0274329 A1 | 10/2010 | Bradley et al. |
| 2010/0280582 A1 | 11/2010 | Baker et al. |
| 2010/0286470 A1 | 11/2010 | Schneider et al. |
| 2010/0286691 A1 | 11/2010 | Kerr et al. |
| 2010/0298623 A1 | 11/2010 | Mishelevich et al. |
| 2010/0309689 A1 | 12/2010 | Coulson |
| 2010/0324611 A1 | 12/2010 | Deming et al. |
| 2010/0331602 A1 | 12/2010 | Mishelevich et al. |
| 2010/0331603 A1 | 12/2010 | Szecsi |
| 2011/0004261 A1 | 1/2011 | Sham et al. |
| 2011/0007745 A1 | 1/2011 | Schultz et al. |
| 2011/0009737 A1 | 1/2011 | Manstein |
| 2011/0015464 A1 | 1/2011 | Riehl et al. |
| 2011/0021863 A1 | 1/2011 | Burnett et al. |
| 2011/0046432 A1 | 2/2011 | Simon et al. |
| 2011/0046523 A1 | 2/2011 | Altshuler et al. |
| 2011/0066216 A1 | 3/2011 | Ting et al. |
| 2011/0077451 A1 | 3/2011 | Marchitto et al. |
| 2011/0082383 A1 | 4/2011 | Cory et al. |
| 2011/0087312 A1 | 4/2011 | Shanks et al. |
| 2011/0105826 A1 | 5/2011 | Mishelevich et al. |
| 2011/0112520 A1 | 5/2011 | Michael |
| 2011/0118722 A1 | 5/2011 | Lischinsky et al. |
| 2011/0125203 A1 | 5/2011 | Simon et al. |
| 2011/0130618 A1 | 6/2011 | Ron et al. |
| 2011/0130713 A1 | 6/2011 | Dufay |
| 2011/0130796 A1 | 6/2011 | Louise |
| 2011/0152967 A1 | 6/2011 | Simon et al. |
| 2011/0172735 A1 | 7/2011 | Johari |
| 2011/0172752 A1 | 7/2011 | Bingham et al. |
| 2011/0190569 A1 | 8/2011 | Simon et al. |
| 2011/0196438 A1 | 8/2011 | Mnozil et al. |
| 2011/0202058 A1 | 8/2011 | Eder et al. |
| 2011/0218464 A1 | 9/2011 | Iger |
| 2011/0224761 A1 | 9/2011 | Manstein |
| 2011/0237921 A1 | 9/2011 | Askin, III et al. |
| 2011/0238050 A1 | 9/2011 | Allison et al. |
| 2011/0238051 A1 | 9/2011 | Levinson et al. |
| 2011/0245900 A1 | 10/2011 | Turner et al. |
| 2011/0263925 A1 | 10/2011 | Bratton |
| 2011/0273251 A1 | 11/2011 | Mishelevich et al. |
| 2011/0275927 A1 | 11/2011 | Wagner et al. |
| 2011/0276108 A1 | 11/2011 | Crowe et al. |
| 2011/0300079 A1 | 12/2011 | Martens et al. |
| 2011/0306943 A1 | 12/2011 | Dunbar et al. |
| 2011/0319700 A1 | 12/2011 | Schneider |
| 2012/0016359 A1 | 1/2012 | Podhajsky |
| 2012/0022518 A1 | 1/2012 | Levinson |
| 2012/0029394 A1 | 2/2012 | Babaev |
| 2012/0035608 A1 | 2/2012 | Marchitto et al. |
| 2012/0046598 A1 | 2/2012 | Kardos et al. |
| 2012/0046653 A1 | 2/2012 | Welches et al. |
| 2012/0053449 A1 | 3/2012 | Moses et al. |
| 2012/0101326 A1 | 4/2012 | Simon et al. |
| 2012/0108883 A1 | 5/2012 | Peterchev |
| 2012/0108884 A1 | 5/2012 | Bechler et al. |
| 2012/0109241 A1 | 5/2012 | Rauscher |
| 2012/0116271 A1 | 5/2012 | Caruso et al. |
| 2012/0150079 A1 | 6/2012 | Rosenberg |
| 2012/0157747 A1 | 6/2012 | Rybski et al. |
| 2012/0158100 A1 | 6/2012 | Schomacker |
| 2012/0172653 A1 | 7/2012 | Chornenky et al. |
| 2012/0197361 A1 | 8/2012 | Gonzales et al. |
| 2012/0215210 A1 | 8/2012 | Brown et al. |
| 2012/0226272 A1 | 9/2012 | Chernov et al. |
| 2012/0226330 A1 | 9/2012 | Kolen et al. |
| 2012/0239123 A1 | 9/2012 | Weber et al. |
| 2012/0240940 A1 | 9/2012 | Paraschac et al. |
| 2012/0245483 A1 | 9/2012 | Lundqvist |
| 2012/0253098 A1 | 10/2012 | George et al. |
| 2012/0259382 A1 | 10/2012 | Trier et al. |
| 2012/0271206 A1* | 10/2012 | Shalev ............... A61H 9/0057 607/3 |
| 2012/0271294 A1 | 10/2012 | Barthe et al. |
| 2012/0277587 A1 | 11/2012 | Adanny et al. |
| 2012/0302821 A1 | 11/2012 | Burnett |
| 2012/0303076 A1 | 11/2012 | Fahey |
| 2012/0310033 A1 | 12/2012 | Muntermann |
| 2012/0310035 A1 | 12/2012 | Schneider et al. |
| 2012/0310311 A1 | 12/2012 | Elkah |
| 2012/0330090 A1 | 12/2012 | Sham et al. |
| 2013/0006039 A1 | 1/2013 | Sadler |
| 2013/0012755 A1 | 1/2013 | Slayton |
| 2013/0030239 A1 | 1/2013 | Weyh et al. |
| 2013/0035745 A1 | 2/2013 | Ahmed et al. |
| 2013/0053620 A1 | 2/2013 | Susedik et al. |
| 2013/0066309 A1 | 3/2013 | Levinson |

(56) References Cited

U.S. PATENT DOCUMENTS

| | | |
|---|---|---|
| 2013/0079684 A1 | 3/2013 | Rosen et al. |
| 2013/0096363 A1 | 4/2013 | Schneider et al. |
| 2013/0103127 A1 | 4/2013 | Mueller et al. |
| 2013/0116758 A1 | 5/2013 | Levinson et al. |
| 2013/0116759 A1 | 5/2013 | Levinson et al. |
| 2013/0123568 A1 | 5/2013 | Hamilton et al. |
| 2013/0123629 A1 | 5/2013 | Rosenberg et al. |
| 2013/0123764 A1 | 5/2013 | Zarsky et al. |
| 2013/0123765 A1 | 5/2013 | Zarsky et al. |
| 2013/0131764 A1 | 5/2013 | Grove |
| 2013/0137918 A1 | 5/2013 | Phillips et al. |
| 2013/0144280 A1 | 6/2013 | Eckhouse et al. |
| 2013/0150653 A1 | 6/2013 | Borsody |
| 2013/0158440 A1 | 6/2013 | Allison |
| 2013/0158634 A1 | 6/2013 | Ron et al. |
| 2013/0158636 A1 | 6/2013 | Ting et al. |
| 2013/0178764 A1 | 7/2013 | Eckhouse et al. |
| 2013/0184693 A1 | 7/2013 | Neev |
| 2013/0190744 A1 | 7/2013 | Avram et al. |
| 2013/0238043 A1 | 9/2013 | Beardall et al. |
| 2013/0238061 A1 | 9/2013 | Ron et al. |
| 2013/0238062 A1 | 9/2013 | Ron Edoute et al. |
| 2013/0245731 A1 | 9/2013 | Allison |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0261374 A1 | 10/2013 | Elder |
| 2013/0261683 A1 | 10/2013 | Soikum et al. |
| 2013/0267943 A1 | 10/2013 | Hancock |
| 2013/0289433 A1 | 10/2013 | Jin et al. |
| 2013/0303904 A1 | 11/2013 | Barthe et al. |
| 2013/0304159 A1 | 11/2013 | Simon et al. |
| 2013/0317281 A1 | 11/2013 | Schneider et al. |
| 2013/0317282 A1 | 11/2013 | Ron Edoute et al. |
| 2013/0331637 A1 | 12/2013 | Greff |
| 2014/0005758 A1 | 1/2014 | Ben-Yehuda et al. |
| 2014/0005759 A1 | 1/2014 | Fahey et al. |
| 2014/0005760 A1 | 1/2014 | Levinson et al. |
| 2014/0012064 A1 | 1/2014 | Riehl et al. |
| 2014/0018767 A1 | 1/2014 | Harris et al. |
| 2014/0025033 A1 | 1/2014 | Mirkov et al. |
| 2014/0025142 A1 | 1/2014 | Zarksy et al. |
| 2014/0046423 A1 | 2/2014 | Rajguru et al. |
| 2014/0066786 A1 | 3/2014 | Naghavi et al. |
| 2014/0067025 A1 | 3/2014 | Levinson et al. |
| 2014/0081359 A1 | 3/2014 | Sand |
| 2014/0148870 A1 | 5/2014 | Burnett |
| 2014/0194958 A1 | 7/2014 | Chabal et al. |
| 2014/0200388 A1 | 7/2014 | Schneider et al. |
| 2014/0221990 A1 | 8/2014 | Kreindel |
| 2014/0235928 A1 | 8/2014 | Zangen et al. |
| 2014/0243933 A1 | 8/2014 | Ginggen |
| 2014/0249355 A1 | 9/2014 | Martinez |
| 2014/0249601 A1 | 9/2014 | Bachinski et al. |
| 2014/0249609 A1 | 9/2014 | Zarsky et al. |
| 2014/0257071 A1 | 9/2014 | Curran et al. |
| 2014/0257443 A1 | 9/2014 | Baker et al. |
| 2014/0276248 A1 | 9/2014 | Hall et al. |
| 2014/0276693 A1 | 9/2014 | Altshuler et al. |
| 2014/0277219 A1 | 9/2014 | Nanda |
| 2014/0277302 A1 | 9/2014 | Weber et al. |
| 2014/0303425 A1 | 10/2014 | Pilla et al. |
| 2014/0303525 A1 | 10/2014 | Sitharaman |
| 2014/0303696 A1 | 10/2014 | Anderson et al. |
| 2014/0303697 A1 | 10/2014 | Anderson et al. |
| 2014/0316393 A1 | 10/2014 | Levinson |
| 2014/0324120 A1 | 10/2014 | Bogie et al. |
| 2014/0330067 A1 | 11/2014 | Jordan |
| 2014/0350438 A1 | 11/2014 | Papirov et al. |
| 2014/0357935 A1 | 12/2014 | Ilmoniemi et al. |
| 2014/0364841 A1 | 12/2014 | Kornstein |
| 2014/0371515 A1 | 12/2014 | John |
| 2014/0378875 A1 | 12/2014 | Ron Edoute et al. |
| 2015/0005569 A1 | 1/2015 | Missoli |
| 2015/0005759 A1 | 1/2015 | Welches et al. |
| 2015/0018667 A1 | 1/2015 | Radman et al. |
| 2015/0025299 A1 | 1/2015 | Ron et al. |
| 2015/0080769 A1 | 3/2015 | Lotsch |
| 2015/0088105 A1 | 3/2015 | Fatemi |
| 2015/0094788 A1 | 4/2015 | Pierenkemper |
| 2015/0112412 A1 | 4/2015 | Anderson et al. |
| 2015/0119849 A1 | 4/2015 | Aronhalt et al. |
| 2015/0123661 A1 | 5/2015 | Yui et al. |
| 2015/0127075 A1 | 5/2015 | Ward et al. |
| 2015/0133717 A1 | 5/2015 | Ghiron et al. |
| 2015/0133718 A1 | 5/2015 | Schneider et al. |
| 2015/0141877 A1 | 5/2015 | Feldman |
| 2015/0148858 A1 | 5/2015 | Kaib |
| 2015/0157873 A1 | 6/2015 | Sokolowski |
| 2015/0165226 A1 | 6/2015 | Simon et al. |
| 2015/0165232 A1 | 6/2015 | Altshuler et al. |
| 2015/0165238 A1 | 6/2015 | Slayton et al. |
| 2015/0174002 A1 | 6/2015 | Burbank et al. |
| 2015/0202454 A1 | 7/2015 | Burnett |
| 2015/0216719 A1 | 8/2015 | Debenedictis et al. |
| 2015/0216720 A1 | 8/2015 | Debenedictis et al. |
| 2015/0216816 A1 | 8/2015 | O'Neil et al. |
| 2015/0223975 A1 | 8/2015 | Anderson et al. |
| 2015/0238248 A1 | 8/2015 | Thompson et al. |
| 2015/0238771 A1 | 8/2015 | Zarsk et al. |
| 2015/0272776 A1 | 10/2015 | Gonzales et al. |
| 2015/0283022 A1 | 10/2015 | Lee et al. |
| 2015/0297909 A1 | 10/2015 | Peashock |
| 2015/0314133 A1 | 11/2015 | Yamashiro |
| 2015/0328077 A1 | 11/2015 | Levinson |
| 2015/0328475 A1 | 11/2015 | Kim et al. |
| 2015/0342661 A1 | 12/2015 | Ron Edoute |
| 2015/0342780 A1 | 12/2015 | Levinson et al. |
| 2015/0360045 A1 | 12/2015 | Fischell et al. |
| 2015/0367141 A1 | 12/2015 | Goetz et al. |
| 2015/0375005 A1 | 12/2015 | Segal |
| 2016/0015995 A1 | 1/2016 | Leung et al. |
| 2016/0016013 A1 | 1/2016 | Capelli et al. |
| 2016/0020070 A1 | 1/2016 | Kim et al. |
| 2016/0022349 A1 | 1/2016 | Woloszko et al. |
| 2016/0030763 A1 | 2/2016 | Midorikawa et al. |
| 2016/0045755 A1 | 2/2016 | Chun et al. |
| 2016/0051401 A1 | 2/2016 | Yee et al. |
| 2016/0051827 A1 | 2/2016 | Ron et al. |
| 2016/0066977 A1 | 3/2016 | Neal, II et al. |
| 2016/0066994 A1 | 3/2016 | Shanks |
| 2016/0067516 A1 | 3/2016 | Schneider et al. |
| 2016/0067517 A1 | 3/2016 | Burnett |
| 2016/0089550 A1 | 3/2016 | Debenedictis et al. |
| 2016/0106982 A1 | 4/2016 | Cakmak et al. |
| 2016/0121112 A1 | 5/2016 | Azar |
| 2016/0129273 A1 | 5/2016 | Park |
| 2016/0129274 A1 | 5/2016 | Park |
| 2016/0136462 A1 | 5/2016 | Lewis, Jr. et al. |
| 2016/0150494 A1 | 5/2016 | Tabet et al. |
| 2016/0151637 A1 | 6/2016 | Abe et al. |
| 2016/0158574 A1 | 6/2016 | Eckhouse et al. |
| 2016/0175193 A1 | 6/2016 | Jung |
| 2016/0184601 A1 | 6/2016 | Gleich et al. |
| 2016/0193466 A1 | 7/2016 | Burnett |
| 2016/0213924 A1 | 7/2016 | Coleman et al. |
| 2016/0220834 A1 | 8/2016 | Schwarz |
| 2016/0250494 A1 | 9/2016 | Sakaki et al. |
| 2016/0256702 A1 | 9/2016 | Schwarz et al. |
| 2016/0256703 A1 | 9/2016 | Schwarz et al. |
| 2016/0270951 A1 | 9/2016 | Martins et al. |
| 2016/0317346 A1 | 11/2016 | Kovach |
| 2016/0317827 A1 | 11/2016 | Schwarz et al. |
| 2016/0324684 A1 | 11/2016 | Levinson et al. |
| 2016/0346561 A1 | 12/2016 | Ron Edoute et al. |
| 2016/0354237 A1 | 12/2016 | Gonzales et al. |
| 2017/0001024 A1 | 1/2017 | Prouza |
| 2017/0001025 A1 | 1/2017 | Schwarz et al. |
| 2017/0001026 A1 | 1/2017 | Schwarz et al. |
| 2017/0001027 A1 | 1/2017 | Ladman et al. |
| 2017/0001028 A1 | 1/2017 | Ladman et al. |
| 2017/0001029 A1 | 1/2017 | Pribula et al. |

(56) References Cited

U.S. PATENT DOCUMENTS

| | | |
|---|---|---|
| 2017/0001030 A1 | 1/2017 | Pribula et al. |
| 2017/0007309 A1 | 1/2017 | Debenedictis et al. |
| 2017/0036019 A1 | 2/2017 | Matsushita |
| 2017/0043177 A1 | 2/2017 | Ron Edoute et al. |
| 2017/0050019 A1 | 2/2017 | Ron Edoute et al. |
| 2017/0072212 A1 | 3/2017 | Ladman et al. |
| 2017/0087373 A1 | 3/2017 | Schwarz |
| 2017/0100585 A1 | 4/2017 | Hall et al. |
| 2017/0105869 A1 | 4/2017 | Frangineas, Jr. |
| 2017/0106201 A1 | 4/2017 | Schwarz et al. |
| 2017/0106203 A1 | 4/2017 | Schneider et al. |
| 2017/0120067 A1 | 5/2017 | Prouza |
| 2017/0143958 A1 | 5/2017 | Shalev et al. |
| 2017/0156907 A1 | 6/2017 | Harris et al. |
| 2017/0173347 A1 | 6/2017 | Schwarz et al. |
| 2017/0182334 A1 | 6/2017 | Altshuler et al. |
| 2017/0182335 A1 | 6/2017 | Altshuler et al. |
| 2017/0189707 A1 | 7/2017 | Zabara |
| 2017/0196731 A1 | 7/2017 | Debenedictis et al. |
| 2017/0209708 A1 | 7/2017 | Schwarz |
| 2017/0239079 A1 | 8/2017 | Root et al. |
| 2017/0239467 A1 | 8/2017 | Shalev et al. |
| 2017/0259077 A1 | 9/2017 | Jin |
| 2017/0280889 A1 | 10/2017 | Koch |
| 2017/0304642 A1 | 10/2017 | Ron Edoute et al. |
| 2017/0319378 A1 | 11/2017 | Anderson et al. |
| 2017/0325992 A1 | 11/2017 | Debenedictis et al. |
| 2017/0325993 A1 | 11/2017 | Jimenez et al. |
| 2017/0326042 A1 | 11/2017 | Zeng et al. |
| 2017/0326346 A1 | 11/2017 | Jimenez et al. |
| 2017/0333705 A1 | 11/2017 | Schwarz |
| 2017/0348143 A1 | 12/2017 | Rosen et al. |
| 2017/0348539 A1 | 12/2017 | Schwarz et al. |
| 2017/0354530 A1 | 12/2017 | Shagdar et al. |
| 2017/0361095 A1 | 12/2017 | Mueller et al. |
| 2018/0000347 A1 | 1/2018 | Perez et al. |
| 2018/0001106 A1 | 1/2018 | Schwarz |
| 2018/0001107 A1 | 1/2018 | Schwarz et al. |
| 2018/0021565 A1 | 1/2018 | Dar et al. |
| 2018/0028831 A1 | 2/2018 | Ron Edoute et al. |
| 2018/0036548 A1 | 2/2018 | Nusse |
| 2018/0043151 A1 | 2/2018 | Ejiri et al. |
| 2018/0071544 A1 | 3/2018 | Ghiron et al. |
| 2018/0103991 A1 | 4/2018 | Linhart et al. |
| 2018/0125416 A1 | 5/2018 | Schwarz et al. |
| 2018/0133498 A1 | 5/2018 | Chornenky et al. |
| 2018/0153736 A1 | 6/2018 | Mills et al. |
| 2018/0153760 A1 | 6/2018 | Rosen et al. |
| 2018/0161197 A1 | 6/2018 | Baker et al. |
| 2018/0177996 A1 | 6/2018 | Gozani et al. |
| 2018/0185081 A1 | 7/2018 | O'Neil et al. |
| 2018/0185189 A1 | 7/2018 | Weber et al. |
| 2018/0214300 A1 | 8/2018 | Anderson et al. |
| 2018/0228646 A1 | 8/2018 | Gonzales et al. |
| 2018/0229048 A1 | 8/2018 | Sikora et al. |
| 2018/0236254 A1 | 8/2018 | Schwarz et al. |
| 2018/0250056 A1 | 9/2018 | Avram et al. |
| 2018/0263677 A1 | 9/2018 | Hilton et al. |
| 2018/0264245 A1 | 9/2018 | Edwards et al. |
| 2018/0271767 A1 | 9/2018 | Jimenez et al. |
| 2018/0296831 A1 | 10/2018 | Matsushita |
| 2018/0310950 A1 | 11/2018 | Yee et al. |
| 2018/0345012 A1 | 12/2018 | Schwarz et al. |
| 2018/0353767 A1 | 12/2018 | Biginton |
| 2019/0000524 A1 | 1/2019 | Rosen et al. |
| 2019/0000529 A1 | 1/2019 | Kothare et al. |
| 2019/0000663 A1 | 1/2019 | Anderson et al. |
| 2019/0029876 A1 | 1/2019 | Anderson et al. |
| 2019/0030356 A1 | 1/2019 | Schwarz |
| 2019/0053941 A1 | 2/2019 | Samson |
| 2019/0111255 A1 | 4/2019 | Errico et al. |
| 2019/0117965 A1 | 4/2019 | Iger et al. |
| 2019/0134414 A1 | 5/2019 | Schwarz |
| 2019/0151655 A1 | 5/2019 | Hall et al. |
| 2019/0168012 A1 | 6/2019 | Biginton |
| 2019/0183562 A1 | 6/2019 | Widgerow |
| 2019/0192219 A1 | 6/2019 | Kreindel |
| 2019/0192853 A1 | 6/2019 | Kim et al. |
| 2019/0192872 A1 | 6/2019 | Schwarz et al. |
| 2019/0192873 A1 | 6/2019 | Schwarz et al. |
| 2019/0192875 A1 | 6/2019 | Schwarz et al. |
| 2019/0201705 A1 | 7/2019 | Schwarz et al. |
| 2019/0201706 A1 | 7/2019 | Schwarz et al. |
| 2019/0209836 A1 | 7/2019 | Yakoub et al. |
| 2019/0255346 A1 | 8/2019 | Ghiron |
| 2019/0269909 A1 | 9/2019 | Gozani et al. |
| 2019/0275320 A1 | 9/2019 | Kim et al. |
| 2019/0299018 A1 | 10/2019 | Chornenky et al. |
| 2019/0314629 A1 | 10/2019 | Kreindel |
| 2019/0314638 A1 | 10/2019 | Kreindel |
| 2019/0329065 A1 | 10/2019 | Gandel |
| 2019/0336783 A1 | 11/2019 | Sokolowski |
| 2019/0344091 A1 | 11/2019 | Fischer |
| 2019/0350646 A1 | 11/2019 | Kreindel |
| 2019/0365462 A1 | 12/2019 | Casalino |
| 2019/0388698 A1 | 12/2019 | Schwarz et al. |
| 2020/0001103 A1 | 1/2020 | Schwarz et al. |
| 2020/0016422 A1 | 1/2020 | Ron Edoute et al. |
| 2020/0016423 A1 | 1/2020 | Ron Edoute et al. |
| 2020/0054890 A1 | 2/2020 | Schwarz et al. |
| 2020/0061385 A1 | 2/2020 | Schwarz et al. |
| 2020/0061386 A1 | 2/2020 | Schwarz et al. |
| 2020/0094066 A1 | 3/2020 | Heath |
| 2020/0114160 A1 | 4/2020 | Blendermann |
| 2020/0129759 A1 | 4/2020 | Schwarz |
| 2020/0139148 A1 | 5/2020 | Schwarz et al. |
| 2020/0155221 A1 | 5/2020 | Marchitto et al. |
| 2020/0171297 A1 | 6/2020 | Kirson et al. |
| 2020/0197696 A1 | 6/2020 | Nagel et al. |
| 2020/0206524 A1 | 7/2020 | Katznelson et al. |
| 2020/0237424 A1 | 7/2020 | Hunziker et al. |
| 2020/0281642 A1 | 9/2020 | Kreindel |
| 2020/0289838 A1 | 9/2020 | Schwarz et al. |
| 2020/0324133 A1 | 10/2020 | Schwarz et al. |
| 2020/0330782 A1 | 10/2020 | Zabara |
| 2020/0352633 A1 | 11/2020 | Treen et al. |
| 2020/0353244 A1 | 11/2020 | Yamazaki |
| 2020/0353273 A1 | 11/2020 | Zucco |
| 2020/0360681 A1 | 11/2020 | Lay |
| 2021/0008369 A1 | 1/2021 | Crosson |
| 2021/0038894 A1 | 2/2021 | Mowery et al. |
| 2021/0146150 A1 | 5/2021 | Frangineas, Jr. et al. |
| 2021/0275825 A1 | 9/2021 | Kreindel |
| 2021/0283395 A1 | 9/2021 | Kreindel |
| 2021/0361938 A1 | 11/2021 | Gershonowitz |

FOREIGN PATENT DOCUMENTS

| | | |
|---|---|---|
| AU | 2012244313 B2 | 11/2014 |
| AU | 2014203094 B2 | 7/2015 |
| AU | 2013207657 B2 | 11/2015 |
| BR | PI0812502 A2 | 6/2015 |
| CA | 2484880 A1 | 4/2006 |
| CA | 2604112 C | 7/2016 |
| CA | 3019140 A1 | 10/2017 |
| CA | 3019410 A1 | 10/2017 |
| CA | 3023821 A1 | 11/2017 |
| CH | 714113 A2 | 3/2019 |
| CN | 86204070 U | 9/1987 |
| CN | 87203746 U | 12/1987 |
| CN | 87215926 U | 7/1988 |
| CN | 1026953 C | 12/1994 |
| CN | 1027958 C | 3/1995 |
| CN | 2192348 Y | 3/1995 |
| CN | 1206975 C | 6/2005 |
| CN | 101234231 A | 8/2008 |
| CN | 101327358 A | 12/2008 |
| CN | 201906360 U | 7/2011 |
| CN | 102319141 A | 1/2012 |
| CN | 102711706 A | 10/2012 |
| CN | 102847231 A | 1/2013 |
| CN | 202637725 U | 1/2013 |
| CN | 203169831 U | 9/2013 |
| CN | 102319141 B | 8/2014 |

(56) References Cited

FOREIGN PATENT DOCUMENTS

| | | |
|---|---|---|
| CN | 106540375 A | 3/2017 |
| CN | 107613914 A | 1/2018 |
| CN | 108882992 A | 11/2018 |
| CN | 109310516 A | 2/2019 |
| CN | 112221015 A | 1/2021 |
| DE | 718637 C | 3/1942 |
| DE | 1118902 B | 12/1961 |
| DE | 2748780 A1 | 5/1978 |
| DE | 3205048 A1 | 8/1983 |
| DE | 3340974 A1 | 5/1985 |
| DE | 3610474 A1 | 10/1986 |
| DE | 3825165 A1 | 1/1990 |
| DE | 3340974 C2 | 7/1994 |
| DE | 69318706 T2 | 1/1999 |
| DE | 10062050 A1 | 4/2002 |
| DE | 102004006192 A1 | 9/2005 |
| DE | 60033756 T2 | 6/2007 |
| DE | 102009023855 A1 | 12/2010 |
| DE | 102009050010 A1 | 5/2011 |
| DE | 102010004307 A1 | 7/2011 |
| DE | 102011014291 A1 | 9/2012 |
| DE | 102013211859 B4 | 7/2015 |
| DE | 102016116399 A1 | 3/2018 |
| DE | 202016008884 U1 | 7/2020 |
| DE | 102010014157 B4 | 2/2021 |
| DK | 0633008 T3 | 3/1999 |
| EA | 000494 B1 | 8/1999 |
| EA | 002087 B1 | 12/2001 |
| EA | 002179 B1 | 2/2002 |
| EA | 003851 B1 | 10/2003 |
| EA | 007347 B1 | 8/2006 |
| EA | 007975 B1 | 2/2007 |
| EP | 0048451 A1 | 3/1982 |
| EP | 0209246 A1 | 1/1987 |
| EP | 0459101 A1 | 12/1991 |
| EP | 0459401 A1 | 12/1991 |
| EP | 0633008 A1 | 1/1995 |
| EP | 0788813 A1 | 8/1997 |
| EP | 0633008 B1 | 5/1998 |
| EP | 0692993 B1 | 9/1999 |
| EP | 1022034 A1 | 7/2000 |
| EP | 1916013 A1 | 4/2008 |
| EP | 2069014 A2 | 6/2009 |
| EP | 2124800 B1 | 11/2010 |
| EP | 1917935 B1 | 1/2011 |
| EP | 2308559 A2 | 4/2011 |
| EP | 2139560 B1 | 5/2012 |
| EP | 2461765 A1 | 6/2012 |
| EP | 2069014 B1 | 6/2013 |
| EP | 2614807 A1 | 7/2013 |
| EP | 2676700 A2 | 12/2013 |
| EP | 2694159 A2 | 2/2014 |
| EP | 2749259 A1 | 7/2014 |
| EP | 2814445 A1 | 12/2014 |
| EP | 2856986 A1 | 4/2015 |
| EP | 3009167 A1 | 4/2016 |
| EP | 2501352 B1 | 7/2016 |
| EP | 3209246 A1 | 8/2017 |
| EP | 3342379 A1 | 7/2018 |
| EP | 3389532 A1 | 10/2018 |
| EP | 3434323 A1 | 1/2019 |
| EP | 3721939 A1 | 10/2020 |
| ES | 2118925 T3 | 10/1998 |
| ES | 2300569 T3 | 6/2008 |
| ES | 2305698 T3 | 11/2008 |
| ES | 2359581 T3 | 5/2011 |
| ES | 2533145 A2 | 4/2015 |
| ES | 2533145 B1 | 7/2016 |
| ES | 2533145 R1 | 10/2018 |
| FR | 3041881 A1 | 4/2017 |
| FR | 3061012 A1 | 6/2018 |
| GB | 260116 A | 10/1926 |
| GB | 304587 A | 3/1930 |
| GB | 390500 A | 4/1933 |
| GB | 871672 A | 6/1961 |
| GB | 2176009 A | 12/1986 |
| GB | 2188238 A | 9/1987 |
| GB | 2176009 B | 12/1989 |
| GB | 2261820 A | 6/1993 |
| GB | 2286660 A | 8/1995 |
| GB | 2395907 B | 12/2004 |
| GB | 2504984 A | 2/2014 |
| GB | 2521240 A | 6/2015 |
| GB | 2552004 A | 1/2018 |
| GR | 3027678 T3 | 11/1998 |
| IT | 1217550 B | 3/1990 |
| IT | RE20120010 A1 | 8/2013 |
| IT | UB20159823 A1 | 7/2017 |
| JP | 2003305131 A | 10/2003 |
| JP | 2006130055 A | 5/2006 |
| JP | 4178762 B2 | 11/2008 |
| JP | 4324673 B2 | 9/2009 |
| JP | 2010207268 A | 9/2010 |
| JP | 2010533054 A | 10/2010 |
| JP | 2011194176 A | 10/2011 |
| JP | 2013063285 A | 4/2013 |
| JP | 2017518857 A | 7/2017 |
| JP | 2018501927 A | 1/2018 |
| JP | 2018018650 A | 2/2018 |
| KR | 20030065126 A | 8/2003 |
| KR | 100484618 B1 | 4/2005 |
| KR | 100491988 B1 | 5/2005 |
| KR | 200407524 Y1 | 1/2006 |
| KR | 100556230 B1 | 3/2006 |
| KR | 200410065 Y1 | 3/2006 |
| KR | 100841596 B1 | 6/2008 |
| KR | 20090063618 A | 6/2009 |
| KR | 20090095143 A | 9/2009 |
| KR | 100936914 B1 | 1/2010 |
| KR | 1020100026107 A | 3/2010 |
| KR | 101022244 B1 | 3/2011 |
| KR | 20110123831 A | 11/2011 |
| KR | 20120037011 A | 4/2012 |
| KR | 101233286 B1 | 2/2013 |
| KR | 101233287 B1 | 2/2013 |
| KR | 20130072244 A | 7/2013 |
| KR | 101292289 B1 | 8/2013 |
| KR | 20130128391 A | 11/2013 |
| KR | 101413022 B1 | 7/2014 |
| KR | 101415141 B1 | 7/2014 |
| KR | 101447532 B1 | 10/2014 |
| KR | 101511444 B1 | 4/2015 |
| KR | 20150058102 A | 5/2015 |
| KR | 101539633 B1 | 7/2015 |
| KR | 20150079619 A | 7/2015 |
| KR | 20150106379 A | 9/2015 |
| KR | 101650155 B1 | 8/2016 |
| KR | 101673182 B1 | 11/2016 |
| KR | 20170090654 A | 8/2017 |
| KR | 20170107603 A | 9/2017 |
| KR | 101794269 B1 | 11/2017 |
| KR | 20180059114 A | 6/2018 |
| KR | 20180092020 A | 8/2018 |
| KR | 101941863 B1 | 1/2019 |
| KR | 20190005981 A | 1/2019 |
| KR | 102000971 B1 | 7/2019 |
| KR | 20190001779 U | 7/2019 |
| KR | 200491572 Y1 | 5/2020 |
| KR | 20200000889 U | 5/2020 |
| KR | 20200052602 A | 5/2020 |
| KR | 20200056692 A | 5/2020 |
| KR | 20200056693 A | 5/2020 |
| KR | 20200056801 A | 5/2020 |
| KR | 20200056802 A | 5/2020 |
| KR | 20200057154 A | 5/2020 |
| KR | 20210002973 A | 1/2021 |
| KR | 20210002974 A | 1/2021 |
| MX | 2012012158 A | 4/2014 |
| NL | 7510644 A | 3/1977 |
| NL | 1037451 C2 | 5/2011 |
| RU | 2212909 C2 | 9/2003 |
| RU | 2226115 C2 | 3/2004 |
| RU | 2281128 C2 | 8/2006 |
| RU | 2373971 C2 | 11/2009 |

(56) References Cited

FOREIGN PATENT DOCUMENTS

| | | |
|---|---|---|
| RU | 2392979 C2 | 6/2010 |
| RU | 2395267 C2 | 7/2010 |
| RU | 2496532 C2 | 10/2013 |
| RU | 2529471 C2 | 9/2014 |
| RU | 2596053 C2 | 8/2016 |
| RU | 2637104 C2 | 11/2017 |
| RU | 2645923 C2 | 2/2018 |
| SI | 24921 A | 8/2016 |
| TW | 200423986 A | 11/2004 |
| WO | WO-9312835 A1 | 7/1993 |
| WO | WO-9521655 A1 | 8/1995 |
| WO | WO-9527533 A1 | 10/1995 |
| WO | WO-9932191 A1 | 7/1999 |
| WO | WO-0013749 A1 | 3/2000 |
| WO | WO-0044346 A1 | 8/2000 |
| WO | WO-0107111 A2 | 2/2001 |
| WO | WO-0112089 A1 | 2/2001 |
| WO | WO-0193797 A2 | 12/2001 |
| WO | WO-0225675 A1 | 3/2002 |
| WO | WO-03078596 A2 | 9/2003 |
| WO | WO-03079916 A1 | 10/2003 |
| WO | WO-03090863 A1 | 11/2003 |
| WO | WO-03103769 A1 | 12/2003 |
| WO | WO-2004078255 A1 | 9/2004 |
| WO | WO-2004087255 A1 | 10/2004 |
| WO | WO-2004095385 A2 | 11/2004 |
| WO | WO-2004095835 A1 | 11/2004 |
| WO | WO-2004096343 A2 | 11/2004 |
| WO | WO-2004108211 A1 | 12/2004 |
| WO | WO-2005032660 A1 | 4/2005 |
| WO | WO-2005107866 A1 | 11/2005 |
| WO | WO-2006115120 A1 | 11/2006 |
| WO | WO-2007096206 A1 | 8/2007 |
| WO | WO-2007140584 A1 | 12/2007 |
| WO | WO-2008012827 A2 | 1/2008 |
| WO | WO-2008049775 A1 | 5/2008 |
| WO | WO-2008060494 A2 | 5/2008 |
| WO | WO-2008109058 A1 | 9/2008 |
| WO | WO-2008127011 A2 | 10/2008 |
| WO | WO-2008145260 A2 | 12/2008 |
| WO | WO-2009011708 A1 | 1/2009 |
| WO | WO-2009013729 A2 | 1/2009 |
| WO | WO-2009036040 A1 | 3/2009 |
| WO | WO-2009042863 A1 | 4/2009 |
| WO | WO-2009044400 A2 | 4/2009 |
| WO | WO-2009047628 A2 | 4/2009 |
| WO | WO-2009083915 A2 | 7/2009 |
| WO | WO-2010007614 A2 | 1/2010 |
| WO | WO-2010022278 A1 | 2/2010 |
| WO | WO-2010007614 A3 | 5/2010 |
| WO | WO-2010135425 A1 | 11/2010 |
| WO | WO-2010139376 A1 | 12/2010 |
| WO | WO-2011011749 A1 | 1/2011 |
| WO | WO-2011016019 A1 | 2/2011 |
| WO | WO-2011021184 A1 | 2/2011 |
| WO | WO-2011045002 A1 | 4/2011 |
| WO | WO-2011053607 A1 | 5/2011 |
| WO | WO-2011058556 A2 | 5/2011 |
| WO | WO-2011058565 A2 | 5/2011 |
| WO | WO-2011156495 A2 | 12/2011 |
| WO | WO-2012005766 A1 | 1/2012 |
| WO | WO-2012029065 A2 | 3/2012 |
| WO | WO-2012040243 A1 | 3/2012 |
| WO | WO-2012073232 A1 | 6/2012 |
| WO | WO-2012103632 A1 | 8/2012 |
| WO | WO-2012119293 A1 | 9/2012 |
| WO | WO-2012138169 A2 | 10/2012 |
| WO | WO-2013021380 A1 | 2/2013 |
| WO | WO-2013026393 A1 | 2/2013 |
| WO | WO-2013035088 A1 | 3/2013 |
| WO | WO-2013074576 A2 | 5/2013 |
| WO | WO-2013098815 A1 | 7/2013 |
| WO | WO-2013191699 A1 | 12/2013 |
| WO | WO-2014009875 A2 | 1/2014 |
| WO | WO-2014016820 A2 | 1/2014 |
| WO | WO-2014109653 A1 | 7/2014 |
| WO | WO-2014137344 A1 | 9/2014 |
| WO | WO-2014141229 A1 | 9/2014 |
| WO | WO-2014149021 A2 | 9/2014 |
| WO | WO-2014151431 A2 | 9/2014 |
| WO | WO-2014163020 A1 | 10/2014 |
| WO | WO-2014164926 A1 | 10/2014 |
| WO | WO-2015004540 A2 | 1/2015 |
| WO | WO-2015012639 A1 | 1/2015 |
| WO | WO-2015012672 A1 | 1/2015 |
| WO | WO-2015052705 A1 | 4/2015 |
| WO | WO-2015083305 A1 | 6/2015 |
| WO | WO-2015137733 A1 | 9/2015 |
| WO | WO-2015157725 A1 | 10/2015 |
| WO | WO-2015179571 A1 | 11/2015 |
| WO | WO-2016116747 A1 | 7/2016 |
| WO | WO-2016140871 A1 | 9/2016 |
| WO | WO-2017002065 A1 | 1/2017 |
| WO | WO 2017/106878 A1 | 6/2017 |
| WO | WO-2017103923 A1 | 6/2017 |
| WO | WO-2017159959 A1 | 9/2017 |
| WO | WO-2017160097 A2 | 9/2017 |
| WO | WO-2017176621 A1 | 10/2017 |
| WO | WO-2017196548 A1 | 11/2017 |
| WO | WO-2017212253 A1 | 12/2017 |
| WO | WO-2018006086 A1 | 1/2018 |
| WO | WO-2018008023 A1 | 1/2018 |
| WO | WO-2018044825 A1 | 3/2018 |
| WO | WO-2018121998 A2 | 7/2018 |
| WO | WO-2018122535 A1 | 7/2018 |
| WO | WO-2017160097 A3 | 9/2018 |
| WO | WO-2018208992 A1 | 11/2018 |
| WO | WO-2019120420 A1 | 6/2019 |
| WO | WO-2019150378 A1 | 8/2019 |
| WO | WO-2019166965 A1 | 9/2019 |
| WO | WO-2019173866 A1 | 9/2019 |
| WO | WO-2019183622 A1 | 9/2019 |
| WO | WO-2020002801 A1 | 1/2020 |
| WO | WO-2020035852 A2 | 2/2020 |
| WO | WO-2020041502 A1 | 2/2020 |
| WO | WO-2020142470 A1 | 7/2020 |
| WO | WO-2020144486 A1 | 7/2020 |
| WO | WO-2020174444 A1 | 9/2020 |
| WO | WO-2020183508 A1 | 9/2020 |
| WO | WO-2020190514 A1 | 9/2020 |
| WO | WO-2020208590 A1 | 10/2020 |
| WO | WO-2020264263 A1 | 12/2020 |
| WO | WO-2021013654 A1 | 1/2021 |
| WO | WO-2021102365 A1 | 5/2021 |

OTHER PUBLICATIONS

Lumenis Be Ltd. v. BTL Healthcare Technologies A.S., PTAB-IPR2022-00451, Declaration of Dr. Marom Bikson (EX1002), Jan. 24, 2022, 236 pages.
Lumenis Be Ltd. v. BTL Healthcare Technologies A.S., PTAB-IPR2022-00451, Pat. No. 10,806,943 Petition for Inter Partes Review, Jan. 24, 2022, 87 pages.
Lumenis Be Ltd. v. BTL Healthcare Technologies A.S., PTAB-IPR2022-00452, Declaration of Dr. Marom Bikson (EX1002), Jan. 24, 2022, 229 pages.
Lumenis Be Ltd. v. BTL Healthcare Technologies A.S., PTAB-IPR2022-00452, Pat. No. 10,806,943 Petition for Inter Partes Review, Jan. 24, 2022, 81 pages.
Operating Manual: Magstim ® 2002, P/N 3001-23-04, The Magstim Company Limited, Mar. 18, 2005, 34 pages.
Stallknecht, B., et al., "Are Blood Flow and Lipolysis in Subcutaneous Adipose Tissue Influenced by Contractions in Adject Muscles in Humans?," American Journal of Physiology. Endocrinology and Metabolism 292(2):E394-E399, American Physiological Society, United States (Feb. 2007).
Weyh, T., et al., "Marked Differences in the Thermal Characteristics of Figure-of-eight Shaped Coils Used for Repetitive Transcranial Magnetic Stimulation," Clinical Neurophysiology 116(6):1477-1486, Elsevier, Netherlands (Mar. 2005).
501(k) K030708 Slendertone Flex Letter from Department of Health and Humane Serivces, Public Health Service, Jun. 25, 2003, 6 pages.

(56) References Cited

OTHER PUBLICATIONS

501(k) K163165 AM-100 Letter from Department of Health and Human Services, Public Health Service, Feb. 16, 2017, 9 pages.
Abulhasan, J.F., et al., "Peripheral Electrical and Magnetic Stimulation to Augment Resistance Training," Journal of Functional Morphology and Kinesiology, 1(3):328-342, (Sep. 2016).
Accent Radiofrequency System, Operator's Manual, Alma Lasers, Wellbeing Through Technology, 2008, 82 Pages.
Agilent Technologies, Inc., "Agilent 33500 Series 30 MHz Function / Arbitrary Waveform Generator User's Guide," Publication No. 33520-90001 (Dec. 2010), 278 pages.
Agilent Technologies, Inc., "Agilent Announces 30 MHz Function/ Arbitrary Waveform Generators," Microwave J., URL: (Aug. 3, 2010), 8 pages.
*Allergan, Inc. et al v. BTL Healthcare Technologies A.S.*, PTAB-PGR2021-00015, Paper 16 (Decision Denying Institution of Post-Grant Review), Jun. 17, 2021, 20 pages.
*Allergan, Inc. et al v. BTL Healthcare Technologies A.S.*, PTAB-PGR2021-00016, Paper 16 (Decision Denying Institution of Post-Grant Review), Jun. 17, 2021, 20 pages.
*Allergan, Inc. et al v. BTL Healthcare Technologies A.S.*, PTAB-PGR2021-00017, Paper 16 (Decision Denying Institution of Post-Grant Review), Jun. 16, 2021, 33 pages.
*Allergan, Inc. et al v. BTL Healthcare Technologies A.S.*, PTAB-PGR2021-00018, Paper 16 (Decision Denying Institution of Post-Grant Review), Jun. 16, 2021, 42 pages.
*Allergan, Inc. et al v. BTL Healthcare Technologies A.S.*, PTAB-PGR2021-00020, Paper 16 (Decision Denying Institution of Post-Grant Review), Jun. 16, 2021, 35 pages.
*Allergan, Inc. et al v. BTL Healthcare Technologies A.S.*, PTAB-PGR2021-00021, Paper 17 (Decision Denying Institution of Post-Grant Review), Jun. 16, 2021, 33 pages.
*Allergan, Inc. et al v. BTL Healthcare Technologies A.S.*, PTAB-PGR2021-00022; PTAB-PGR2021-00023; PTAB-PGR2021-00024; PTAB-PGR2021-00025; PTAB-IPR2021-00296; PTAB-IPR2021-00312, Paper 11 (Decision Settlement Prior to Institution of Trial), Jul. 6, 2021, 4 pages.
Arjunan, P.A., et al., "Computation and Evaluation of Features of Surface Electromyogram to Identify the Force of Muscle Contraction and Muscle Fatigue," BioMed research international 2014:197960, Hindawi Pub. Co, United States (2014).
Avram, M.M and Harry, R.S.,"Cryolipolysis for Subcutaneous Fat Layer Reduction," Lasers in Surgery and Medicine, 41(10):703-708, Wiley-Liss, United States (Dec. 2009).
Bachasson, D., et al., "Quadriceps Function Assessment Using an Incremental Test and Magnetic Neurostimulation: a Reliability Study," Journal of Electromyography and Kinesiology, 23(3):649-658, Elsevier, England, (Jun. 2013).
Barker, A.T, "An Introduction to the Basic Principles of Magnetic Nerve Stimulation," Journal of Clinical Neurophysiology, 8(1):26-37, Lippincott Williams & Wilkins, United States, (Jan. 1991).
Barker, A.T., et al., "Non-Invasive Magnetic Stimulation of Human Motor Cortex," Lancet 1(8437):1106-1107, Elsevier, England (May 1985).
Barker, A.T., "The History and Basic Principles of Magnetic Nerve Stimulation," Electroencephalography and Clinical Neurophysiology 51:3-21, Elsevier, Netherlands (1999).
Barrett, J., et al., "Mechanisms of Action Underlying the Effect of Repetitive Transcranial Magnetic Stimulation on Mood: Behavioral and Brain Imaging Studies," Neuropsychopharmacology 29(6):1172-1189, Nature Publishing Group, England (Jan. 14, 2004).
Behrens, M., et al., "Repetitive Peripheral Magnetic Stimulation (15 Hz RPMS) of the Human Soleus Muscle did not Affect Spinal Excitability," Journal of Sports Science and Medicine, 10(1):39-44, Dept. of Sports Medicine, Medical Faculty of Uludag University, Turkey (Mar. 2011).
Beilin, G., et al., "Electromagnetic Fields Applied to the Reduction of Abdominal Obesity," Journal of Cosmetic & Laser Therapy, 14(1):24-42, Informa Healthcare, England, (Feb. 2012).

Belanger, A-Y., "Chapter 13: Neuromuscular Electrical Stimulation," in Therapeutic Electrophysical Agents: Evidence Behind Practice, 3rd Edition, Lupash, E., ed., pp. 220-255, Lippincott Williams & Wilkins, United States (2015).
Benton, et al., "Functional Electrical Stimulation—A Practical Clinical Guide," Second Edition, The Professional Staff Association of the Rancho Los Amigos Hospital, Inc., 42 pages (1981).
Benton, L.A., et al., "Chapter 2: Physiological Basis of Nerve and Muscle Excitation" and "Chapter 4: General Uses of Electrical Stimulation," in Functional Electrical Stimulation: A Practical Guide, 2nd Edition, pp. 11-30 and 53-71, Rancho Los Amigos Rehabilitation Engineering Center, Downey, CA (1981), 42 pages.
Bergh, U., and Ekblom, B., "Influence of Muscle Temperature on Maximal Muscle Strength and Power Output in Human Skeletal Muscles," Acta Physiologica Scandinavica 107(1):33-37, Blackwell Scientific Publications, England (Aug. 1979).
Binder-Macleod, S.A., et al., "Force Output of Cat Motor Units Stimulated with Trains of Linearly Varying Frequency," Journal of Neurophysiology 61(1):208-217, American Physiological Society, United States (Jan. 1989).
Binder-Macleod, S.A., et al., "Use of a Catchlike Property of Human Skeletal Muscle to Reduce Fatigue," Muscle & Nerve 14(9):850-857, John Wiley & Sons, United States (Sep. 1991).
Bio Medical Research Limited., "Slendertone Flex Abdominal Training System, Instructions for Use," All pages (Aug. 2006).
Bio Medical Research Limited., "Slendertone Flex Max Instruction Manual," All pages (Apr. 2006).
Bio-Medical Research Ltd., K010335, 510(k) Summary, Slendertone Flex, All pages (Sep. 2001).
Bio-Medical Research Ltd., K022855 510(k) Summary, Slendertone, 1-6 (Mar. 2003).
Bischoff, C., et al., "Repetitive Magnetic Nerve Stimulation: Technical Considerations and Clinical Use in the Assessment of Neuromuscular Transmission," Electroencephalography and Clinical Neurophysiology 93(1):15-20, Elsevier, Ireland (Feb. 1994).
Bourland, J.D., et al., "Transchest Magnetic (Eddy-Current) Stimulation of the Dog Heart," Medical & Biological Engineering & Computing 28(2):196-198, Springer, United States (Mar. 1990).
BTL Industries, Inc., K163165 510(k) Summary, AM-100, All pages (Feb. 2017).
BTL Industries, Inc., K180813 510(k) Summary, Emsculpt, All pages (Mar. 2018).
*BTL Industries, Inc. v. Allergan Ltd. et al.* DDE-1-20-cv-01046, Complaint for Patent Infringement and Exhibits 1-38, 821 pages (Aug. 2020).
*BTL Industries, Inc. v. Allergan Ltd. et al.*, DDE-1-20-cv-01046, Order Administratively Closing Case, Jul. 26, 2021, 1 page.
*BTL Industries, Inc. v. Allergan Ltd. et al* DDE-1-20-cv-01046, Order Granting Motion to Stay Pending Resolution of Proceedings at the International Trade Commission (Unopposed), 2 pages (Oct. 2020).
*BTL Industries, Inc. v. Allergan PLC et al* DDE-1-19-cv-02356, Complaint for Patent Infringement and Exhibits 1-34, 375 pages (Dec. 2019).
*BTL Industries, Inc. v. Allergan PLC et al* DDE-1-19-cv-02356, Order Granting Stipulation to Stay, Oct. 1, 2020, 1 page.
*BTL Industries, Inc. v. Allergan USA, Inc. et al.*, DDE-1-19-cv-02356, Order Administratively Closing Case, Jul. 26, 2021, 1 page.
Buenos Aires, Oct. 14, 2014, Venus Concept, Provision No. 7246, 56 pages (With Machine Translation).
Burge, S.M and Dawber, R.P.,"Hair Follicle Destruction and Regeneration in Guinea Pig Skin After Cutaneous Freeze Injury," Cryobiology, 27(2):153-163, Elsevier, Netherlands (Apr. 1990).
Busso, M. and Denkova, R., "Efficacy of High Intensity Focused Electro-Magnetic (HIFEM) Field Therapy When Used for Non-Invasive Buttocks Augmentation and Lifting: A Clinical Study" American Society for Laser Medicine and Surgery Abstracts, 382 (2018).
Bustamante, V., et al., "Muscle Training With Repetitive Magnetic Stimulation of the Quadriceps in Severe COPD Patients," Respiratory Medicine, 104(2):237-245, Elsevier, England, (Feb. 2010).

(56) References Cited

OTHER PUBLICATIONS

Bustamante, V., et al., "Redox Balance Following Magnetic Stimulation Training in the Quadriceps of Patients With Severe COPD," Free Radical Research, 42(11-12):939-948, Informa Healthcare, England, (Nov. 2008).
Callaghan, M.J., et al., "Electric Muscle Stimulation of the Quadriceps in the Treatment of Patellofemoral Pain," Archives of Physical Medicine and Rehabilitation 85(6):956-962, W.B. Saunders, United Staes (Jun. 2004).
Carbonaro, M., et al., "Architectural Changes in Superficial and Deep Compartments of the Tibialis Anterior during Electrical Stimulation over Different Sites," IEEE transactions on Neural Systems and Rehabilitation Engineering 28(11):2557-2565, IEEE, United States (Nov. 2020).
Caress, J.B., et al., "A Novel Method of Inducing Muscle Cramps Using Repetitive Magnetic Stimulation," Muscle Nerve, 23(1):126-128, John Wiley & Sons, United States, (Jan. 2000).
Certain Non-Invasive Aesthetic Body Contouring Devices, Components Thereof, and Methods of Using the Same, Inv. No. 337-TA-1219, BTL's Statement of Suggested Claim Terms to Be Construed Pursuant to Ground Rule 6b, Nov. 4, 2020, 2 pages.
Certain Non-Invasive Aesthetic Body Contouring Devices, Components Thereof, and Methods of Using the Same, Inv. No. 337-TA-1219, Complainant BTL's Proposed Construction of Disputed Claim Terms, Dec. 8, 2020, 19 pages.
Certain Non-Invasive Aesthetic Body Contouring Devices, Components Thereof, and Methods of Using the Same, Inv. No. 337-TA-1219, Complaint, Aug. 5, 2020, 93 pages.
Certain Non-Invasive Aesthetic Body Contouring Devices, Components Thereof, and Methods of Using the Same, Inv. No. 337-TA-1219, Joint Claim Construction Chart, Dec. 14, 2020, 15 pages.
Certain Non-Invasive Aesthetic Body Contouring Devices, Components Thereof, and Methods of Using the Same; Inv. No. 337-TA-1219, Joint Claim Construction Chart, Dec. 18, 2020, 15 pages.
Certain Non-Invasive Aesthetic Body Contouring Devices, Components Thereof, and Methods of Using the Same, Inv. No. 337-TA-1219, Respondents' Allergan Limited, Allergan USA, Inc., Allergan, Inc., Zeltiq Aesthetics, Inc., Zeltiq Ireland Unlimited Company, and Zimmer MedizinSysteme GmbH's Notice of Prior Art, Nov. 20, 2020, 5 pages.
Certain Non-Invasive Aesthetic Body Contouring Devices, Components Thereof, and Methods of Using the Same, Inv. No. 337-TA-1219, Respondents' List of Claim Terms for Construction, Nov. 4, 2020, 8 pages.
Certain Non-Invasive Aesthetic Body Contouring Devices, Components Thereof, and Methods of Using the Same; Inv. No. 337-TA-1219, Respondents' List of Proposed Claim Constructions and Their Intrinsic and Extrinsic Support, filed Dec. 15, 2020, 23 pages.
Certain Non-Invasive Aesthetic Body Contouring Devices, Components Thereof, and Methods of Using the Same, Inv. No. 337-TA-1219, Response of Respondent Zimmer MedizinSysteme GmbH to the Complaint and Notice of Investigation, Oct. 22, 2020, 68 pages.
Certain Non-Invasive Aesthetic Body Contouring Devices, Components Thereof, and Methods of Using the Same, Inv. No. 337-TA-1219, Response of Respondents Allergan Limited, Allergan USA, Inc., Allergan, Inc., Zeltiq Aesthetics, Inc., and Zeltiq IrelandUnlimited Company to the Complaint and Notice of Investigation, Oct. 22, 2020, 69 pages.
Certain Non-Invasive Aesthetic Body-Contouring Devices, Components Thereof, and Methods of Using Same, Notice of Institution of Investigation, Inv. No. 337-TA-1219, Notice of Institution of Investigation, Sep. 2, 2020, 21 pages.
Certain Non-Invasive Aesthetic Body-Contouring Devices, Components Thereof, and Methods of Using the Same, Inv. No. 337-TA-1219, Order No. 21 (Initial Determination), Apr. 28, 2021, 5 pages.
Certain Non-Invasive Aesthetic Body-Contouring Devices, Components Thereof, and Methods of Using the Same, Inv. No. 337-TA-1219, Order No. 30 (Order Concerning the Procedural Schedule), Aug. 4, 2021, 3 pages.
Certain Non-Invasive Aesthetic Body-Contouring Devices, Componesnts Thereof, and Methods of Using the Same, Inv. No. 337-TA-1219, Order No. 17: Amending Procedural Schedule, Apr. 9, 2021, 4 pages.
Certified English Translation of Belyaev, A.G., "Effect of Magnetic Stimulation on the Strength Capacity of Skeletal Muscles," Ph.D. Thesis Abstract, Smolensk State Academy of Physical Culture, Sport, and Tourism, Dec. 11, 2020, 23 pages.
Certified English Translation of Belyaev, A.G., "Effect of Magnetic Stimulation on the Strength Capacity of Skeletal Muscles," Ph.D. Thesis, Smolensk State Academy of Physical Culture, Sport, and Tourism, Dec. 11, 2020, 117 pages.
Chattanooga Group of Encore Medical, L.P., "Intelect SWD 100 User Manual, Operation & Installation Instructions for Intelect SWD 00-Model 1600," All pages (2009).
Chesterton, L.S., et al.,"Skin Temperature Response to Cryotherapy," Archives of Physical Medicine and Rehabilitation, 83(4):543-549, W.B. Saunders, United States (Apr. 2002).
Collins, D.F., et al., "Large Involuntary Forces Consistent With Plateau-Like Behavior of Human Motoneurons," Journal of Neuroscience 21(11):4059-4065, Society for Neuroscience, United States (Jun. 2001).
Colson, S., et al., "Re-Examination of Training Effects by Electrostimulation in the Human Elbow Musculoskeletal System," International Journal of Sports Medicine 21(4):281-288, Stuttgart, Thieme (May 2000).
Course in Physical Therapy, Presentation, Jan. 4, 2013, 156 pages.
CR Technologies, "Salus Talent Pop Manual KFDA First Approval Document" (English Translation), Nov. 25, 2011, 47 pages.
CR Technologies, "Notification of medical device manufacturing item permission, Salus Talent Pop KFDA Approval Document" (English Translation), 3 pages (Sep. 2011).
CR Technology Co, Ltd., "Salus-Talent Double Sales Brochure" 2 pages, (Oct. 2020).
CR Technology Co. Ltd., "Medical Laser Irradiator Salus-Talent-Pop User Manual Version 1.00" (Nov. 2020).
CR Technology Co. Ltd., Salus Talent Pop User Manual, Ver. 1.00, All pages, Approx. 2012.
CR Technology, Salus-Talent, Technical File of Electro-magnetic Stimulator, Document No. TF-C05, 2008, 241 pages.
CR Technology, Technology for Health and Business for Human Being, investor relations, 2008, 21 pages.
Currier, D. P., "Effects of Electrical and Electromagnetic Stimulation after Anterior Cruciate Ligament Reconstruction," The Journal of Orthopaedic and Sports Physical Therapy 17(4):177-84, Williams and Wilkins, United States (1993).
Cutera, truSculptflex, Brochure, dated 2019, 2 pages.
CynoSure, SculpSure TM, The New Shape of Energy-Based bodyContouring, 2015, Cynosure Inc, 2 pages.
Cynosure,Smooth Shapes XV, Now with Smoothshape petite, Transforming non-invasive Body Shaping,Retrieved from the Internet: (www.cynosure.com), 2011, Cynosure Inc, 8 pages.
Davies, C.T., et al., "Contractile Properties of the Human Triceps Surae With Some Observations on the Effects of Temperature and Exercise," European Journal of Applied Physiology and Occupational Physiology 49(2):255-269, Springer Verlag, Germany (Aug. 1982).
Deng, Z.D., et al., "Electric Field Depth-Focality Tradeoff in Transcranial Magnetic Stimulation: Simulation Comparison of 50 Coil Designs," Brain stimulation 6(1):1-13, Elsevier, New York (Jan. 2013).
Depatment of Health and Human Services, 501(k) Letter and Summary for K092476 Body Control System 4M Powered Muscle Stimulator, dated May 7, 2010, 5 pages.
Depatment of Health and Human Services, 501(k) Letter and Summary for K160992 HPM-6000 Powered Muscle Stimulator, dated Oct. 21, 2016, 9 pages.

(56) References Cited

OTHER PUBLICATIONS

Depatment of Health and Human Services, 501(k) Letter and Summary for K163415 SlimShape System Powered Muscle Stimulator, dated Apr. 20, 2017, 8 pages.

Depatment of Health and Human Services, 501(k) Letter and Summary for K182106 BTL 799-2T Powered Muscle Stimulator, dated Oct. 23, 2018, 9 pages.

Depatment of Health and Human Services, 501(k) Letter and Summary for K190456 BTL 799-2L Powered Muscle Stimulator, dated Jul. 5, 2019, 9 pages.

Depatment of Health and Human Services, 501(k) Letter and Summary for K192224 BTL 899 Powered Muscle Stimulator, dated Dec. 5, 2019, 11 pages.

Doucet, B., et al., "Neuromuscular Electrical Stimulation for Skeletal Muscle Function," Yale Journal of Biology & Medicine 85:201-215, Yale Journal of Biology and Medicine, United States (Jun. 2012).

Dudley, G. and Stevenson, S., "Use of Electrical Stimulation in Strength and Power Training," Special Problems in Strength and Power Training :426-435 (2003).

Duncan, D., et al., "Noninvasive Induction of Muscle Fiber Hypertrophy and Hyperplasia: Effects of High-Intensity Focused Electromagnetic Field Evaluated in an In-Vivo Porcine Model: A Pilot Study," Aesthetic Surgery Journal 40(5):568-574, Oxford University Press, United States (Apr. 2020).

DuoMAG Magnetic Stimulator, Alien Technik User Manuel, Jun. 26, 2012,48 pages, Version 2.1.

Dybek, T., et al.,"Impact of 10 Sessions of Whole Body Cryostimulation on Aerobic and Anaerobic Capacity and on Selected Blood Count Parameters," Biology of Sport, 29(1):39-43 (Jan. 2012).

Dynatronics., "Better Rehab Solutions for Better Outcomes," Rehabilitation Products Guide 2.3, 2017, 52 pages.

Effective PEMF Magnetic Fat Reduction Slimming Body Beauty Salon Machine (PEMF Star), Wolfbeauty 1980, PEMF Star, China, Retrieved from the Internet: (URL: https://www.ec21.com/product-details/Effective-PEMF-Magnetic-Fat-Reduction--8928746.html), 2019, 5 pages.

Elamed, Magnetic Therapeutic Apparatus for Running Pulse Magfield small-sized ALMAG-01 Manual, allegedly accessed on Nov. 18, 2020, All pages.

Eliminate Stubborn Fat without Surgery or Downtime and Feel Great From Every Angle, Fear No Mirror®, Consultation Guide, Coolsculpting, 2014, 20 pages.

Energist Ltd—Acquired Chromogenez—Old Account, iLipo—Laser Liposuction (i-Lipo), Video Screenshots, Aug. 10, 2009, 5 pages.

Enoka, R.M., "Muscle Strength and Its Development," Sports Medicine 6:146-168, Springer (Oct. 1988).

Epstein, C., et al., "The Oxford Handbook of Transcranial Stimulation," 773 pages (2008).

European Commission, Neuodegenerative Disorders, 10 pages printed Dec. 27, 2016.

European Commission, "Neurogenerative Disorders," 10 pages printed Dec. 27, 2016.

European Patent Office, International Search Report and Written Opinion for International Application No. PCT/IB2016/053930, dated Dec. 12, 2016, 19 pages.

Faghri, P.D., et al., "The Effects of Functional Electrical Stimulation on Shoulder Subluxation, Arm Function Recovery, and Shoulder Pain in Hemiplegic Stroke Patients," Archives of Physical Medicine and Rehabilitation 75(1):73-79, W.B. Saunders, United States (Jan. 1994).

Fischer, J., et al., "Precise Subpixel Position Measurement with Linear Interpolation of CMOS Sensor Image Data," The 6th IEEE International Conference on Intelligent Data Acquisition and Advanced Computing Systems, 500-504 (Sep. 2011).

Fisher, R., et al., "ILAE Official Report: a Practical Clinical Definition of Epilepsy," Epilepsia, 55(4):475-482, Blackwell Science, United States (Apr. 2014).

Fujimura, K., et al., "Effects of Repetitive Peripheral Magnetic Stimulation on Shoulder Subluxations Caused by Stroke: A Preliminary Study," Neuromodulation : Journal of the International Neuromodulation Society 23(6):847-851, Wiley-Blackwell, United States (Nov. 2020).

Gaines, M., "Slendertone Abdominal Training System, the First FDA-Cleared Abdominal Belt, Introduced in United States by Compex Technologies on Time for Holiday Gift-Giving," Business Wire 44199 (Oct. 2003).

Geddes, L.A., "History of Magnetic Stimulation of the Nervous System," Journal of Clinical Neurophysiology 8(1):3-9, Lippincott Williams & Wilkins, United States (Jan. 1991).

Goetz, S.M., et al., "Coil Design for Neuromuscular Magnetic Stimulation Based on a Detailed 3-D Thigh Model," IEEE Transactions on Magnetics, 50(6):10, IEEE, (Jun. 2014).

Goodman, B.E., "Channels Active in the Excitability of Nerves and Skeletal Muscles Across the Neuromuscular Junction: Basic Function and Pathophysiology," Advances in Physiology Education 32(2):127-135, American Physiological Society, United States (Jun. 2008).

Gorgey, A., et al., "Effects of Electrical Stimulation Parameters on Fatigue in Skeletal Muscle," The Journal of Orthopaedic and Sports Physical Therapy 39(9):684-692, Williams and Wilkins, United States (Sep. 2009).

Gorodnichev, R.M., et al., "The Effect of Electromagnetic Stimulation on the Parameters of Muscular Strength," Human Physiology 40:65-69 (2014).

Gorodnichev, R.M., "Magnetic Stimulation of Muscles as New Method to Enhance Their Strength," Velikie Luki State Academy of Physical Culture and Sport, Velikie Luki, 2016, 5 pages.

Halaas, Y. and Bernardy, J., "Biochemical Perspective of Fat Physiology after Application of HIFEM Field Technology: Additional Investigation of Fat Disruption Effects in a Porcine Study," American Society for Laser Medicine and Surgery Abstracts, S4 (2019).

Hamnegard, C.H., et al., "Quadriceps Strength Assessed by Magnetic Stimulation of the Femoral Nerve in Normal Subjects," Clinical Physiology and Functional Imaging, 24(5):276-280, Blackwell, England, (Sep. 2004).

Han, B.H., et al., "Development of four-channel magnetic nerve stimulator," 2001 Proceedings of the 23rd Annual EMBS International Conference, pp. 1325-1327, Turkey (2001).

Han, T.R., et al., "Magnetic Stimulation of the Quadriceps Femoris Muscle: Comparison of Pain With Electrical Stimulation," American Journal of Physical Medicine & Rehabilitation, 85(7):593-599, Lippincott Williams & Wilkins, United States, (Jul. 2006).

Harkey, M.S., "Disinhibitory Interventions and Voluntary Quadriceps Activation: A Systematic Review," Journal of Athletic Training 49(3):411-421, National Athletic Trainers' Association, United States (2014).

Heidland, A., et al., "Neuromuscular Electrostimulation Techniques: Historical Aspects and Current Possibilities in Treatment of Pain and Muscle Waisting," Clinical Nephrology 79 Suppl 1:S12-S23, Dustri-Verlag Dr. Karl Feistle, Germany (Jan. 2012).

Heisel, Jurgen, Physikalische Medizin, Stuttgart: Georg Thieme Verlag KG, 2005. ISBN 3-13-139881-7. p. 159.

Hera Estetik Medikal, "Lipostar" dated Jul. 7, 2014, accessed at https://www.youtube.com/watch?v=-R7OnFIK9go, accessed on Dec. 15, 2021.

Hera Estetik Medikal, "Lipostar Manyetik Incelme", accessed at https://www.heraestetik.com/en/urundetay/liposter-manyetik-incelme, accessed on Dec. 15, 2021.

Hill, A., "The Influence of Temperature on the Tension Developed in an Isometric Twitch," Proceeding of the Royal Society B 138:349-354, (Sep. 1951).

Hirvonen, H.E., et al.,"Effectiveness of Different Cryotherapies on Pain and Disease Activity in Active Rheumatoid Arthritis. A Randomised Single Blinded Controlled Trial," Clinical and Experimental Rheumatology, 24(3):295-301, Clinical and Experimental Rheumatology S.A. S, Italy (May-Jun. 2006).

Hovey, C. and Jalinous, R., "The Guide to Magnetic Stimulation" Magstim, Pioneers in Nerve Stimulation and Monitoring, pp. 1-44 (2016).

(56) References Cited

OTHER PUBLICATIONS

Hovey, C., et al., "The Guide to Magnetic Stimulation," The Magstim Company Limited, 48 pages (Jul. 2006).
Huang, Y.Z., et al., "Theta Burst Stimulation of the Human Motor Cortex," Neuron 45(2):201-206, Cell Press, United States (Jan. 2005).
I-Lipo by Chromo genex, i-Lipo Ultra is the Intelligent, Non-Surgical Alternative to Liposuction, 2011, 2 pages.
Increasing Physiotherapy Presence in Cosmetology, Spa Inspirations, Jan. 2012, pp. 34-35.
Irazoqui P., Post Grant Review of U.S. Pat. No. 10,695,576, PTAB-PGR2021-00024, filed as EX1085, dated Dec. 14, 2020, 25 pages.
Iskra Medical, Magneto System, 2012, 2 pages.
Iskra Medical, "Tesla Stym—Functional Magnetic Stimulation FMS," Nov. 2013, http://ww.iskramedical.eu/magneto-therapy-medical/tesla-stym, 5 pages.
Iskra Medical, "Tesla Stym Website," URL: https://web.archive.org/web/20131106123126/http:/www.iskramedical.eu:80/magneto-therapy-medical/tesla-stym (Nov. 6, 2013).
Izumiya, Y., et al., "Fast/Glycolytic Muscle Fiber Growth Reduces Fat Mass and Improves Metabolic Parameters in Obese Mice", Cell Metabolism 7(2):159-172, Cell Press, United States (Feb. 2008).
Jacob, C., et al., "High Intensity Focused Electro-Magnetic Technology (HIFEM) for Non-Invasive Buttock Lifting and Toning of Gluteal Muscles: A Multi-Center Efficacy and Safety Study," Journal of Drugs in Dermatology 17(11):1229-1232, Physicians Continuing Education Corporation, United States (Nov. 2018).
Jacob, C.I., et al., "Safety and Efficacy of a Novel High-Intensity Focused Electromagnetic Technology Device for Noninvasive Abdominal Body Shaping," Journal of Cosmetic Dermatology, 17(5):783-787, Blackwell Science, United States (Oct. 2018).
Jacobm C., and Paskova, "A Novel Non-Invasive Technology Based on Simultaneous Induction of Changes in Adipose and Muscle Tissues: Safety and Efficacy of a High Intensity Focused Electro-Magnetic (HIFEM) Field Device Used for Abdominal Body Shaping," American Society for Laser Medicine and Surgery, 2018 Electronic Posters (ePosters) Town Hall and ePosters, 369, p. 1, Wiley Periodicals, Inc. (2018).
Johari Digital Healthcare Ltd., 510(k)-K062439 Powertone Letter from Department of Health and Humane Services Summary, Public Health Service, Jan. 8, 2007, 6 pages.
Johari Digital Healthcare Ltd., "510(k)-K131291 Torc Body Letter from Department of Health and Humane Services", Public Health Service, Jun. 14, 2013, 10 pages.
Johari Digital Healthcare Ltd., K131291 510(k) Summary, TorcBody, All pages (Jun. 2013).
Jutte, L.S., et al.,"The Relationship Between Intramuscular Temperature, Skin Temperature, and Adipose Thickness During Cryotherapy and Rewarming," Archives of Physical Medicine and Rehabilitation, 82(6):845-850, W.B. Saunders, United States (Jun. 2001).
Katuscakova, Z.L., et al., High Induction Magnet Therapy in Rehabilitation, Department of Physiactric Rehabilitation, 2012, 72 pages.
Katz, B., et al., "Changes in Subcutaneous Abdominal Fat Thickness Following High-Intensity Focused Electro-Magnetic (HIFEM) Field Treatments: A Multi Center Ultrasound Study," American Society for Laser Medicine and Surgery Abstracts, 360-361 (2018).
Katz, B., et al., "Ultrasound Assessment of Subcutaneous Abdominal Fat Thickness after Treatments with a High-Intensity Focused Electromagnetic Field Device: A Multicenter Study," Dermatologic Surgery 45(12):1542-1548, Williams & Wilkins, United States (Dec. 2019).
Kavanagh, S., et al., "Use of a Neuromuscular Electrical Stimulation Device for Facial Muscle Toning: A Randomized, Controlled Trial," Journal of Cosmetic Dermatology 11(4):261-266, Blackwell Science, United States (Dec. 2012).
Kent, D., and Jacob C., "Computed Tomography (CT) Based Evidence of Simultaneous Changes in Human Adipose and Muscle Tissues Following a High Intensity Focused Electro-Magnetic Field (HIFEM) Application: A New Method for Non-Invasive Body Sculpting," American Society for Laser Medicine and Surgery Abstracts, p. 370 (2018).
Kent, D,E. and Jacob, C.I., Simultaneous Changes in Abdominal Adipose and Muscle Tissues Following Treatments by High-Intensity Focused Electromagnetic HIFEM Technology-Based Device: Computed Tomography Evaluation, Journal of Drugs in Dermatology 18(11):1098-1102, Physicians Continuing Education Corporation, United States (Nov. 2019).
Kim, Y.H., et al.,"The Effect of Cold Air Application on Intra-Articular and Skin Temperatures in the Knee," Yonsei Medical Journal, 43(5):621-626, Yonsei University, Korea (South) (Oct. 2002).
Kinney, B.M. and Lozanova P., "High Intensity Focused Electromagnetic Therapy Evaluated by Magnetic Resonance Imaging: Safety and Efficacy Study of a Dual Tissue Effect Based Non-Invasive Abdominal Body Shaping," Lasers in Surgery and Medicine 51(1):40-46, Wiley-Liss, United States (Jan. 2019).
Kocbach et al., "A Simulation Approach to Optimizing Perfermance of Equipment for Thermostimulation of Muscle Tissue using COMSOL Multiphysics" Article in Biophysics & Bioeng. dated 2011, 26 pages.
Kolin, A., et al., "Stimulation of Irritable Tissues by means of an Alternating Magnetic Field," Proceedings of the Society for Experimental Biology and Medicine 102:251-253, Blackwell Science, United States (Oct. 1959).
Korman, P., et al.,"Temperature Changes in Rheumatoid Hand Treated With Nitrogen Vapors and Cold Air," Rheumatology International, 32(10):2987-2992, Springer International, Germany (Oct. 2012).
Kotz, Y., "Theory and Practice of Physical Culture," Training of Skeletal Muscle With Method of Electrostimulation, 64-67 (Mar. 1971).
Kotz, Y., "Theory and Practice of Physical Culture," Training of Skeletal Muscle With Method of Electrostimulation, 66-72 (Apr. 1971).
Krueger, N. et al., "Safety and Efficacy of a New Device Combining Radiofrequency and Low-Frequency Pulsed Electromagnetic Fields for the Treatment of Facial Rhytides," Journal of Drugs in Dermatology 11(11):1306-1309, Physicians Continuing Education Corporation, United States (Nov. 2012).
Kumar, N. and Agnihotri, R.C., "Effect of Frequency and Amplitude of Fes Pulses on Muscle Fatigue During Toning of Muscles," Journal of Scientific and Industrial Research 67(4):288-290, (Apr. 2008).
Lampropoulou, S.I., et al., "Magnetic Versus Electrical Stimulation in the Interpolation Twitch Technique of Elbow Flexors," Journal of Sports Science and Medicine, 11(4):709-718, Dept. of Sports Medicine, Medical Faculty of Uludag University, Turkey (Dec. 2012).
Langford, J. and Mccarthy, P.W., "Randomised controlled clinical trial of magnet use in chronic low back pain; a pilot study," Clinical Chiropractic 8(1):13-19, Elsevier (Mar. 2005).
Lee, P.B., et al., "Efficacy of Pulsed Electromagnetic Therapy for Chronic Lower Back Pain: a Randomized, Double-blind, Placebcontrolled Study," The Journal of International Medical Research 34(2):160-167, Cambridge Medical Publications, England (Mar.-Apr. 2006).
Leitch, M., et al., "Intramuscular Stimulation of Tibialis Anterior in Human Subjects: The Effects of Discharge Variability on Force Production and Fatigue," Physiological Reports 5(15):e13326, Wiley Periodicals, Inc., United States (Aug. 2017).
Leon-Salas, W.D., et al., "A Dual Mode Pulsed Electro-Magnetic Cell Stimulator Produces Acceleration of Myogenic Differentiation," Recent Patents on Biotechnology 7(1):71-81, Bentham Science Publishers, United Arab Emirates (Apr. 2013).
Letter from Department of Health and Human Services, Public Health Service, Dec. 19, 2014, 7 pages.
Lin, V.W., et al., "Functional Magnetic Stimulation: A New Modality for Enhancing Systemic Fibrinolysis," Archives of Physical Medicine and Rehabilitation 80(5):545-550, W.B. Saunders, United States (May 1999).

(56) References Cited

OTHER PUBLICATIONS

Lin, V.W., et al., "Functional Magnetic Stimulation for Conditioning of Expiratory Muscles in Patients with Spinal Cord Injury.," Archives of Physical medicine and Rehabilitation 82(2):162-166, W.B. Saunders, United States (Feb. 2001).

Lin, V.W., et al., "Functional Magnetic Stimulation for Restoring Cough in Patients With Tetraplegia," Archives of Physical Medicine and Rehabilitation, 79(5):517-522, W.B. Saunders, United States, (May 1998).

Lin, V.W., et al., "Functional Magnetic Stimulation of Expiratory Muscles: a Noninvasive and New Method for Restoring Cough," Journal of Applied Physiology (1985), 84(4):1144-1150, American Physiological Society, United States, (Apr. 1998).

Lin, V.W., et al., "Functional Magnetic Stimulation of the Respiratory Muscles in Dogs," Muscle & Nerve 21(8):1048-1057, John Wiley & Sons, United States (Aug. 1998).

Linehan, C., et al., Brainwave the Irish EpilepsyAssoication, "The Prevalence of Epilepsy in Ireland" Summary Report,pp. 1-8 (May 2009).

Lotz, B.P., et al., "Preferential Activation of Muscle Fibers with Peripheral Magnetic Stimulation of the Limb," Muscle & Nerve, 12(8):636-639, John Wiley & Sons, United States (Aug. 1989).

*Lumenis Be Ltd.* v. *BTL Healthcare Technologies A.S.*, PTAB-IPR2021-01402, Declaration of Dr. Marom Bikson (EX1002), Sep. 13, 2021, 244 pages.

*Lumenis Be Ltd.* v. *BTL Healthcare Technologies A.S.*, PTAB-IPR2021-01402, U.S. Pat. No. 10,821,295 Petition for Inter Partes Review, Sep. 13, 2021, 81 pages.

*Lumenis Be Ltd.* v. *BTL Healthcare Technologies A.S.*, PTAB-IPR2021-01403, Declaration of Dr. Marom Bikson (EX1002), Sep. 13, 2021, 243 pages.

*Lumenis Be Ltd.* v. *BTL Healthcare Technologies A.S.*, PTAB-IPR2021-01403, U.S. Pat. No. 10,821,295 Petition for Inter Partes Review, Sep. 13, 2021, 84 pages.

*Lumenis Be Ltd.* v. *BTL Healthcare Technologies A.S.*, PTAB-IPR2021-01404, Declaration of Dr. Marom Bikson (EX1002), Sep. 13, 2021, 245 pages.

*Lumenis Be Ltd.* v. *BTL Healthcare Technologies A.S.*, PTAB-IPR2021-01404, U.S. Pat. No. 10,124,187 Petition for Inter Partes Review, Sep. 13, 2021, 82 pages.

*Lumenis Be Ltd.* v. *BTL Healthcare Technologies A.S.*, PTAB-IPR2021-01405, Declaration of Dr. Marom Bikson (EX1002), Sep. 13, 2021, 247 pages.

*Lumenis Be Ltd.* v. *BTL Healthcare Technologies A.S.*, PTAB-IPR2021-01405, U.S. Pat. No. 10,124,187 Petition for Inter Partes Review, Sep. 13, 2021, 86 pages.

*Lumenis Ltd.* v. *BTL Healthcare Technologies A.S.*, PTAB-IPR2021-01273, Declaration of Dr. Marom Bikson (EX1002), Aug. 13, 2021, 225 pages.

*Lumenis Ltd.* v. *BTL Healthcare Technologies A.S.*, PTAB-IPR2021-01273, U.S. Pat. No. 10,478,634, Petition for Inter Partes Review, Aug. 13, 2021, 70 pages.

*Lumenis Ltd.* v. *BTL Healthcare Technologies A.S.*, PTAB-IPR2021-01275, Declaration of Dr. Marom Bikson (EX1002), Aug. 5, 2021, 282 pages.

*Lumenis Ltd.* v. *BTL Healthcare Technologies A.S.*, PTAB-IPR2021-01275, U.S. Pat. No. 10,632,321, Petition for Inter Partes Review, Aug. 5, 2021, 92 pages.

*Lumenis Ltd.* v. *BTL Healthcare Technologies A.S.*, PTAB-IPR2021-01276, Declaration of Dr. Marom Bikson (EX1002), Aug. 5, 2021, 241 pages.

*Lumenis Ltd.* v. *BTL Healthcare Technologies A.S.*, PTAB-IPR2021-01276, U.S. Pat. No. 10,965,575, Petition for Inter Partes Review, Aug. 5, 2021, 79 pages.

*Lumenis Ltd.* v. *BTL Healthcare Technologies A.S.*, PTAB-IPR2021-01278, Declaration of Dr. Marom Bikson (EX1002), Aug. 13, 2021, 255 pages.

*Lumenis Ltd.* v. *BTL Healthcare Technologies A.S.*, PTAB-IPR2021-01278, U.S. Pat. No. 10,709,894, Petition for Inter Partes Review, Aug. 13, 2021, 85 pages.

*Lumenis Ltd.* v. *BTL Healthcare Technologies A.S.*, PTAB-IPR2021-01279, Declaration of Dr. Marom Bikson (EX1002), Aug. 5, 2021, 258 pages.

*Lumenis Ltd.* v. *BTL Healthcare Technologies A.S.*, PTAB-IPR2021-01279, U.S. Pat. No. 10,709,895, Petition for Inter Partes Review, Aug. 5, 2021, 88 pages.

*Lumenis Ltd.* v. *BTL Healthcare Technologies A.S.*, PTAB-IPR2021-01280, Declaration of Dr. Marom Bikson (EX1002), Aug. 13, 2021, 235 pages.

*Lumenis Ltd.* v. *BTL Healthcare Technologies A.S.*, PTAB-IPR2021-01280, U.S. Pat. No. 10,478,634, Petition for Inter Partes Review, Aug. 13, 2021, 69 pages.

*Lumenis Ltd.* v. *BTL Healthcare Technologies A.S.*, PTAB-IPR2021-01282, Declaration of Dr. Marom Bikson (EX1002), Aug. 5, 2021, 267 pages.

*Lumenis Ltd.* v. *BTL Healthcare Technologies A.S.*, PTAB-IPR2021-01282, U.S. Pat. No. 10,632,321, Petition for Inter Partes Review, Aug. 5, 2021, 89 pages.

*Lumenis Ltd.* v. *BTL Healthcare Technologies A.S.*, PTAB-IPR2021-01283, Declaration of Dr. Marom Bikson (EX1002), Aug. 5, 2021, 241 pages.

*Lumenis Ltd.* v. *BTL Healthcare Technologies A.S.*, PTAB-IPR2021-01283, U.S. Pat. No. 10,695,575, Petition for Inter Partes Review, Aug. 5, 2021, 84 pages.

*Lumenis Ltd.* v. *BTL Healthcare Technologies A.S.*, PTAB-IPR2021-01284, Declaration of Dr. Marom Bikson (EX1002), Aug. 5, 2021, 279 pages.

*Lumenis Ltd.* v. *BTL Healthcare Technologies A.S.*, PTAB-IPR2021-01284, U.S. Pat. No. 10,709,895, Petition for Inter Partes Review, Aug. 5, 2021, 93 pages.

*Lumenis Ltd.* v. *BTL Healthcare Technologies A.S.*, PTAB-IPR2021-01285, Declaration of Dr. Marom Bikson (EX1002), Aug. 13, 2021, 249 pages.

*Lumenis Ltd.* v. *BTL Healthcare Technologies A.S.*, PTAB-IPR2021-01285, U.S. Pat. No. 10,709,894, Petition for Inter Partes Review, Aug. 13, 2021, 79 pages.

Madariaga, V.B., et al., "[Magnetic Stimulation of the Quadriceps: Analysis of 2 Stimulators Used for Diagnostic and Therapeutic Applications]," Archives De Bronconeumología, 43(7):411-417, Elsevier Espana, Spain, (Jul. 2007).

Maffiuletti, N.A., et al., "Activation of Human Plantar Flexor Muscles Increases After Electromyostimulation Training," Journal of Applied Physiology 92(4):1383-1392, American Physiological Society, United States (Nov. 2001).

Maffiuletti, N.A., et al., "The Effects of Electromyostimulation Training and Basketball Practice on Muscle Strength and Jumping Ability," International journal of sports medicine 21(6):437-443, Thieme, Germany (Aug. 2000).

Mag Venture, Magnetic Stimulation, Accessories Catalogue, Accessories Catalogue, 2011, 54 pages.

Magstim Company Limited, K051864 510(k) Summary, Magstim Rapid and Magstim Super Rapid, All pages (Dec. 2005).

Magstim Company US, LLC, K060847 510(k) Summary, Magstim Model 200-2 with Double 70mm Remote Coil, All pages (Sep. 2006).

Magstim Corporation US, K992911 510(k) Summary, Magstim Rapid, All pages (Jan. 2000).

MagVenture, MagPro® by MagVenture®, Versatility in Magnetic Stimulation, World Leading Transcranial Magnetic Stimulation Systems, 2011, 6 Pages.

Man, W.D-C., et al., "Magnetic Stimulation for the Measurement of Respiratory and Skeletal Muscle Function," The European Respiratory Journal 24(5):846-60, European Respiratory Society, England (2004).

Manstein, D., et al.,"Selective Cryolysis: A Novel Method of Non-Invasive Fat Removal," Lasers in Surgery and Medicine, 40(9):595-604, Wiley-Liss, United States (Nov. 2008).

Mantovani, A., et al., "Applications of Transcranial Magnetic Stimulation to Therapy in Pyschiatry," Psychiatric Times 21(9), Intellisphere, 29 pages (Aug. 2004).

Marek Heinfarth, "Lipostar" dated Jan. 9, 2013, accessed at https://www.youtube.com/watch?v=hZurkn8iU_U, accessed on Dec. 15, 2021.

(56) References Cited

OTHER PUBLICATIONS

Markov, M.S., "Pulsed Electromagnetic Field Therapy History, State of the Art and Future," Environment Systems and Decisions 27(4):465-475, Springer (Dec. 2007).
MecoTec Freezing Technology, Presentation Cryoair Whole Body Cryotherapy Chambers, Germany, Jul. 2017, 52 Pages.
Medline, Body Temperature Norms, 2 pages (Year: 2019).
Mekawy et al., "Influence of Electro-lipolysis on Lipid Profile and Central Obesity in Obese Premenopausal Women" Bull. Fac. Ph. Th. Cairo Univ., vol. 17, No. (1), dated Jan. 2012, pp. 59-68.
Mettler J.A., et al., "Low-Frequency Electrical Stimulation With Variable Intensity Preserves Torque," Journal of Electromyography and Kinesiology : Official Journal of the International Society of Electrophysiological Kinesiology 42:49-56, Oxford:Elsevier, England (Oct. 2018).
Mogyoros, I., et al., "Strength-Duration Properties of Human Peripheral Nerve," Brain 119(Pt 2):439-447, Oxford University Press, England (Apr. 1996).
Morrissey. M., "Electromyostimulation from a Clinical Perspective," Sports Medicine 6(1):29-41, Springer International, New Zealand (Aug. 1988).
Mustafa, B., "Design and Construction of a Low Cost dsPIC Controller Based Repetitive Transcranial Magnetic Stimulator TMS," Journal of medical systems 34(1):15-24, Kluwer Academic/Plenum Publishers, United States (2010).
Nadler, S.F., et al.,"The Physiologic Basis and Clinical Applications of Cryotherapy and Thermotherapy for the Pain Practitioner," Pain Physician, 7(3):395-399, American Society of Interventional Pain Physicians, United States (Jul. 2004).
Nassab, R.,"The Evidence Behind Noninvasive Body Contouring Devices," Aesthetic Surgery Journal, 35(3):279-293, Oxford University Press, England (Mar. 2015).
National Institute of Neurological Disorders and Stroke, Epilepsy Information Page, www.ninds.nih.gov/disorders/epilepsy/epilepsy. htm, pp. 1-6 (Feb. 1, 2016).
Neotonus, Inc., K973096 510(k) Summary, Neotonus Model 1000 Muscle Stimulator System, All pages (Jun. 1998).
Neotonus, Inc., K973929 510(k) Summary and FDA Correspondence, Neotonus, All pages (May 1998).
Neuro Star , TMS Therapy, Bringing Hope to Patients with Depression, 2013, 6 Pages.
Neurosoft, Ivanovo, Since 1992, Magnetic Stimulator, NEURO-MS, Technical Manual, Neurosoft Ltd, Ivanovo, Russia, 2006, 67 Pages.
Nexstim NBS System, Navigated Brain Stimulation, Noninvasive, direct cortical mapping, 2012, 5 Pages.
Neyroud, D., et al., "Comparison of Electrical Nerve Stimulation, Electrical Muscle Stimulation and Magnetic Nerve Stimulation to Assess the Neuromuscular Function of the Plantar Flexor Muscles," European journal of applied physiology 115(7):1429-1439, Springer-Verlag, Germany (2015).
Nielsen, J.F., et al., "A New High-frequency Magnetic Stimulator With an Oil-cooled Coil," Journal of Clinical Neurophysiology 12(5):460-467, Lippincott Williams & Wilkins, United States (Sep. 1995).
Non Final Office Action dated Jun. 23, 2017, in U.S. Appl. No. 15/473,390, Schwarz, T., et al., filed Mar. 29, 2017.
Notice of Allowance dated May 6, 2020 for U.S. Appl. No. 16/194,800 (pp. 1-8).
Notice of Allowance dated Oct. 8, 2019 for U.S. Appl. No. 15/603,162 (pp. 1-8).
Novickij, V., et al., "Compact Microsecond Pulsed Magnetic Field Generator for Application in Bioelectronics," Elektronika ir Elektrotechnika 19(8):25-28 (Oct. 2013).
Novickij, V., et al., "Design and Optimization of Pulsed Magnetic Field Generator for Cell Magneto-Permeabilization," Elektronika ir Elektrotechnika(Electronics and Electrical Engineering) 23(2):21-25 (Apr. 2017).

Novickij, V., et al., "Magneto-Permeabilization of Viable Cell Membrane Using High Pulsed Magnetic Field," IEEE Transactions on Magnetics 51(9), All pages (Sep. 2015).
Novickij, V., et al., "Programmable Pulsed Magnetic Field System for Biological Applications," IEEE Transactions on Magnetics 50(11):5 (Nov. 2014).
NPF Electroapparat, Amplipulse-5Br Manual, allegedly accessed on Nov. 18, 2020, All pages.
Nuerosoft Ltd., "Neurosoft—Neuro-MS Transcranial Magnetic Simulator Technical Manual," All pages (Nov. 2014).
Obsluze, N.K.,Usage Instructions, User's Manual, Device for high-induction magnetic stimulation of type designation:Saluter Moti, 2016,88 Pages.
Office Action dated Aug. 15, 2019 for U.S. Appl. No. 16/194,800 (pp. 1-12).
Office Action dated Jul. 10, 2020 for U.S. Appl. No. 15/678,915 (pp. 1-9).
Office Action dated Oct. 7, 2019 for U.S. Appl. No. 15/678,915 (pp. 1-8).
Oliveira, P.DE., et al., "Neuromuscular Fatigue After Low- and Medium-frequency Electrical Stimulation in Healthy Adults," Muscle & Nerve 58(2):293-299, John Wiley & Sons, United States (Aug. 2018).
Operating Manual: Magstim $D70^2$ Coil, MOP06-EN, Revision 01, The Magstim Company Limited, Feb. 2012, 14 Pages.
Operating Manual: Magstim Magstim $200^2$, MOP01-EN, Revision 01, The Magstim Company Limited, Sep. 2011, 25 Pages.
Operating Manual: Magstim, Magstim Alpha Coil Range, MOP11-EN, Revision 01, Oct. 2012, 18 Pages.
Operating Manual: Magstim, Magstim $Bistim^2$, MOP02-EN, Revision, The Magstim Company Limited, 01, Sep. 2011, 27 Pages.
Operating Manual, Magstim, Model 200, P/N 3001-01, Double 70mm, Remote Coil, P/N 3190-00, The Magstim Company Limited, 2006, 32 pages.
Operating Manual: Magstim R, 2nd, Generation Coil Family, 3100-23-02, Magstim Coils, The Magstim Company Limited, Nov. 2002, 14 Pages.
Operating Manual, Magstim R Air-Cooled Double 70mm Coil System, 1600-23-04, The Magstim Company Limited, 1999, 18 Pages.
Operating Manual: Magstim R, Bistim System, P/N 3234-23-01, The Magstim Company Limited, Nov. 2004, 30 Pages.
Operating Manual: Magstim R, Coils & Accessories, 1623-23-07, Magstim Coils & Accessories, May 2010, 24 Pages.
Operating Manual: Magstim, RAPID2, P/N 3576-23-09, The Magstim Company Ltd, Nov. 2009, 61 Pages.
Operator's Manual: BTL Emsculpt, BTL Industries Ltd, United Kingdom, 2018, 35 pages.
Operator's Manual: BTL, HPM-6000U, BTL Industries Ltd, United Kingdom, Dec. 2016, 36 pages.
Otte, J.S., et al.,"Subcutaneous Adipose Tissue Thickness Alters Cooling Time During Cryotherapy," Archives of Physical Medicine and Rehabilitation, 83(11):1501-1505, W.B. Saunders, United States (Nov. 2002).
Pain Management Technologies, "Pain Management Technologies Product Catalog," (2012).
Papimi, For Scientific Research, Pap Ion Magnetic Inductor, Presentation, Magnetotherapeutic Device, Nov. 2009, 61 Pages.
Periso SA, CTU mega Diamagnetic Pump 20: Device for Diamagnetic Therapy, CTU Mega 20 Manual, dated Aug. 28, 2019, 44 pages, Pazzallo Switzerland.
Photograph, Alleged Photograph of Components of a Salus Talent Pop Double Device with an Alleged Manufacture date of Nov. 14, 2012, 1 page.
Physiomed, MAG-Expert, Physiomed Manual, Dec. 19, 2012.
Platil, A., "Magnetopneumography Using Optical Position Reference," Sensor Letters 11(1):69-73, ResearchGate (2013).
Podebradsky.K., et al., Clinical study of high-inductive electromagnetic stimulator Salus talent, 2010, 8 pages.
Pohanka, J., et al., "An Embedded Stereovision System: Aspects of Measurement Precision," 12th Biennial Baltic Electronics Conference, pp. 157-160 (Oct. 2010).

(56) References Cited

OTHER PUBLICATIONS

Polk, C., "Therapeutic Applications of Low-Frequency Sinusoidal and Pulsed Electric and Magnetic Fields," The Biomedical Engineering Handbook, vol. 1, 2000, Second edition, CRC Press LLC, pp. 1625-1636.

Polkey M.I., et al., "Functional Magnetic Stimulation of the Abdominal Muscles in Humans," American Journal of Respiratory and Critical Care Medicine 160(2):513-522, American Thoracic Society, United States (Aug. 1999).

Polkey, M.I., et al., "Quadriceps Strength and Fatigue Assessed by Magnetic Stimulation of the Femoral Nerve in Man," Muscle Nerve 19(5):549-555, John Wiley & Sons, United States, (May 1996).

Pollogen, Maximus Non-invasive body shaping System, User Manual, dated May 1, 2012, 44 pages.

Pollogen, TriFractional FAQs, User Manual, dated Aug. 2011, 4 pages.

Pollogen, TriLipo MED Procedure, Brochure, dated Apr. 7, 2021, 76 pages.

Porcari, J.P., et al., "Effects of Electrical Muscle Stimulation on Body Composition, Muscle Strength, and Physical Appearance," Journal of Strength and Conditioning Reasearch 16(2):165-172, Human Kinetics Pub., United States (May 2002).

Porcari, J.P., et al., "The Effects of Neuromuscular Electrical Stimulation Training on Abdominal Strength, Endurance, and Selected Anthropometric Measures," Journal of Sports Science and Medicine 4(1):66-75, Dept. of Sports Medicine, Turkey (Mar. 2005).

Pribula, O. and Fischer, J., "Real Time Precise Position Measurement Based on Low-Cost CMOS Image Sensor," IEEE, 5 pages (2011).

Pribula, O., et al., "cost-effective Image Acquisition System for Precise Pc-based Measurements," Przeglad Elektrotechniczny (Electrical Review), 259-263, 2011.

Pribula, O., et al., "Optical Position Sensor Based on Digital Image Processing: Magnetic Field Mapping Improvement," Radioengineering 20 (1):55-60, (Apr. 2011).

Pribula, O., et al., "Real-Time Video Sequences Matching Spatio-Temporal Fingerprint," IEEE, 911-916 (Jun. 2010).

Prouza, O., et al., "High-Intensity Electromagnetic Stimulation Can Reduce Spasticity in Post-Stroke Patients," International Journal of Physiotherapy 5(3):87-91 (2018).

Prouza, O., "Ex-Post Analyza Spot Rebnich Dani," All pages, (2008).

Prouza, O., "Targeted Radiofrequency Therapy for Training Induced Muscle Fatigue—Effective or Not?," International Journal of Physiotherapy 3(6):707-710 (Dec. 2016).

PTAB-IPR2021-00296, U.S. Pat. No. 10,493,293, Petition for Inter Partes Review, Dec. 14, 2020, 117 pages.

PTAB-IPR2021-00312, U.S. Pat. No. 10,478,634, Petition for Inter Partes Review, Dec. 14, 2020, 108 pages.

PTAB-PGR2021-00015, U.S. Pat. No. 10,709,895, Petition for Post-Grant Review, Dec. 14, 2020, 140 pages.

PTAB-PGR2021-00016, U.S. Pat. No. 10,709,895, Petition for Post-Grant Review, Dec. 14, 2020, 144 pages.

PTAB-PGR2021-00017, U.S. Pat. No. 10,632,321, Petition for Post-Grant Review, Dec. 14, 2020, 121 pages.

PTAB-PGR2021-00018, U.S. Pat. No. 10,632,321, Petition for Post-Grant Review, Dec. 14, 2020, 140 pages.

PTAB-PGR2021-00020, U.S. Pat. No. 10,695,575, Petition for Post-Grant Review, Dec. 14, 2020, 112 pages.

PTAB-PGR2021-00021, U.S. Pat. No. 10,695,575, Petition for Post-Grant Review, Dec. 14, 2020, 117 pages.

PTAB-PGR2021-00022, U.S. Pat. No. 10,709,894, Petition for Post-Grant Review, Dec. 14, 2020, 119 pages.

PTAB-PGR2021-00023, U.S. Pat. No. 10,709,894, Petition for Post-Grant Review, Dec. 14, 2020, 136 pages.

PTAB-PGR2021-00024, U.S. Pat. No. 10,695,576, Petition for Post-Grant Review, Dec. 14, 2020, 136 pages.

PTAB-PGR2021-00025, U.S. Pat. No. 10,695,576, Petition for Post-Grant Review, Dec. 14, 2020, 135 pages.

Publication of Medical Device Manufacturing Approval of Salus-Talent-Pro, approval date Mar. 11, 2014, 39 pages.

Quick Start Manuals, Magstim Super Rapid Plus Quick Start, Aalto TMS Laboratory, Aalto School of Science, 2013, 7 Pages.

Radakovic T. and Radakovic N., "The Effectiveness of the Functional Magnetic Stimulation Therapy in Treating Sciatica Syndrome," Open Journal of Therapy and Rehabilitation 3(3):63-69 (2015).

Reshaping the Future of Your Practice, Cool sculpting, A Revolution in Aesthetic Fat Reduction, 2011, 10 Pages.

Riehl., M., "Chapter 3: TMS Stimulator Design" The Oxford Handbook of Transcranial Stimulation, Wasserman, E.M., ed., pp. 13-23, Oxford University Press, 26 pages, United Kingdom (2008).

Roots, H., and Ranatunga, K.W., "An Analysis of the Temperature Dependence of Force, During Steady Shortening at Different Velocities, in (Mammalian) Fast Muscle Fibres," Journal of Muscle Research and Cell Motility 29(1):9-24, Springer, Netherlands (Jun. 2008).

Ruiz-Esparza, J. and J. Barba Gomez., "The Medical Face Lift: A Noninvasive, Nonsurgical Approach to Tissue Tightening in Facial Skin Using Nonablative Radiofrequency," Dermatologic Surgery 29(4):325-332, Williams & Wilkins, United States (Apr. 2003).

Russian excerpt of Werner, R., Magnetotherapy, Pulsating energy resonance therapy, 41-67 (Jun. 2007).

Rutkove, S., "Effects of Temperature on Neuromuscular Electrophysiology," Muscle & Nerve 24(7):867-882, John Wiley & Sons, United States (Jul. 2001).

Salus Talent Pop, The first sales bill, Authorization No. 20120221-41000096-66667961, 2 pages, (Feb. 2012).

Salus Talent-A, Remed, User Guide, High Intensity Electro Magnetic Field Therapy, 2017, 37 pages.

Sargeant, A.J., "Effect of Muscle Temperature on Leg Extension Force and Short-term Power Output in Humans," European Journal of Applied Physiology and Occupational Physiology 56(6):693-698, Springer Verlag, Germany (Sep. 1987).

Schaefer, D.J., et al., "Review of Patient Safety in Time-Varying Gradient Fields," Journal of Magnetic Resonance Imaging 12:20-29, Wiley-Liss, United States (Jul. 2000).

Shimada, Y., et al., "Effects of therapeutic magnetic stimulation on acute muscle atrophy in rats after hindlimb suspension," Biomedical Research 27(1):23-27, Biomedical Research Foundation, Japan (Feb. 2006).

Silinskas, V., et al., "Effect of Electrical Myostimulation on the Function of Lower Leg Muscles," Journal of strength and Conditioning Research 31(6):1577-1584, Human Kinetics Pub, United States (2017).

Sport-Elec S.A., K061914 510(k) Summary, Sport-Elec, All pages (Jul. 2007).

Sport-Elec S.A., K081026 510(k) Summary, Sport-Elec, All pages (Nov. 2008).

Starbelle, PEMF Shape, Webpage, dated Feb. 10, 2020, 3 pages, available at http://www.starbelle.cn/info/PEMFShape.html.

Stedman, T.L., "Aponeurosis—Apparatus," in Stedman's Medical Dictionary, 27th Edition, Pugh, M.B., ed., pp. 113-114, Lippincott Williams & Wilkins, Baltimore, MD (2000).

Stevens, J.E., et al., "Neuromuscular Electrical Stimulation for Quadriceps Muscle Strengthening After Bilateral Total Knee Arthroplasty: A Case Series," Journal of Orthopaedic and Sports Physical Therapy 34(1):21-29, Williams and Wilkins, United States (Jan. 2004).

Struppler, A., et al., "Facilitation of Skilled Finger Movements by Repetitive Peripheral Magnetic Stimulation (RPMS)—A New Approach in Central Paresis.," NeuroRehabilitation 18(1):69-82, IOS Press, Amsterdam (2003).

Struppler, A., et al., "Modulatory Effect of Repetitive Peripheral Magnetic Stimulation on Skeletal Muscle Tone in Healthy Subjects: Stabilization of the Elbow Joint," Experimental Brain Research 157(1):59-66, Springer Verlag, Germany (Feb. 2004).

Suarez-Bagnasco, D., et al., "The Excitation Functional for Magnetic Stimulation of Fibers.," Annual International Conference of the IEEE Engineering in Medicine and Biology Society, IEEE Engineering in Medicine and Biology Society, Annual International Conference, 2010:4829-4833, IEEE, United States (2010).

(56) References Cited

OTHER PUBLICATIONS

Swallow, E.B., et al., "A Novel Technique for Nonvolitional Assessment of Quadriceps Muscle Endurance in Humans," Journal of Applied Physiology 103(3):739-746, American Physiological Society, United States (Sep. 2007).

Szecsi, J., et al., "A Comparison of Functional Electrical and Magnetic Stimulation for Propelled Cycling of Paretic Patients," Archives of Physical Medicine and Rehabilitation 90(4):564-570, W.B. Saunders, United States, (Apr. 2009).

Szecsi, J., et al., "Force-pain Relationship in Functional Magnetic and Electrical Stimulation of Subjects With Paresis and Preserved Sensation," Clinical Neurophysiology 121(9):1589-1597, Elsevier, Netherlands, (Sep. 2010).

Taylor, J.L, "Magnetic Muscle Stimulation Produces Fatigue Without Effort," Journal of Applied Physiology (1985) 103(3):733-734, American Physiological Society, United States, (Sep. 2007).

Tesla Stym, Iskra Medical, Tone the inner muscle with FMS Functional Magnetic Stimulation, 2013, 4 pages.

The Burn Centre Care, Education, 3 pages, printed from internet Nov. 13, 2017.

The Magstim Company Ltd, K080499 510(k) Summary, Magstim Double 70mm Air Film Coil, All pages (Dec. 2008).

The Magstim Company Ltd., K130403 510(k) Summary, Magstim D702 coil, All pages (Aug. 2013).

Thermi Launches Arvati, powered by Thermi, with newest advances in True Temperature Controlled Radiofrequency Technology, 5 pages (2018).

Thompson, M.T., "Inductance Calculation Techniques—Part II: Approxmiations and Handbook Methods," Power Control and Intelligent Motion, 11 pages (Dec. 1999) http://www.pcim.com/.

Thompson, M.T., "Inductance Calculation Techniques—Part II: Classical Methods," Power Control and Intelligent Motion, 25(12):40-45, (Dec. 1999) http://www.pcim.com/.

Tomek, J., et al., "Magnetopneumography—Incorporation of optical position reference," Journal of Electrical Engineering, All pages (2012).

Torbergsen, T., "Abstracts of the International Course and Symposium in Single Fibre EMG and Quantitative EMG Analysis. Tromsø, Norway, Jun. 4-8, 1984," Muscle & Nerve 9(6):562-574, John Wiley & Sons, United States (Jul.-Aug. 1986).

TriLipo MED Procedure, http://download.lifvation.com/Maximus_TriLipoMED_Intro.pdf, Apr. 2013, 66 pages.

TSEM Med Swiss SA, Diamagnetic Therapy: A Revolutionary Therapy, CTU Mega 20 Catalogue, dated 2016, 24 pages, Lugano Switzerland.

Turley, J., "Agilent Technologies Announces 30 MHz Function/Arbitrary Waveform Generators with Unparalleled Signal Accuracy," Elec. Eng'g J., URL: (Aug. 4, 2010), 8 pages.

Ultra Slim Professional, The very best body Contouring, Wardphotonics LLC, 2018, 16 pages.

U.S. Appl. No. 60/848,720, inventor Burnett, D., filed Sep. 30, 2006 (Not Published).

U.S. Appl. No. 62/331,060, inventor Schwarz, T., filed May 3, 2016 (Not Published).

U.S. Appl. No. 62/331,072, inventor Schwarz, T., filed May 3, 2016 (Not Published).

U.S. Appl. No. 62/331,088, inventor Schwarz, T., filed May 3, 2016 (Not Published).

U.S. Appl. No. 62/333,666, inventor Schwarz, T., filed May 9, 2016 (Not Published).

U.S. Appl. No. 62/351,156, inventor Schwarz, T., filed Jun. 16, 2016 (Not Published).

U.S. Appl. No. 62/357,679, inventor Schwarz, T., filed Jul. 1, 2016 (Not Published).

U.S. Appl. No. 62/440,905, inventors Schwarz, T. et al., filed Dec. 30, 2016 (Not Published).

U.S. Appl. No. 62/440,912, inventors Schwarz, T. et al., filed Dec. 30, 2016 (Not Published).

U.S. Appl. No. 62/440,922, inventor Schwarz, T., filed Dec. 30, 2016 (Not Published).

U.S. Appl. No. 62/440,936, inventor Schwarz, T., filed Dec. 30, 2016 (Not Published).

U.S. Appl. No. 62/440,940, inventor Schwarz, T., filed Dec. 30, 2016 (Not Published).

U.S. Appl. No. 62/441,805, inventor Prouza, O., filed Jan. 3, 2017 (Not Published).

User Guide: Mag Venture, Magpro family, MagPro R30, MagPro R30 with MagOption, MagPro X100, MagPro X100 with MagOption, MagPro software v.5.0, US-edition, MagPro family User Guide, 2010, 52 Pages.

User Guide, Salus Talent Pro, Remed, High Intensity Electro magnetic Field Therapy-2 Channel, 2017, Version M-1.0.0, 45 pages.

User Guide, Salus Talent, Remed, High Intensity Electro magnetic Field Therapy, Version. M-1.0.0, 2017, 40 pages.

User's Manual: BTL-6000, Super Inductive System Elite, BBTL Industries Ltd, United Kingdom, Sep. 2016, 36 pages.

User Manual: Electro-magnetic Stimulator, Salus-Talent, Version 1.00, Rehabilitation Medical Company,2013, 34 Pages.

User Manual: Regenetron PRO, System Information, Regenetron PRO User Manual, Nov. 2014, 7 Pages.

Vance, C., et al., "Effects of Transcutaneous Electrical Nerve Stimulation on Pain, Pain Sensitivity, and Function in People with Knee Osteoarthritis," Physical Therapy 92:898-910 (2012).

Venus Concept Ltd., VenusFreeze MP2, User Manual, dated Jun. 2012, 46 pages.

Venus Concept Ltd., VenusViva, User Manual, dated Aug. 2013, 51 pages.

Verges S., et al., "Comparison of Electrical and Magnetic Stimulations to Assess Quadriceps Muscle Function," Journal of Applied Physiology (1985) 106(2):701-710, American Physiological Society, United States, (Feb. 2009).

Wada, K., et al., "Design and Implementation of Multi-Frequency Magnetic Field Generator Producing Sinusoidal Current Waveform for Biological Researches," IEEE, 9 pages (2016).

Wanitphakdeedecha, R., et al., "Treatment of Abdominal Cellulite and Circumference Reduction With Radiofrequency and Dynamic Muscle Activation" Article in Journal of Cosmetic and Laser Therapy, dated Apr. 6, 2015, 7 pages.

Ward, A.R. and Shkuratova, N., "Russian Electrical Stimulation: The Early Experiments," Physical therapy 82(10):1019-1030, Oxford University Press, United States (2002).

Wasilewski, M.L., Academy of Aesthetic and Anti-Aging Medicine, Application of magnetic fields with deep stimulation in the fight against local obesity of lower limbs, BTL, 2012, 4 pages.

Web MD, what is normal body temperature? 3 pages, printed Mar. 4, 2019.

Weight to volume aluminum, 2 pages. printed from internet Sep. 25, 2018.

Weight to volume copper, 2 pages printed from internet Sep. 25, 2018.

Weiss, R.A., et al., "Induction of Fat Apoptosis by a Non-Thermal Device: Mechanism of Action of Non-Invasive High-Intensity Electromagnetic Technology in a Porcine Model," Lasers in surgery and medicine 51(1):47-53, Wiley-Liss, United States (Jan. 2019).

Weng, O., "Electromagnetic Activation of the Calf Muscle Pump," UMI Dissertation Publishing (2014).

Woehrle, J., et al., "Dry Needling and its Use in Health Care—A Treatment Modality and Adjunct for Pain Management," Journal of Pain & Relief 4(5):1-3, (Aug. 2015).

Yacyshy, A.F., et al., "The Inclusion of Interstimulus Interval Variability Does Not Mitigate Electrically-evoked Fatigue of the Knee Extensors," European Journal of Applied Physiology 120(12):2649-2656, Springer-Verlag, Germany (Sep. 2020).

ZAO OKB RITM, Electroneurostimulants, Transdermal Scenar-NT Instructions, All Pages (Nov. 2013).

ZAO OKB RITM, Percutaneous Electrical Stimulators With Individual Biofeedback Dosing Impact on Reflex Zones, All pages (2017).

Zelickson, B., et al.,"Cryolipolysis for Noninvasive Fat Cell Destruction: Initial Results From a Pig Model," Dermatologic Surgery 35(10):1462-1470, Hagerstown, MD Lippincott, Williams & Wilkins, United States (Oct. 2009).

(56) References Cited

OTHER PUBLICATIONS

Zerona R-Z6 by Erchonia, Specifications, Retrieved from the Internet: (www.myzerona.com), 2015, 1 page.

Zhang, G., et al., "A Method of Nerve Electrical Stimulation by Magnetic Induction," Annual International Conference of the IEEE Engineering in Medicine and Biology Society 2009:622-625, IEEE, United States (2009).

Zhi-De, D., "Electromagnetic Field Modeling of Transcranial Electric and Magnetic Stimulation: Targeting, Individualization, and Safety of Convulsive and Subconvulsive Applications," Academic Commons (2013).

Zhu, Y., et al., "Magnetic Stimulation of Muscle Evokes Cerebral Potentials by Direct Activation of Nerve Afferents: A Study During Muscle Paralysis," Muscle & Nerve 19(12):1570-1575, John Wiley & Sons, United Sates (Dec. 1996).

Mantis, The non-invasive solution that restores natural beauty, improves health, and offers a renewed psychophysical sense of balance, MR991 theramagnetic, 2020, 8 pages.

Mantis Theramagnetic Compact: the compact that guarantees utmost efficiency and maximum performance, theramagnetic, 2020, 8 pages.

Pollegen, K200545, Legend Pro DMA, Indications for use, dated Oct. 20, 2021, 11 pages.

Notice of Allowance dated Jul. 21, 2021 for U.S. Appl. No. 17/087,850 (pp. 1-8).

Notice of Allowance dated Mar. 24, 2021 for U.S. Appl. No. 17/087,850 (pp. 1-8).

Office Action dated Jun. 28, 2021 for U.S. Appl. No. 16/727,458 (pp. 1-11).

2018 Cutera University, Clinical Forum, Cutera 20, 26 pages.

Alma Lasers., "Accent Radiofrequency System, Operator's Manual," Wellbeing Through Technology, 2008, Chapters 1-8, Appendix A.

U.S. Appl. No. 62/786,731, inventor Schwarz, T., filed Dec. 31, 2018 (Not Published).

Pascual-Leone, Alvaro et al. "Handbook of Transcranial Magnetic Stimulation" 2002 Arnold Publishers, Chapters 1-4, 58 pages.

\* cited by examiner

SYSTEMS AND METHODS FOR TREATMENT OF A PATIENT INCLUDING RF AND ELECTRICAL ENERGY

CROSS-REFERENCE TO RELATED APPLICATIONS

This Application is a continuation of U.S. patent application Ser. No. 17/098,638, filed Nov. 16, 2020, which claims priority to U.S. Provisional Patent Application No. 63/019,619, filed May 4, 2020, and is a continuation-in-part of U.S. patent application Ser. No. 16/194,800, filed Nov. 19, 2018, which claims priority to U.S. Provisional Patent Application No. 62/587,716, filed Nov. 17, 2017, and is a continuation-in-part of U.S. patent application Ser. No. 15/584,747 filed May 2, 2017, now issued as U.S. Pat. No. 10,195,453 on Feb. 5, 2019, which claims priority to U.S. Provisional Patent Application Nos. 62/333,666, filed May 9, 2016; 62/331,060, filed May 3, 2016; 62/331,088, filed May 3, 2016; 62/331,072, filed May 3, 2016; 62/351,156, filed Jun. 16, 2016; 62/358,417, filed Jul. 5, 2016; 62/375,796, filed Aug. 16, 2016; and 62/340,398, filed May 23, 2016. All the listed applications are incorporated herein by reference in their entireties.

FIELD OF THE INVENTION

This invention relates to noninvasive, aesthetic, automated radio-frequency (RF) treatment devices and methods for treating soft tissue using an RF electrode and a vacuum system.

BACKGROUND OF THE INVENTION

Soft tissue includes skin, muscle, fat, connective tissue (e.g. collagen fibers), nervous tissue (e.g. neurons, motor neuron and neuromuscular junction), cartilage, veins, artery, body fluids (e.g. blood, lymph and/or other body liquids) and other soft structures.

Human skin is composed of three basic elements: the epidermis, the dermis and the hypodermis or so called sub cutis. The dermis consists of collagen, elastic tissue and reticular fibers. The hypodermis is the lowest layer (structure) of skin and contains hair follicle roots, lymphatic vessels, collagen tissue, nerves and also subcutaneous fat forming an adipose tissue.

Adipose tissue is formed by aggregation mostly of adipose cells mostly containing stored fats as triglycerides. Triglycerides are esters of three fatty acid chains and the alcohol glycerol (fat). Most adipose tissue accumulations result from fat primarily from food, when energy intake derived from food exceeds daily energy needs. This may result in an increase in fat cell size or fat cell number or both. Mature fat cells are very large, ranging up to 40 microns in diameter and containing as much as 95% lipid (fat) by volume. The subcutaneous adipose tissue layer may be thin (about 1 cm or less) in humans of slight or moderate body type. It is possible to distinguish different types of adipose tissue. Adipose tissue may mean visceral (fat) adipose tissue located adjacent to internal organs, subcutaneous adipose tissue located beneath the skin but above skeletal muscle and/or adipose tissue located between the muscle fibers.

Excess adipose tissue may be perceived as aesthetically undesirable. Excess adipose tissue may lead to health complications.

Dieting and exercise may result in reduction of adipose tissue and weight loss. However, the reduction in adipose tissue volume occurs rather unpredictably from all anatomical areas. This can leave the areas intended for reduction (e.g. the abdomen) largely unaffected, even after significant body weight loss. Dieting and exercise may also cause discomfort, physical and psychic stress. Various invasive and non-invasive methods have been developed to remove unwanted subcutaneous fat from specific areas of the body.

The main invasive method is surgical-assisted liposuction, where selected volumes of adipose tissue are mechanically aspirated out of the patient at desired anatomical sites of the body. However, liposuction procedures are invasive and can be painful and traumatic, with many undesirable side effects and risks. Lipodissolve is another invasive procedure involving a series of drug injections intended to dissolve and permanently remove small pockets of fat from various parts of the body. It is also known as mesotherapy, lipozap, lipotherapy or injection lipolysis. Lipodissolve has many disadvantages and risks also, to the extent that various medical associations have issued health warnings against using it.

The non-invasive methods concentrate on the acceleration of the lipolysis as the natural process of the fat reduction. This can be achieved in several ways. One of them is application of pharmaceuticals accelerating the lipolysis. However, when applied topically they tend only to affect the outermost layers of the skin, rarely penetrating to the sub dermal vascular plexus. Another method uses radio frequency or ultrasound energy focused on adipose tissue to cause cell destruction and cell death. These methods tend to damage the melanocyte in the epidermis. The hyper thermic temperatures destroy the target tissues and leave the body to remove the dead cellular and other debris. Non-invasive heating techniques have also been used. These non-invasive methods have certain disadvantages as well (e.g. inhomogeneous soft tissue heating, creating of hot spots, panniculitis etc.), and have been used with varying degrees of success.

Accordingly, there is need for improved methods and systems for subcutaneous treatments. There is also a need to improve the energy flow through the tissue of treated patient to reduce or eliminate risks of overheating of non-target soft tissue, improve homogeneity of heating desired layer of soft tissue in order to prevent hot spots. Heating of soft tissue by an external source of energy may cause other undesired effect and health complications e.g. non-controlled heating or overheating of the soft tissue that is also needed to improve.

SUMMARY OF THE INVENTION

Apparatus and methods provide RF (radio-frequency) treatment with applied negative pressure (pressure lower than atmospheric pressure).

Parameters of the soft tissue may greatly influence transfer of a (radio-frequency) treatment RF energy into the soft tissue and a treatment result. Parameters of the soft tissue which may be influenced include e.g. polarity of the soft tissue, dielectric constant, specific heat capacity, coefficient of thermal diffusion and/or other parameters of the soft tissue may be influenced. Factors that may influence parameters of the soft tissue may include e.g.: temperature, body liquids flow and/or other mechanisms; in the treated soft tissue. Varying of RF signal parameters may enhance RF signal penetration and/or targeting to specific soft tissue structure in order to achieve desired treatment results. RF signal parameters include, for example, frequency, polarization of RF waves, ratio between magnetic and electric component of RF waves, output power, pulse intensity, pulse duration, sequence of pulses, shape of pulses, envelope of provided signal, duration of continual radiation, distance between the electrode, orientation of the electrode, surface of the electrode, shape of the electrode, shape of electromagnetic field, homogeneity of electromagnetic field, flux density of provided RF energy and/or others. Enhancing of treatment results may be also provided combination of RF signal of one frequency with RF signal of different frequency and/or by combination of treatment RF energy with another type of treatment energy like e.g. light, magnetic field, electric current, plasma, heating/cooling, mechanical waves (ultrasound, shock wave . . . ) and/or any type of massage. RF treatment result may be also improved by medication to patient before, during and/or after treatment session.

Knowing the dielectric constant (mainly its complex part) of specific soft tissue structure may be important when providing treatment using an electromagnetic field e.g. RF energy. The dielectric constant behaves as a parameter with real and imaginary parts that depend on several physical quantities. The dielectric constant of specific soft tissue structure may depend on the frequency of the RF signal, the ratio between electric and magnetic components of the RF signal, the direction of spreading of the RF wave, the temperature of the environment where RF wave spreading occurs, distance and/or other factors.

The electromagnetic energy may be ionizing energy (e.g. gamma radiation and/or X-rays), light (e.g. ultraviolet, visible and/or infrared light), terahertz energy, microwave energy and/or radiofrequency energy. Electromagnetic energy may include coherent and/or non-coherent energy.

Tissue with a low complex dielectric constant is heated more quickly than a tissue with a high complex dielectric constant during capacitive RF energy transfer in frequency ranges up to 0.5 MHz or more preferably up to 10 MHz. For example, bone tissue and adipose tissue have a low dielectric constant in comparison to muscle. Absorbed power of adipose tissue ($P_a$) and muscle tissue ($P_m$) is different. The ratio ($P_a/P_m$) is large, as a consequence of relatively small conductivity ratio ($\delta a/\delta m$) and dominantly a large permittivity ratio ($|\varepsilon_m*I^2/I\varepsilon_a*I^2$), such that a relatively large absorption occurs in the adipose tissue.

Increasing temperature in the soft tissue may have other positive effects. Hyperthermia may be used in order to vary physical parameters of the soft tissue, to improve regeneration of injured muscles, cartilage, other soft tissue deficiencies, to improve blood flow, lymph flow, remove degeneration caused by aging, or excrescent of adipose.

The apparatus may provide heating of the soft tissue by thermal diffusion from an applicator to the patient's body and/or heat by delivered one or more other treatment energy sources e.g.: the dielectric loss RF treatment energy by an RF treatment energy source.

Changing temperature of the soft tissue before, during and/or after the treatment may influence pain receptors, soft tissue laxity, dielectric properties of soft tissue, improve homogeneity of distributed energy delivered to the soft tissue by the treatment energy source (e.g. prevent hot spots), stimulate fat metabolism, prevent edge effects, and/or create temperature differences in the soft tissue. A temperature of the soft tissue target area during the treatment may be selectively adjusted with or without changing temperature of adjacent areas, in order to improve comfort and/or effectiveness of the treatment.

Various aesthetic skin and/or body treatment effects may be provided by the present methods and devices including: anti-aging (e.g.: wrinkle reduction, skin tightening, hydrating the skin, skin rejuvenation, skin viability, removing of pigment deficiencies and/or pigmentation correction); skin disease (e.g.: rashes, lupus, fungal diseases, surface antimicrobial treatment procedure, hypothermia, hyperemia); soft tissue relaxation (e.g.: muscle and/or other soft tissue layers relaxation); body shaping (e.g.: fat removing, removing of unwanted soft tissue laxity, removing of cellulite, building muscle mass and strength, accelerating fat metabolism of a cells, restructuring of the connective tissue; increase in the number of fibroblasts, enhancement of fibroblast proliferation, by neocolagenesis and/or elastogenesis); and/or other soft tissue deficiencies (e.g.: by accelerating body metabolism, stimulating the lymphatic circulation), circumferential reduction influence membrane transport of a cell, a proliferation of chondrocytes in the cartilages, increase in blood perfusion, blood flow and venous return, wound healing, disinfection of the patient surface and/or relieving of a patient's body pain).

The light therapy devices and methods of the present invention may be used for physical treatment of various tissue problems, including but not limited to Achilles tendonitis, ankle distortion, anterior tibial syndrome, arthritis of the hand, arthrosis, bursitits, carpal tunnel syndrome, cervical pain, dorsalgia, epicondylitis, facial nerve paralysis, herpes labialis, hip joint arthrosis, impingement syndrome, frozen shoulders, knee arthrosis, knee distortion, lumbosacral pain, muscle relaxation, nerve repair, onychomycosis, Osgood-Schlatter syndrome, pain relief, painful shoulders, patellar tendinopathy, plantar fasciitis, heel spurs, tarsal tunnel syndrome, tendinopagny, or tendovaginitis. Other applications may include treatment of open wounds, dry eyes and general treatment of the eye.

Some embodiments of devices and methods of the present invention may also be used for aesthetic and cosmetic methods coupled to tissue problems, e.g. hair epilation and/or depilation, hair removal, hair regrowth stimulation, reduction of adipose tissue, hyperhidrosis, cellulite treatment, elastin remodeling, elimination of stratum corneum, collagen remodeling, acne treatment, skin rejuvenation, skin tightening, wrinkle removal, stretch mark removal, tattoo removal, teeth whitening, treatment of tooth decay, treatment of rhinitis, or circumferential reduction. Embodiments of the present invention may be also used to treat vulvar laxity and/or hemorrhoids. Some embodiments are also capable of at least partial removal of rosacea, dermatitis, eczema, café au lait spots, apthous stomatitis, halitosis, birthmarks, port-wine stains, pigment stains, skin tumors, scar treatment, or scar elimination. Some embodiments of the present invention may also be used for general surgery, dentistry, stomatology, or body modification, e.g. scarification.

Treated parts of a human body may in some embodiments include, but are not limited to, the face, neck, nose, mouth, arms, hands, torso, back, love handles, abdomen, limbs, legs, head, buttocks, feet and/or thighs.

Predefined treatment therapy methods may be manually performed by an operator and/or automatically performed by a controlling mechanism (e.g. control unit) or changed during the treatment based on feedback parameters, based on the treatment protocol and/or based on previous treatment or measurement. Multiple treatment energy sources may be combined to provide a synergic effect on human tissue. This improves effectiveness of the treatment and/or reduces time needed for the treatment. It may also improve safety of the treatment e.g. stimulation of soft tissue by massage improves blood and lymph stimulation which in combination with an RF field provides improves removal of treated fat cells (prevention of panniculitis), improves homogeneity of delivered energy in to the soft tissue, targeting of delivered energy to the soft tissue, reduces pain during the therapy and/or a decreases the influence of edge effects and overheating of a part of the soft tissue due to enhanced body liquid circulation.

Another example of synergic effects may be utilization of plasma (e.g. non-thermal plasma), where an RF electrode may regulate plasma, help to create plasma and/or adjust some parameters of plasma. Several treatments in combination may provide better transfer of the energy to a specific layer of the soft tissue; e.g. preheating, massage of the patient skin surface to accelerate blood flow that increases the complex dielectric constant of the surface and increases penetration of such layer by RF waves.

The apparatus may operate without any operator which saves time and reduces costs of the treatment. The apparatus may automatically control parameters of treatment energy and/or other parameters of the device associated with treatment. One operator may supervise more than one treated patient. Self-operated devices may prevent mistakes during the treatment caused by human factors. A self-operated device may also have a better response to changed conditions of the treatment and/or may provide more homogenous and precise treatment which improves results and safety of the treatment. A computer may have a better response to changed conditions because it can react faster than 0.001 s, whereas human response on occurrences like moving of the patient, or structural changes in the soft tissue is at least 0.5 s. Another benefit of self-operated devices may be that the operator does not have to be as skilled as when using manual device.

The applicator may be adjacent to a patient surface and it may be flexible and of arbitrary size and shape. This characteristic helps to provide optimal energy transfer from an applicator to the patient soft tissue. More perfect contact with the patient surface may decrease or prevent the edge effect backscattering of delivered energy (which may improve focusing of the delivered energy) and/or provides optimal conditions for collecting feedback information. Direct contact with the patient surface may also be used for accurate and fast regulation of patient surface temperature.

According to this document, diabetes symptoms include a blood glucose value above the normal limit.

Glossary

It is to be understood that the figures and descriptions of the present invention have been simplified to illustrate elements that are relevant for a clear understanding of the present invention, while eliminating, for the purpose of clarity, many other elements found in related systems and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Soft tissue structure or specific soft tissue part is a part of the soft tissue that exhibits the same or nearly the same physical parameters and/or structural characteristic (e.g. water content, content and structure of collagen, protein content, stiffness etc). Examples of different specific soft tissue structures are: collagen fibers, veins, adipose tissue, keratinocytes in epidermis, nerves, muscle, cartilage and/or other soft tissue structures.

Treatment protocol is a software protocol that defines treatment parameters, guides treatment process of one or more treatment energy sources and defines parameters of provided treatment energy. At least part of the treatment protocol may be preprogramed in a control unit, other controlling mechanism with CPU, or may be used from an external device (e.g.: downloaded from a network or recorded from an external device). Treatment protocol may be design, selected and/or adjusted by an operator and/or by software in a control unit, external device and/or by other controlling mechanism based on feedback information and/or previous experience. Two or more treatment protocols or at least part of two or more treatment protocols may be combined together and create new one treatment protocol.

An external device is a device including hardware and software provided separately from the treatment device. An external device may be e.g.: a computer, smartphone, tablet, USB flash disc, or other equivalent device. The external device communicates with a control unit and/or may communicate with other controlling mechanisms.

A treatment energy source is a hardware part of the device that may provide treatment energy in order to provide treatment effects.

Active surface of the applicator is area providing treatment therapy and/or more therapies.

A treatment pattern creates pattern by switching between applicators and/or treatment elements providing one or more types of the therapy across the patient surface. A treatment pattern may include different types of switching sequences, and also include at least one of: a specific treatment therapy is applied; a selection of applicators and/or treatment elements applying specific treatments; timing of the applied therapy; the distance between at least two applicators; duration of the treatment therapy applied; body location where the treatment therapy applied; cycle of applying one or more specific treatment therapies.

A treatment pattern may provide information about applying one or more types of the treatment therapies and their manner (e.g.: simultaneous, sequential and/or applying of one or more treatment therapies with some overlay). A treatment pattern may simulate moving of the one or more applicators guided by an operator by switching between applicators and/or treatment elements of one or more applicators and/or one or more treatment therapies. Simulated moves may be circular, zig-zag, spiral, other geometrical pattern, scanning and/or other pattern that may be created by moving the applicator guided by operator. A treatment pattern may also be used for scanning of the patient soft tissue.

A hardware pattern is a composition of the device and placement of the parts of the device. A hardware pattern also includes placement of the applicators which is in some embodiments not limited (e.g.: in the supporting matrix, on the patient surface etc.), placement of the treatment unit, and/or other devices adjacent/at working distance to the soft tissue (which includes direct, indirect or no contact).

Treatment energy is energy provided to the patient's body in order to cause treatment effects. Treatment energy provided by the device may be focused or unfocused, selective or non-selective. Applied treatment energy may be: RF, light, electric current, plasma, continual and/or time varying magnetic field, mechanical wave e.g. like acoustic wave (including ultrasound), shock wave, mechanical friction of patient's skin surface, heating, cooling, or applied pressure to the patient soft tissue.

In this document RF signal, RF waves and/or RF energy are in relation with radiofrequency field produced by RF treatment energy source.

Treatment effect is an effect caused by treatment energy in the patient's body. Treatment effect may also be influenced and/or caused by applied active substances described below. Treatment effect causes intended metabolic and/or structural changes in the patient's soft tissue and/or cells. Treatment energy may be targeted to cause treatment effect in a bone tissue. The device may provide treatment effects: treating and/or suppressing diabetes symptoms, wrinkle reduction, skin tightening, hydration of the skin, skin rejuvenation, skin viability, removing of pigment deficiencies, slowing of soft tissue aging process, treating of rashes, treating of lupus, treating of fungal diseases, surface antimicrobial treatment procedure, hypothermia, hyperemia, soft tissue relaxation e.g.: muscle, sinew and/or other soft tissue layers relaxation; body shaping e.g.: adipose cell volume downsizing, adipose cell removing, removing of unwanted soft tissue laxity, removing of cellulite, building muscle mass and strength, accelerating fat metabolism of a cells, restructuring of the connective tissue; increase in the number of fibroblasts, enhancement of fibroblast proliferation, neocollagenesis and/or elastogenesis; acceleration of body metabolism, stimulation of blood and lymphatic circulation, circumferential reduction influence membrane transport of a cell, a proliferation of chondrocytes in the cartilages, increase in blood perfusion, blood flow and venous return, wound healing, restore nerve functionality, influence cell proliferation, disinfection of the patient surface and/or relieving of a patient body pain, enhancing of bone density.

Treatment parameters may be any parameters influencing the treatment of the patient. Treatment parameters mainly determine type and parameters of the treatment energy. The term "treatment parameters" refers to the configuration parameters of a treatment device of the present invention, including but not limited to value of applied pressure, switching on/off sequence of specific treatment energy source or sources, the energy output, treatment duration, energy spot size and shape, scanning speed, direction of the movement of the energy spot, the treatment pattern, the wavelength or wavelengths of the energy, the frequency of provided energy, the distance between the subject tissue and the scanning unit or source of energy, target area or part of the soft tissue, pulse duration, pulse sequence, frequency of delivered energy by treatment energy source, amount of delivered radiation, energy flux density, duration of delivered treatment energy, timing of applied treatment energies, temperature value of the soft tissue and/or part of the device, focusing parameters of delivered treatment energy as focal spot volume, depth, electric voltage on the treatment energy source, intensity of provided magnetic field and/or other parameters, distance e.g. between treatment energy source and patient's skin surface (epidermis) and/or other parameters.

A shape adaptive material adapts its shape and volume as influenced by external forces An elastic material adapts its shape but not volume. The elastic material may stretch or deform to adapt to external forces.

Target area/tissue is part of the soft tissue targeted by focused or unfocused treatment energy to provide treatment effect.

Discomfort temperature is the temperature of at least part of the patient's soft tissue that becomes painful and/or highly uncomfortable according the patient's subjective feeling.

Comfortable temperature is the temperature of at least part of the patient's soft tissue that is tolerable for the patient according subjective patient's filling, treatment protocol and/or feedback information from specific sensors.

Bolus is a special embodiment of dielectric material with a cavity inside located between patient surface and the treatment source of energy. The cavity of the bolus may be filled with fluid that may be any type of gas, liquid, gel, suspension and/or mixture. Fluid may also flow through the bolus and may regulate its temperature and/or dielectric parameters.

RF electrode or electrode in this text has the same meaning. RF electrode is treatment energy source that may provide RF treatment energy or electrotherapy.

Contact part of the applicator is lower part of the applicator located in proximity to treatment area. According one embodiment described below contact part of the applicator may be dielectric material which is in direct contact with the patient's skin surface (e.g. see part 401a FIG. 4) or surface of the treatment energy source. Vacuum edge is not considered as contact part of the applicator.

The term "proximity" refers to direct contact and/or spaced by air gap and/or any other material with a dielectric constant higher than 1 (e.g. a gel layer).

RF signal and RF energy have the same meaning in this text.

The term "tissue problems" refers to any tissue problem that might benefit from the treatments of the present invention, including but not limited to an open wound, excess hair, excess adipose tissue, wrinkles, sagging skin, excess sweat, scars, acne, stretch marks, tattoos, biofilms of bacteria, viruses, enlargement, rosacea, dermatitis, eczema, café au lait spots, calcium deposits, birthmarks, port-wine stains, pigment stains, skin tumors, apthous stomatitis, halitosis, herpes simplex, ulcers or other skin diseases classified by the WHO.

DETAILED DESCRIPTION OF THE INVENTION

Figure 1:
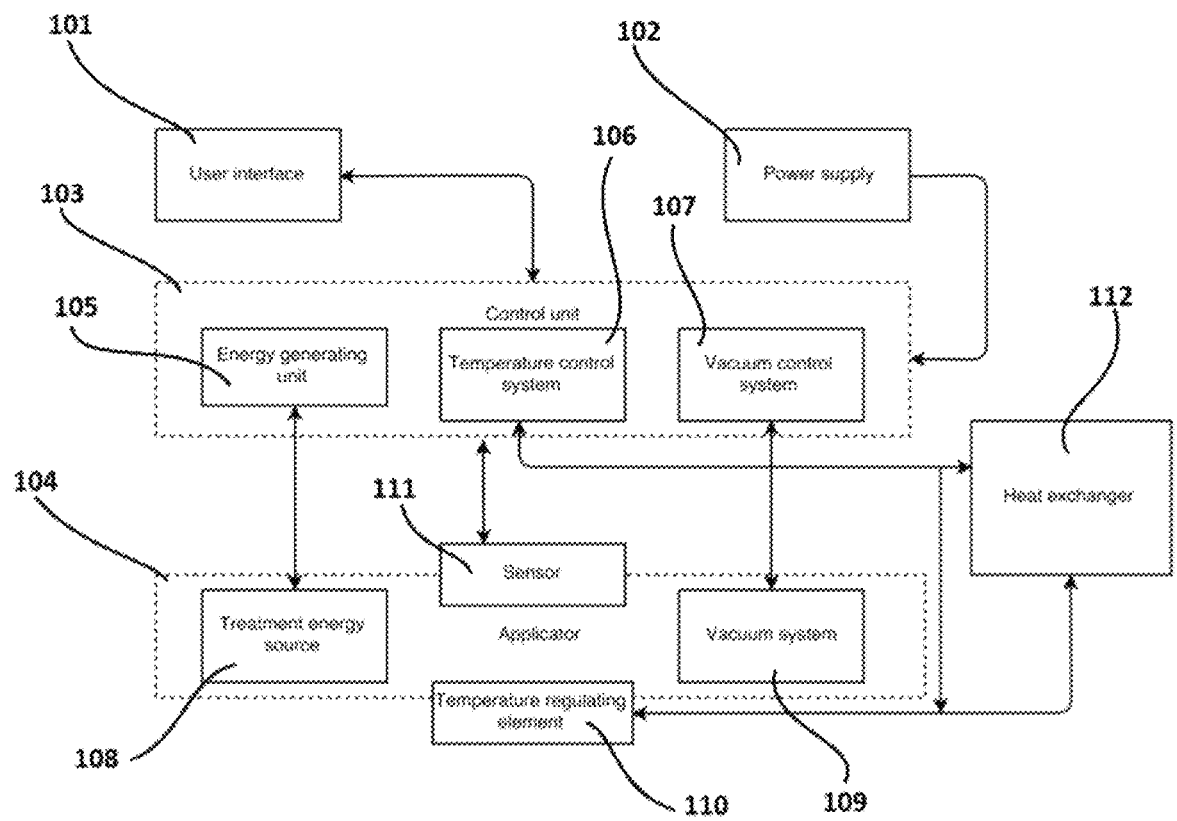
FIG. 1 is a schematic diagram of a treatment device

The device and method provide treatment of the soft tissue by applying at least one treatment energy source. Treatment may be based on selective capacitive and/or targeted inductive heating of the target soft tissue. Target tissue may be adipose tissue, collagen fibers and/or other part of the soft tissue where treatment energy is provided in order to provide a treatment effect. Treatment may also restore and accelerate cell metabolism, improve lymphatic circulation, blood circulation and/or blood supply of dermis.

The device may be used to remove and/or reduce: wrinkles, spider veins, volume of fat cells, number of fat cells, cellulite, redness of skin, pigment inhomogeneity, lupus symptoms, scars, acne and/or other body imperfections.

The device may also be used to rejuvenate skin, improve skin elasticity, skin hydration, circumferential reduction, body contouring and/or other treatment effect described in glossary.

According to one embodiment the device may treat and/or suppress diabetes symptoms.

The method and device may provide one or more treatment energy sources in order to provide treatment to the patient e.g.: vacuum (constant or variable pressure value under the applicator), mechanical wave energy (ultrasound wave energy, shock wave energy), light energy, plasma, thermal energy, electric current, magnetic field and/or preferably radio-frequency treatment energy (RF). Different treatment energy produced by treatment energy sources and different treatment effect may be used individually and/or may be combined. Different treatment energy may be combined in one or more treatment energy sources in one or more applicators. Such an example may be an RF electrode as a first treatment energy source and a piezo-element as a second treatment energy source wherein both treatment energy sources may be placed in one applicator or separate applicators.

According to one preferred embodiment, an RF energy source may be used in combination with treatment energy source improving blood and/or lymph flow (e.g. applied vacuum, mechanical wave, source of energy providing massage and/or muscle contracting stimulation) in order to improve heat redistribution produced by RF energy source in the soft tissue.

Another preferred combination may be RF treatment energy source and tempered RF electrode and/or applicator's contacting part to higher temperature than 37° C. The RF energy source in combination with heating energy source prevent leaking of heat delivered to patient's body by RF energy source. Treatment effect may be collagen fibers remodeling, induced neocollagenesis and elastogenesis that improve wrinkle reduction and skin laxity.

The device may treat any part of the patient body e.g. face, double chin, thighs, saddlebags, buttocks, abdomen, region of bra fat, arm, etc. The specific treatment energy as electric and/or magnetic muscle stimulation may be targeted to at least part of specific muscle group to stimulate at least part of one muscle fiber. Muscle groups may be major muscle group e.g.: upper back, infraspinatus, deltoids, biceps, triceps, forearms, chest muscle, middle back, lower back, side abs, rectus abdominis, gluteus maximus, hamstring group, quadriceps, tibialis anterior, calf; and/or deep muscle e.g.: pelvic floor muscles, psoas major muscle.

As shown in FIG. 1, the device may include a user interface 101, a power supply 102, a control unit 103, an applicator 104 and other device hardware parts.

User interface 101 may be used for switching the device on/off, selection of a treatment protocol, setting treatment parameters (before and/or during the treatment) and/or as an information panel. User interface 101 may be connected to control unit 103 and/or control unit 103 may be part of the user interface 101. User interface 101 may be operated by touch display, other type of display, one or more buttons, joystick, by other control element and/or combination of thereof. Optionally user interface 101 may be also external device connected to a control unit wirelessly, by wire and/or optical fiber. Such external device may be e.g. a smartphone, computer and/or other device.

A power supply 102 may interact with control unit 103, energy generating unit 105, temperature control system 106, vacuum control system 107, other controlling mechanisms, treatment energy sources e.g. treatment energy source 108, vacuum system 109 and/or temperature regulating element 110; and/or other parts with need of power supply.

Control unit 103 may comprise an energy generating unit 105, a temperature regulating system 106 and a vacuum control system 107. The energy generating unit 105, the temperature regulating system 106 and the vacuum control system 107 may be part of the control unit 103 or may be as individual controlling mechanisms that may communicate with control unit 103, with each other and/or with other controlling mechanism and/or sensor. The energy generating unit 105, the temperature regulating system 106 and the vacuum control system 107 may consist of software part, hardware part and/or combination of software part with hardware parts. The controlling mechanism may be able to change specific parameters of delivered treatment energy to the patient body. The parameters may include frequency produced by the treatment energy source, pressure under the applicator, position of the applicator, output power of treatment energy source, pulse mode, temperature of the applicator's contact part with the patient, patient's temperature and/or others. Each of controlling mechanisms may change specific parameters according to information sent by control unit 103, other controlling mechanisms, information sent from user interface 101, based on feedback information from at least one sensor and/or automatically according treatment protocol incorporated in controlling mechanism, control unit 103, or user interface 101.

The applicator 104 may include at least one treatment energy source 108, vacuum system 109, temperature regulating element 110, sensor 111 and/or other parts. A heat exchanger 112 may be localized in or outside of the applicator.

According another embodiment vacuum system 109, temperature regulating element 110 and/or sensor(s) 111 may be localized outside the applicator 104 (e.g. in the mother cases).

Control unit 103 may be located in the mother case as described in U.S. Provisional Application No. 62/375,796 incorporated herein by reference and/or in the applicator. Control unit 103 may comprise a separate or merged temperature control system 106 guiding temperature adjusting of the patient's epidermis, dermis, hypodermis, adipose tissue and/or temperature control system, energy generating unit, or vacuum control system.

Temperature control system 106 may provide guiding of at least one temperature regulating element 110 that regulates temperature of patient's soft tissue and/or any part of the device e.g.: the electrode, heat transmitter included in the heat exchanger 112, temperature of the material between treatment energy source and patient's body and/or any other part of the device.

Temperature regulating element 110 may include a passive temperature regulating element, active temperature regulating element or their combination.

A passive temperature regulating element may be an element changing temperature without need of input power supply e.g.: perforation of the applicator may provide cooling of any device by spontaneous air flow, material with high thermal conductivity removing heat by thermal diffusion between at least one part of the applicator and the environment spontaneously.

An active temperature regulating element may be an element changing temperature using an input power supply. An active temperature regulating system may be e.g.: heated or cooled fluid pumped to the applicator or in its proximity in order to adjust electrode temperature, a thermoelectric member adjusting temperature of any device part by the Peltier-Seebeck effect, heating coils heated by electric current, an element delivering sprayed coolant, ventilator and/or any other temperature regulating system.

Temperature control system 106 may cooperate with one or more sensors monitoring and/or contributing to evaluate temperature of the soft tissue and/or part of the device. Sensor or sensors contributing to evaluate temperature may not measure temperature as physical quantity but may measure a different physical quantity influenced by temperature and temperature may be calculated by using such influenced physical quantity. E.g. impedance of the soft tissue may change with changed temperature of such specific soft tissue part. Based on evolving impedance of the specific soft tissue part, temperature may be calculated by using a preprogramed correlation function.

Temperature may be controlled with regard to the temperature of the e.g.: RF electrode; heat transmitter (may be any kind of fluid e.g.: water, $CO_2$, etc.); dielectric material as described below; the patient's epidermis, dermis, hypodermis, adipose tissue as visceral adipose tissue and/or subcutaneous adipose tissue.

Temperature control 106 system may adjust temperature of a heat transmitter in the heat exchanger 112 with gaseous or liquid heat transmitter.

The heat exchanger 112 and/or gaseous or liquid heat transmitter may optionally be omitted.

Heating/cooling of the patient's soft tissue (e.g.: epidermis, dermis, hypodermis and/or adipose tissue) may be provided by conduction based on thermal diffusion between the applicator and the patient's body and/or by radiation caused by e.g.: RF waves, acoustic waves, plasma, muscle stimulation, friction, and/or other.

The device and method maintain optimal treatment temperature of the patient's surface (epidermis) and/or contact part of the applicator in the range of 28° C.-54° C. or 30° C.-50° C. or 35° C.-48° C. or 36° C.-45° C. or 36-41° C.

According to one embodiment contact part of the applicator may be tempered in range of 35° C.-45° C. e.g. by liquid flowing through the RF electrode, by resistive heating of the electrode and/or by other mechanism. The RF source of energy targeted to hypodermis and deeper decrease adipose cells volume, adipose cells number and also heats epidermis and dermis from the opposite side than tempered contact part of the applicator. As a result patient's epidermis and dermis is heated from the both sides that cause homogenous heating across the volume of epidermis and dermis with minimal energy losses and higher effectiveness of the device. Heating of epidermis and dermis maintained in range of 35° C.-45° C. effect skin metabolism and collagen fibers that results in skin tightening, rejuvenation and/or wrinkle reduction.

In the present device and method the patient's epidermis may be heated to the temperature mentioned above in order to prevent heat shock of the patient's body. Any part of the applicator may be heated/cooled by itself and/or by temperature regulating element 110 and may regulate patient's surface temperature.

According to one embodiment patient's surface may be heated and/or cooled by thermal conduction and/or radiation between a heater/cooler, RF electrode and the patient's and/or between heater/cooler, a dielectric material and patient and/or between heater/cooler and patient surface or skin. The dielectric material may be any dielectric and/or insulating material with dielectric constant/relative permittivity higher than 1 and located between the RF electrode and patient's surface. The dielectric material may be e.g.: bolus filed with any fluid, textile layer, silicon active agent etc.

If a temperature difference between patient surface and treated lower layers of the patient's soft tissue (e.g. hypodermis, visceral adipose tissue) is too high the treatment may be uncomfortable and/or painful. For example if patient's epidermis is cooled to 25° C. and patient's adipose tissue is heated to 48° C. then heat significantly and very fast diffuses from heated adipose tissue into the cooled area of the skin and treatment is inefficient, inhomogeneous and health risk may be increased.

Figure 2A:
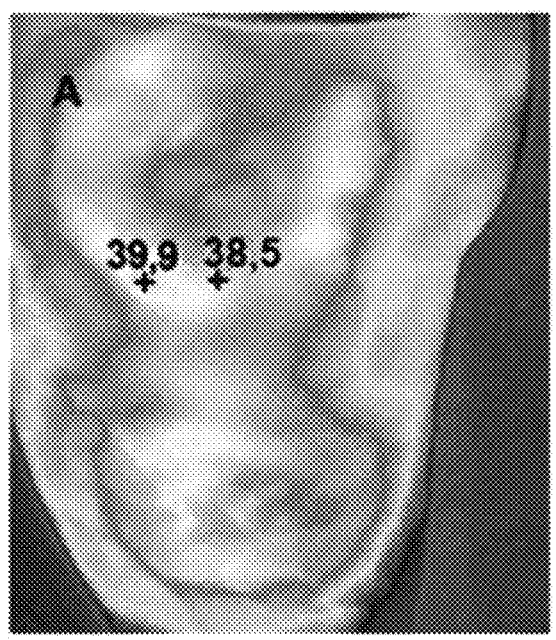
FIG. 2A and FIG. 2B illustrates influence of patient's surface heating/cooling to homogeneity of provided treatment
Figure 2B:
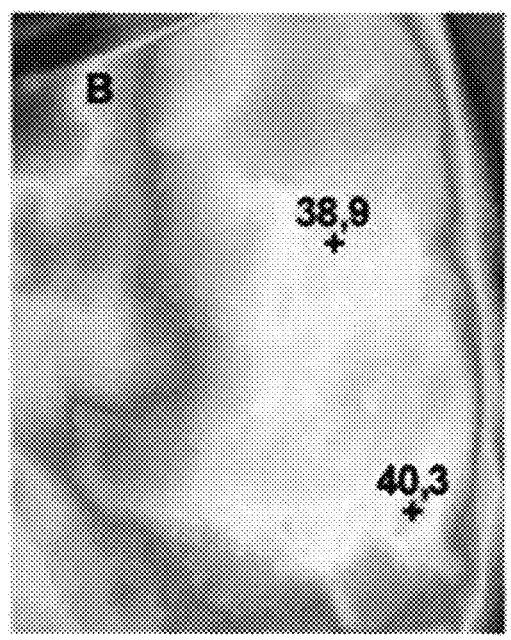

FIG. 2A and FIG. 2B are pictures from a thermo-camera that illustrates surface temperature after treatment provided by a bipolar RF source. FIG. 2A demonstrates treatment by two applicators (according to FIG. 6) where an electrode of each applicator was cooled below 25° C. FIG. 2B demonstrates treatment with the same applicators where electrode of each applicator was heated above 25° C. Cooled/heated electrodes according to FIG. 2A and FIG. 2B influenced temperature of the patient's epidermis and homogeneity of the treatment of hypodermis.

Heating the patient's surface to 25° C. or higher but lower than 43° C. (which is pain threshold) is very effective for improvement of homogeneity of the delivered RF treatment energy and energy distribution in the soft tissue. Heating the patient's surface also minimizes heat diffusion from the heated soft tissue (e.g. adipose tissue), which may improve effectiveness and homogeneity of the treatment and also may allow for shorter treatments Heating the patient's surface improves blood flow in the skin which improves dispersion of the heat in the skin surface, preventing creation of hot spots. Increased blood flow may locally accelerate body metabolism and also accelerate removing of damaged and/or dead cells. Such effect may accelerate results and reduce health risk. Increased blood flow may also improve selectivity of RF heating and filtering of unwanted/parasitic frequencies of the RF signal.

Heating of the patient's epidermis shows positive influence to the skin rejuvenation, increase skin elasticity and improvement of skin imperfections (e.g. structural inhomogeneity, stiffness of the scar). Heating of the patient's surface, namely dermis, with a combination of RF treatment, also improves results of cellulite removal and local acceleration of cell metabolism.

According to another embodiment cooling of the patient's epidermis below 20° C. may be provided. When skin surface temperature is decreased below 20° C. pain receptors may have lower sensitivity. With cooling of the patient's surface, it is also possible to increase output power of the treatment energy source 106 beyond the limit acceptable during treatment without regulation of the patient's surface temperature. This method requires optimal adjusting of delivered treatment energy parameters.

Optimal treatment temperature of the treated adipose tissue may be in the range of 38-60° C. or 41-47° C. or 42-45° C. The method and the device may be designed to provide many kinds of a treatment mostly based on apoptotic, necrotic destruction of adipose tissue and/or increasing adipose metabolism (catabolism). Therefore the treatment leads to reducing number and/or volume of adipose cells. Another therapy may be targeted to soft tissue layer (e.g. dermis) in order to start neocollagenesis and/or elastogenesis (for e.g. wrinkle reduction, rejuvenation).

Heating of epidermis and/or other soft tissue structure (e.g. dermis, hypodermis, adipose tissue) may be provided continuously with continual heating or according to an arbitrary heating sequence until soft tissue temperature reaches a predefined tissue temperature. During continual heating treatment energy source output may be variable but temperature of the soft tissue rises until a predefined soft tissue temperature is reached. During the heating sequence the treatment energy source output may be variable. The temperature of the soft tissue may increase at least twice and also decrease at least once until a predefined temperature is reached.

Figure 3:
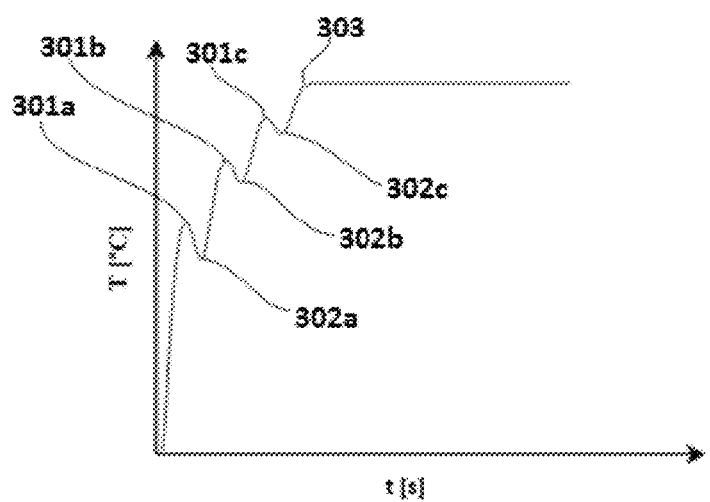
FIG. 3 illustrates a heating sequence of the patient's surface

FIG. 3 illustrates one possible temperature profile of the soft tissue. The vertical axis in FIG. 3 symbolizes temperature of the specific soft tissue layer (e.g. epidermis), and the horizontal axis symbolizes time. According to FIG. 3, at the beginning of the treatment a rapid rise of the temperature in the soft tissue may occur until the discomfort temperature level 301a is reached. Then temperature of the soft tissue (e.g. epidermis) may be reduced by at least 0.2° C. or a value between 0.2 to 4° C. or 05 to 3° C. or 1-2° C. to a comfortable temperature level 302a. Further temperate increases follow to a value of at least 0.2° C. or a value between 0.2 to 4° C. or 0.5 to 3° C. to a temperature higher than the prior maximal temperature of the discomfort level. Such heating profile may be practiced with multiple discomfort temperature levels e.g. 301b, 301c and multiple comfortable temperature levels e.g. 302b, 302c until a desired temperature 303 is reached. Between two discomfort temperature levels temperature of the soft tissue may not be reduced but may be kept constant for some time interval and then temperature of the soft tissue may be reduced or raised again. Temperature heating profiles may be guided by operator, by control unit 103 and/or by temperature control system 106, by energy generating unit 105 and/or by the treatment energy source.

Methods of heating described by FIG. 3 may be useful to adapt heat sensitive skin receptors to higher temperatures of the soft tissue than is normally comfortable, to prevent heat shock to patient's body, help to adapt patient's body to treatment, stabilize biological processes during the treatment and/or may enable reaching therapeutic desired temperature 303 in the soft tissue in shorter time. Such heating profile also prevent that patient's body automatically starts to cool treated body area during the initial phase of treatment.

Treatment may be more effective with lower energy losses and side effect to patient's body as a result.

According to another embodiment a heating profile of the patient's soft tissue reaching predefined optimal treatment temperature may be at least partially exponential. After reaching the certain predefined temperature and/or after specific time delay, heating and/or cooling may be slowed and temperature of the soft tissue may be kept constant. Priority of such heating profile is to reach optimal treatment temperature as soon as possible and/or on the higher temperature value than is comfortable without such heating profile.

According to another embodiment a heating profile of the patient's soft tissue in time may be defined at least partially by logarithmic, linear, periodical, or polynomial functions and/or a combination of these functions where variables are temperature and time.

Time needed to reach optimal soft tissue treatment temperature according to the proposed device and method is after 7 minutes, more preferably after 4 minutes, more preferably after 2 minutes, more preferably after 1 minute, even more preferably after 50 s, even more preferably after 40 s, even more preferably after 30, most preferably after 5 s after treatment start. The therapeutic desired temperature may be kept for 0.05-30 minutes or 0.2-25 minutes or 0.5-20 minutes or 0.2-18 minute.

The device and method produce temperature difference $\Delta T_1$ between a contact part of the applicator and treated adipose tissue. Temperature difference $\Delta T_2$ is created between epidermis and treated adipose tissue. Temperature difference $\Delta T_3$ is created between epidermis and non-adipose tissue in dermis. Absolute values of the temperature difference $\Delta T_1$ may be in the range of 0-18° C. or 0-15° C. or 3-15° C. or 2-10° C., wherein the adipose tissue has a temperature preferably higher than a contact part of the applicator. Absolute values of temperature difference $\Delta T_2$ may be in range of 0-18° C. or 0-10° C. or 2-7° C., wherein the adipose tissue has preferably a higher temperature than the epidermis. Absolute values of temperature difference $\Delta T_3$ may be in the range of 0-18° C. or 0-10° C. or 2-8° C.

The heating source of the applicator may be a thermally regulated RF electrode and/or a dielectric material located between treatment energy source and patient's surface (epidermis). The thermal gradient between the RF electrode surface and the patient's surface may be in range between 0-15° C. or 5-12° C. or 8-12° C. A thermal gradient between the RF electrode surface and the patient's surface may be influenced by a dielectric material that may be localized between the RF electrode and the patient's surface. Thermal conductivity of the dielectric material at 293° Kelvin may be in range 0.001 to 500 W·m$^{-1}$·K$^{-1}$ or in range 0.015 to 450 W·m$^{-1}$·K$^{-1}$ or in range 0.015 to 450 W·m$^{-1}$·K$^{-1}$ or in range 0.015 to 200 W·m$^{-1}$·K$^{-1}$.

The device may comprise one or more sensors providing feedback information to control unit 103, user interface 101 and/or to an individual controlling mechanism. Based on evaluated feedback information, treatment parameters may be adjusted by control unit 103, by a user and/or by any controlling mechanism. A sensor may be located in a heat exchanger, system enclosure and/or in the applicator. Sensors in the device may measure: pressure under the applicator, temperature, viscosity of heat transmitter, flow of the heat transmitter, impedance, capacity, permittivity, conductivity, susceptibility of any part of the device and/or patient's body, sensors analyzing backscattered signal, infrared radiated spectrum and its intensity, heat capacity, voltage, electric current, phase shift of delivered and backscattered signal of treatment energy, pulse of the patient and any other biological, biochemical and/or physical parameter e.g.: skin tension, muscle tension, level of muscle contraction, amount of perspiration, breathing frequency, etc.

Temperature of the soft tissue may be measured by a sensor directly evaluating temperature as a physical quantity (e.g. thermometer, thermal imager, etc.) Another method to evaluate temperature may be by measuring a different physical quantity other than temperature, wherein the physical quantity is thermally dependent (e.g. by measuring impedance of the soft tissue beneath the epidermis and counting soft tissue temperature based on a correlation function that describes such soft tissue dependence of impedance on temperature). Indirect methods of measuring soft tissue temperature may be beneficial to evaluate noninvasively temperature of the soft tissue under the epidermis, dermis and/or hypodermis.

According to another embodiment cooling of the patient's epidermis below 20° C. may be provided. When skin surface temperature is decreased below 20° C. pain receptors may have lower sensitivity. With cooling of the patient's surface it is also possible to increase output power of the treatment energy source 106 beyond the limit that is acceptable during treatment without regulation of the patient's surface temperature. This method requires optimal adjusting of delivered treatment energy parameters in order to provide optimal homogeneity treatment.

Figure 4:
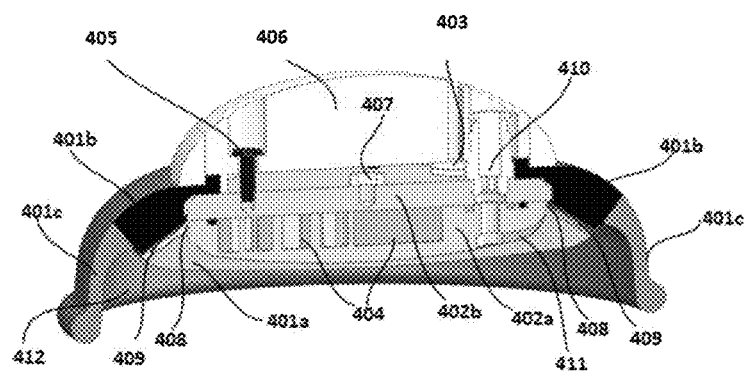
FIG. 4 illustrates an applicator embodiment.

As shown in FIG. 4, an applicator may have one RF electrode with upper part 402b and lower part 402a. The RF electrode may include one or more cavities 404 with the same or different volumes. Cavity 404 may be filled by heat transmitter through the inlet/outlet aperture 403 in order to regulate electrode temperature or physical properties.

RF electrode 402a-402b may be at least partially covered by dielectric material which may be divided into parts 401a, 401b and 401c. Part 401a is dielectric material under the electrode and on the side of the RF electrode (especially lower part 402a of the RF electrode). Part 401b may fix the dielectric material to other parts of the applicator and also may hold other applicator parts together. Part 401c is a vacuum edge that in combination with supplied vacuum under the applicator may attach the applicator to the patient's surface. Dielectric material with parts 401a-401c may be designed as individual parts 401a, 401b and 401c or as one piece.

Vacuum may be delivered under the applicator by at least one inlet/outlet vacuum aperture 410. This aperture may go through the electrode around the electrode and/or through the part 401a, 401b or 401c of the dielectric material directly into the cavity 412 under the applicator. According to FIG. 4 vacuum aperture 410 goes through the RF electrode to the vacuum guide 411 leading to vacuum channel 408 in the electrode and/or in the dielectric material. Vacuum channel 408 redistributes vacuum around the electrode and to the vacuum pipe 409. Dielectric material may include one or more vacuum pipes 409 applying vacuum to the cavity 412 under the applicator.

Isolating elements as an upper applicator lid 406 and an isolation for power supply cable 407 may be attached to the electrode.

Individual parts of the applicator may be connected by connecting member 405 (e.g. screws, glue, snapped to each other, molded to each other, connected by vacuum and friction forces, fixed by interaction between polar and non-polar groups of different materials and/or may be hold to each other by magnetic and/or electromagnetic forces as described in U.S. Provisional Application No. 62/375,796 incorporated herein by reference.

According to one embodiment at least two parts of the applicator may be connected together by dielectric material, e.g. in FIG. 4 dielectric material including parts 401a-401c may hold together lid of the applicator 406 upper and lower part of the RF electrode 402b and 402a without need of screws and/or other fastening mechanism.

The method and device may be based on capacitive RF heating of the soft tissue by bipolar and/or multipolar electrode arrangement with applied vacuum under the applicator e.g. in the applicator's cavity 412 and controlled heating of the patient's surface by thermal diffusion. One applicator may include one or more electrodes. The device may also include none, one or more RF electrodes heating the soft tissue by RF inductive heating e.g. heating of collagen fibers. The device may include at least one applicator. According another embodiment RF electrode(s) may be substitute and/or replenish by other source of energy than RF source of energy (e.g. by ultrasound transducer, light energy source and/or other).

The RF electrode(s) may exhibit multipolar system behavior where at least one electrode is connected with RF energy flux density between at least two another electrodes. One RF electrode and/or group of RF electrodes including at least two RF electrodes may be switched on/off according treatment pattern as it is described in in U.S. Provisional Application No. 62/375,796 incorporated herein by reference.

The distance between edges of the RF electrodes' treatment energy sources may be at least 1 cm and/or be in the range from 1 cm to 40 cm, or 1 cm to 25 cm or 5 cm to 20 cm.

Target depth of the RF treatment energy may be between 0.1 cm 20 cm or between 1 cm to 20 cm or between 1.5 cm to 12 cm or between 2 cm and 8 cm in the patient's soft tissue.

According to an exemplary embodiment the device includes an even number of the applicators wherein each applicator includes one electrode (see FIG. 4). A couple of such applicators exhibit bipolar system behavior with adjustable RF energy flux density between electrodes of the applicators.

One or more electrodes may have different sizes and shapes that influence the size of the treated area, focus of the treatment, parameters of provided treatment energy and/or homogeneity of the treatment. Electrodes may be formed by conductive wire or system of wires, by a conductive plate and/or other conductive or semi-conductive object. Shapes of electrodes may be asymmetrical or at least partially symmetrical e.g.: oval, elliptical, planar, square, wavy, convex, concave, spiral and/or other shape of electrode and/or shape of electrode surface. The electrode may consist of one or more pieces. The electrode with rounded edge(s) may minimize edge effect and prevent hot spot creation. According to a preferred embodiment an RF electrode has a circular contour in longitudinal cross section and at least partly elliptical shape of lower part of the electrode 402a in vertical cross section, as shown in FIG. 4.

Diameter of the RF electrode in FIG. 4 may be in the range from 0.6 cm to 40 cm or from 6 cm to 30 cm or from 6 cm to 15 cm or may have any other diameter.

The RF electrode of the device may have different sizes and shapes. Surface size of the RF electrode contacting the patient (see lower part of the electrode 402a FIG. 4) may be in range between 1 cm² to 1200 cm² or between 10 cm² to 800 cm² or between 30 cm² to 300 cm² or 30 cm² to 100 cm².

RF electrode may have also different surface modification e.g. elox and/or other epoxy layer to prevent oxidation of the RF electrode.

Figure 5:
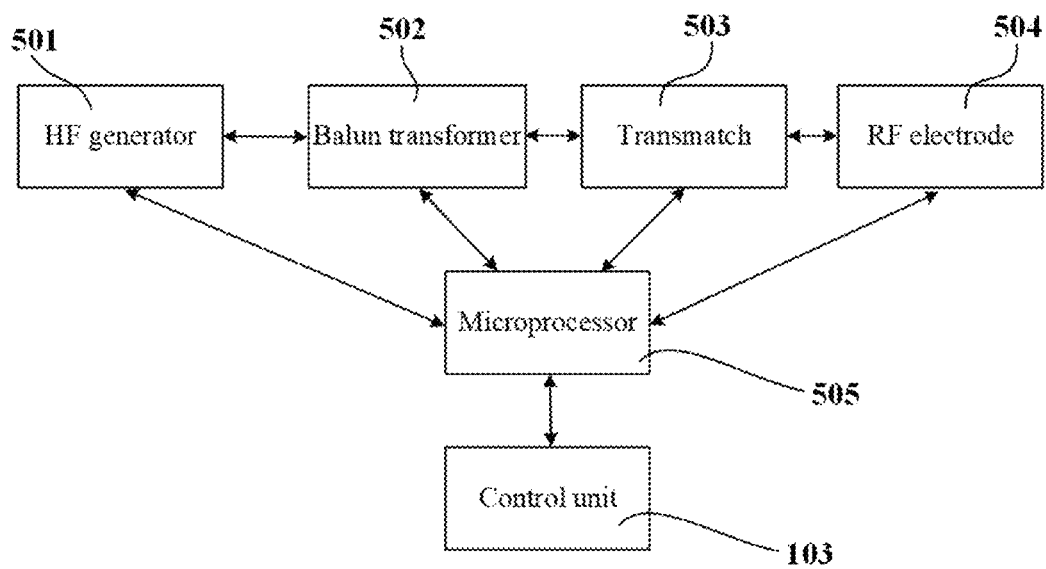
FIG. 5 is a schematic diagram of an RF-regulating system

In order to provide improved adjustment of delivered treatment energy, parameters may be used in an RF-regulating system (see FIG. 5). An RF-regulating system may be part of treatment energy source 108 and/or energy generating unit 105. RF-regulating system may include any part from the FIG. 4. e.g.: may include an HF generator 501, balun transformer 502 that converts between balanced or unbalanced signal, impedance matching circuit (e.g. transmatch) 503, RF electrode 504 and/or microprocessor 505. RF-regulating system may communicate with control unit 103 or may be part of it.

According to another embodiment microprocessor 505 and/or other part of RF-regulating system may not be included or may be part of another controlling mechanism.

HF generator may be regulated in order to increase amplitude of delivered treatment energy signal and so increased output power of the treatment energy source.

Balun transformer may transform balanced signal to unbalanced and vice versa. Balun transformer may transform signal before and/or after adjusting signal by transmatch.

Transmatch may adjust frequency of treatment energy signal to optimize selective heating of targeted tissue with minimal signal back scattering and heating of unwanted soft tissue structure.

RF electrodes providing capacitive heating of the soft tissue creates with treated soft tissue an imaginary capacitor. In order to improve adjustment of delivered treatment energy parameters and capacity of such imaginary capacitor may be adjusted according to the active surface of the electrode. RF electrode as treatment energy source may include apertures. Size of the electrode's apertures may be varied and so capacitance of imaginary condenser created by two RF electrodes and the soft tissue may be varied. Adjusting of RF electrode surface may be also provided by other mechanism as described in U.S. Provisional Application No. 62/351,156, incorporated herein by reference.

The relative permittivity of a material is its (absolute) permittivity expressed as a ratio relative to the permittivity of vacuum.

Permittivity is a material property that affects the Coulomb force between two point charges in the material. Relative permittivity is the factor by which the electric field between the charges is decreased relative to vacuum.

Likewise, relative permittivity is the ratio of the capacitance of a capacitor using that material as a dielectric, compared with a similar capacitor that has vacuum as its dielectric. Relative permittivity is also commonly known as dielectric constant.

According to presented device RF field is generated between at least two RF electrodes that create a capacitor. Patient is located inside the RF field. RF energy flux density is highest near the edges of the RF electrode based on distribution of electric charge.

In order to prevent edge effects, rounded RF electrodes may be used that may have different thickness on the edges of the electrode than at the center of the electrode or the RF electrodes may have curved ending parts. Another mechanism how to prevent edge effect may be provided by changing absolute value and/or shape of some RF field force lines. Changing shape and intensity at least locally may be provided by placing dielectric material and/or insulating material with different thickness and/or relative permittivity across such material. As a result capacity of the capacitor created by the RF electrodes is locally changed and so gradient of RF field is changed that may cause homogenous tissue heating and preventing edge effect.

Local capacity change is related to different dielectric material thickness and/or relative permittivity between different locations below RF electrode. That leads to definition of polarization factor defined as:

$$P = \varepsilon_r d$$

where polarization factor P [mm] place is defined as relative permittivity $\varepsilon_r$ of dielectric material multiplied by thickness d of dielectric material at exact.

Absolute value of difference between polarization factor below centre of the RF electrode and below edges of the RF electrode may be in range from to 0.10005 mm to 19800 mm or from 1 mm to 800 mm or from 2 mm to 600 mm or from 3 mm to 400 mm.

In order to prevent edge effect, improve focusing and homogeneity of provided RF energy into the soft tissue dielectric material part 401a may be profiled. Profiled part 401a of dielectric material may be thinner below the center of the RF electrode than below the RF electrode edge. Thickness of profiled part 401a of dielectric material below the center of electrode may be in range from 0.1 mm to 10 cm or from 0.5 mm to 1 cm or from 1 mm to 5 mm. Dielectric material below the electrode's edge may be thick in range from 0.2 mm to 12 cm or from 1 mm to 3 cm or from 2 mm to 1 cm. Thickness of the dielectric material part 601a below the electrode's edge may be at least 5% or 10% or 20% or 50% or 100% or 300% thicker than is dielectric material below the center of RF electrode.

Average dielectric constant of the dielectric material e.g. part 401a may be in range from 1.0005 to 2000 or from 1.1 to 150 or from 1.2 to 100 or from 1.2 to 80 under the electromagnetic field with frequency 50 Hz and temperature 298.15 K.

Stiffness of the dielectric material may be in range shore A5 to shore D80 or shore A5 to shore A80 or shore A10 to shore A50 or shore A10 to shore A30. Dielectric material may be made of different polymeric characterization.

As dielectric materials may be considered any type of gel and/or other substance located between applicator's contact part and patient's body creating layer thicker than 0.1 mm. Gels may help to improve energy transfer to patient's body and/or may realize active substance to patient's body in order to provide treatment more comfortable and/or improve treatment results.

According another embodiment profiled part 401a of dielectric material may be substitute by non-profiled part 401a of dielectric material with different dielectric properties at the edges of the RF electrode than dielectric properties at the center below the RF electrode. For example dielectric material may have higher relative permittivity below the edges of the RF electrode than below the center of the RF electrode.

According to another embodiment the RF electrode may be thicker on the edges than in the center and/or RF electrode may also have rounded edges. Such RF electrode embodiments may help to prevent edge effect and in combination with above described dielectric material, the edge effect may be minimized or removed.

Prevention of the edge effect may be also provided by an RF electrode created from the planar winded coil where wire may have thicker diameter with longer distance from a center of the winded coil and/or a distance between individual turns of the winded coil may be higher out of the centre of the winded coil than near by the centre of the winded coil.

According to another embodiment some part of dielectric material, namely part 401a, may include one or more cavities inside. Cavity inside dielectric material may be filled with heat transmitter and may be thermally regulated and/or may change dielectric properties of such dielectric material part.

Part 401c of dielectric material called vacuum edge or vacuum cup may define a magnitude of a patient's skin protrusion, pressure value needed for attaching applicator to patient's body and other properties. Vacuum edge 401c may have a circular, rectangular or other symmetrical or asymmetrical shape.

Dielectric material parts 401a-401c may be rigid, at least partly shape adaptive and/or at least partly elastic. Dielectric material from at least partly shape adaptive material may provide flexibility to adapt applicator surface to patient's surface and improve contact of the dielectric material with electrode and/or the patient body. Shape adaptive material(s) may also improve energy transfer from applicator to patient's soft tissue. Dielectric material under the RF electrode may be any kind of polymeric material and/or blend of multiple materials with specific dielectric parameters (e.g.: silicone, latex, rubber and/or other).

According to FIG. 4, a dielectric material may include parts as 401a, 401b and/or 401c. Dielectric material in the applicator may be created as one piece including parts as dielectric vacuum edge 401c, dielectric layer under the treatment energy source 401a (e.g. RF electrode) and/or at least part of the dielectric applicator covering 401b. According to another embodiment of dielectric material, the dielectric material may be composed of several individually fabricated parts e.g. parts 401a, 401b and 401c. Individual parts or segments of dielectric material (e.g.: 401a, 401b, 401c) may have the same or different mechanical, chemical, electrical, and/or magnetic properties (e.g. elasticity, stiffness, durability, dielectric constant, biocompatibility, etc.).

Optionally, an applicator may include flexible shape changing and/or elastic polymeric dielectric material as one piece including parts 401a, 401b and 401c which may provide better adaptiveness of the applicator to patient's body, better integrity of applicator and easy way how to exchange this part which may be in contact with patient during the treatment. Exchangeability of dielectric material may be convenient to improve hygiene of the treatment, personalization for individual patients and application needs and decrease costs of exchange worn applicator parts. According to one embodiment dielectric material may be exchanged for another one and/or removed without need for screws and/or technical knowledge.

Dielectric material (spacing object) located between patient's soft tissue surface and treatment energy source may have specific properties and influence parameters of treatment energy as it is described in U.S. Provisional Application No. 62/331,072 is incorporated herein by reference.

According to another embodiment some part(s) of a contact applicator part may be omitted from covering by dielectric material, e.g. dielectric material under the treatment energy source may be at least partially omitted.

Vacuum (lower air pressure than is air pressure in the room) may be used for attaching of the applicator to a certain patient's body part, may regulate contact area size of dielectric material under the treatment energy source with the patient's surface, may provide massage of the patient's soft tissue, may help to reduce creation of hot spots and edge effect, may increase body liquids circulation and/or different protrusion shapes.

Regulation of vacuum may be provided in mother case as it is incorporated here in reference in provisional app. No. 62/375,796, in the applicator (e.g. by Peltiere's member) and/or on the way between mother case and applicator (e.g. cooled in the heat transmitter guide). Regulation of the vacuum brought under the applicator may be executed by valve, by construction of the device (mainly applicator) and/or by system regulation of output power of vacuum system.

Figure 6:
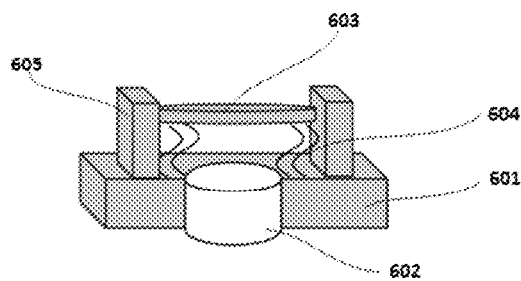
FIG. 6 illustrates a valve embodiment

The device may include one or more valves. Valves may be controlled by control unit and/or may be self-controlled depending on the air pressure value in the cavity under the applicator and on the other side of the valve closer to vacuum pump. One possible embodiment of self-controlled valve is illustrated in FIG. 6. FIG. 6 illustrates vacuum inlet/outlet aperture 602 located in wall 601 dividing environments with different pressure value. The aperture is closed by closing object 603 pushed by springs 604 against the wall 601 or by other mechanism. Springs 604 may be fixed in closing object 603 and wall 601 or to other part of the valve. Closing object 603 may be moved along rails 605 defining the movement path of the closing object 603. If air pressure on the valve side closer to the cavity under the applicator exerts higher force to closing object 603 than springs from the other side of the closing object 603 then valve is closed, if not the valve is opened. Opening and closing valve may be based on different principle e.g. as one described above, regulating applied vacuum may be based on increasing/decreasing diameter of aperture 602 and/or by another principle.

According another embodiment the device does not need to use any type of valve in the applicator. Design, material and number of device parts that are involved to delivering of vacuum under the applicator may regulate air pressure under the applicator also without any valve. According to one possible applicator embodiment illustrated by FIG. 4, the vacuum value (lowest air pressure) distributed to the cavity 412 under the applicator with constant output power of vacuum system may be influenced by the number and/or diameter of vacuum pipe 409, inlet/outlet aperture 410, vacuum guide 411 and/or by channel 408.

According to another embodiment the applicator may be designed so that vacuum under the applicator may change cross-sectional area of vacuum guiding part and influence air pressure value under the applicator. Change of vacuum guiding part cross-sectional area and/or shape may be caused by expansion, shape change and/or deformation of material(s) which the part is made of.

Figure 7:
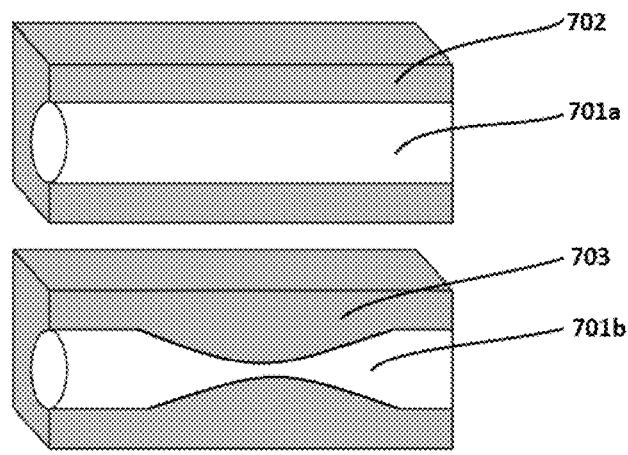
FIG. 7 illustrates shape change of a vacuum guiding part that may regulate vacuum level

One example of expansion, shape change and/or deformation of vacuum guiding part may be FIG. 7 where 701a is an aperture of guiding vacuum part 702 during normal air pressure in the aperture 701a and 701b is an aperture of guiding vacuum part 703 during decreased air pressure in the aperture 701b.

Figure 8:
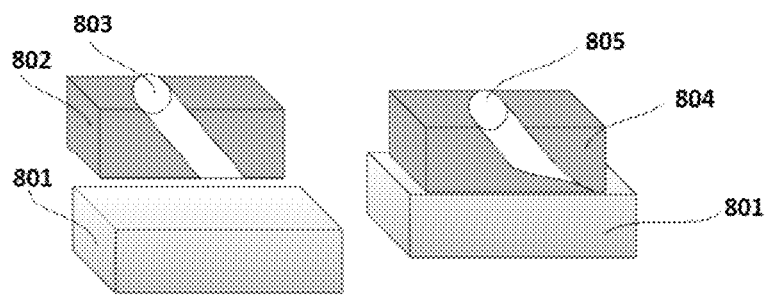
FIG. 8 illustrates deformation of a vacuum guiding part that may regulate vacuum level under the applicator

Another example of expansion, shape change and/or deformation of device part involved to delivering of vacuum under the applicator may be FIG. 8 where 801 is the patient's skin or surface, 802 dielectric material including vacuum pipe 803 with no contact with patient's surface and 804 is a dielectric material in contact with patient's surface that deformed vacuum pipe 805 by pressure of the patient's surface.

Vacuum under applicator may be constant and/or may be changed during the treatment time.

Constant air pressure under the applicator may be provided by continually pumping air out of the applicator. According to one embodiment providing constant air pressure lower than atmospheric pressure, vacuum system is operating during whole treatment and is not regulated by any valve. At the beginning of the treatment applicator attached to patient body and may be fixed to specific area. After fixing applicator to patient's surface vacuum system output power is decreased to a value where air amount pervade from the outside of the applicator to cavity 412 below the applicator is in balance with amount of sucked air from the cavity 412 below the applicator.

In other embodiment and/or treatment protocol vacuum output power may be constant during at least part of the treatment, creating equilibrium between air pervading into the cavity below the applicator and air sucked out of the cavity, provided by the diameter and length of the vacuum related device parts under the applicator (e.g. 409 and/or 410 see FIG. 4). The mechanism of such equilibrium is based on air friction and turbulence in the narrow device parts.

Another mechanism for keeping constant pressure under the applicator is to regulate opening, closing and/or changing inlet/outlet aperture of the valve(s) when the pressure under the applicator is changed.

Constant pressure under the applicator may be provided by increasing output power, decreasing output power and/or switching on/off of the vacuum system.

Pressure under the applicator may be changed during the time of the therapy. Changing pressure value under the applicator may be cyclically repeated during the therapy. Such effect may be used as massage of the adjacent soft tissue. Massage of the adjacent soft tissue in combination with RF treatment energy source may accelerate treatment effect, improve treatment results and decrease health risk. Massage of soft tissue may improve lymph and blood flow that improve heat distribution in the adjacent soft tissue that lower risk of creating hot spots and thermal inhomogeneity on the patient's surface. Massage in combination with RF treatment energy source may accelerate fat metabolism, elastogenesis and/or neocollagenesis. Massage may stimulate movement of body fluids, as described in U.S. patent application Ser. No. 15/433,210, incorporated herein by reference.

Cycle changing pressure value under the applicator may be provided by increasing/decreasing output power of vacuum system, by changing diameter of inlet/outlet aperture for pumped air out of the cavity below the applicator, by closing/opening of at least one valve and/or combination thereof.

Changing pressure value under the applicator may change contact area of the dielectric material 401a or RF electrode with patient's surface. According to one embodiment, changing the pressure value under the applicator changes protrusion of the soft tissue between vacuum edge 401c and dielectric material part 401a. This may also change targeting and/or amount of delivered treatment energy source on the edge of the treatment energy source (e.g. electrode) that may also prevent edge effect, creation of hot spots and other health risks.

Pressure value under the applicator may be changed compare to pressure in the room during the treatment in range from 0.1 to 100 kPa or from 0.2 kPa to 70 kPa or from 0.5 kPa to 20 kPa or from 1 kPa to 10 kPa or from 2 kPa to 8 kPa.

Negative pressure created under the applicator may be lower compared to room pressure in range 0.01 kPa to 100 kPa or from 0.1 kPa to 20 kPa or from 0.3 kPa to 50 kPa or from 0.3 kPa to 30 kPa or from 0.5 kPa to 30 kPa.

The applied negative pressure may be continual or pulsed. Continual pressure means that the pressure amplitude is continually maintained after reaching the desired negative pressure. A pulsed pressure means that the pressure amplitude varies during the therapy. The pulsed negative pressure may alternate with peak pressure differences from 0.1 kPa to 100 kPa with regards to pressure in the room (atmospheric pressure), more preferably from 2 kPa to 20 kPa with regards to pressure in the room (atmospheric pressure), most preferably from 2 kPa to 10 kPa with regards to pressure in the room (atmospheric pressure). The duration of one pulse is in a range between 0.1 s to 1200 s or 0.1 s to 100 s or 0.1 s to 60 s or 0.1 s to 10 s; wherein the pulse means duration between two beginnings of successive increases or decreases of negative pressure value.

In case of using pulsed pressure the ratio of $P_h/P_1$ where $P_h$ is value of highest pressure value a $P_1$ is lowest pressure value during one cycle of repeated pressure alteration may be in range from 1.1 to 30 or from 1.1 to 10 or from 1.1. to 5.

According to one embodiment pressure in the cavity under the applicator 412 may be continually decreased during initiating of the treatment and when pressure reaches a predetermined value, a pressure pulse cycle begins.

Placing or holding of the applicators adjacent to the patient's body and switching between them may be provided as described in U.S. Provisional Application No. 62/358,417 incorporated herein by reference and/or in in U.S. Provisional Application No. 62/375,796 incorporated herein by reference.

In one aspect the device is designed as a belt that may be modularly modified by adding and/or removing one or more part of the device (e.g.: applicators, treatment units and/or others) before and/or during the treatment. The belt is designed to fit to any type and size of treated patient body area. In one preferred embodiment the belt is in touch with patient's body surface matches the curvature of patient's body. Size of the belt may be variable by stretching and/or by plugging and/or removing of one or more parts of the belt.

In another embodiment the belt may be considered as a block of at least two treatment applicators attached in optimal working distance to the patient's body. Optimal working distance may be any distance from the skin of the patient or in direct contact with the skin of the patient. Applicators may have various sizes and shapes.

Treatment applicators may provide different types of treatment therapy e.g.: radio-frequency therapy (RF therapy), plasma therapy, ultra-sound therapy, acoustic wave, shock wave therapy, light (coherent, non-coherent) therapy, heating, cooling, electro-therapy, therapy by generated magnetic field (include muscle stimulation), positive or negative pressure therapy, vibration therapy and/or massage therapy. Treatments may be performed completely without attendance of the operator and/or treatment procedures may by modified during the treatment.

One or more treatment applicators may communicate with each other and/or with one or more control units via cables, wireless and/or via connection through the belt. Transfer of the information through the cable may be based on conductive mechanism and/or via mechanism used in an optical fibers and/or as a wave guide provide transfer of different types of the energy (e.g.: sonic, electric, electro-magnetic, pressure by liquid or gas substances and/or other). The communication may provide information about locations and/or type of the applicator/applicators, treatment protocol, treatment parameters and other information. In some embodiments it is possible to provide treatment between multiple applicators, (e.g.: multiple monopolar, unipolar and/or multipolar apparatus) or focusing of some energy sources (e.g.: RF, ultrasound, light), that may improve some treatment (e.g.: removing of fatty tissue).

Multiple treatment procedures and/or therapies may be combined at the same time. This improves the effectivity of the treatment and/or reduces the time needed for the treatment. It may also improve safety of the treatment e.g. stimulation of soft tissue by massage improves blood and lymph flow which in combination with RF (radio frequency) therapy leads to faster removing of treated fat cells (prevention of panniculitis), improves homogeneity of delivered energy and/or decreases influence of edge effects and overheating of some part of the soft tissue due to better body liquid circulation than applying RF without massage.

The apparatus may operate without any operator which saves time and money. One operator may supervise more than one treated patient. The self-operated device may prevent mistakes during the treatment caused by human factors. The self-operated device may also have a better response to changed conditions of the treatment and/or may provide more homogenous and precise treatment which improves results and safety of the treatment. With the apparatus controlled by a computer, responses to changed conditions are improved because the apparatus can react on e.g.: moving of the patient or some structural changes in the soft tissue, etc.; faster than 0.1 s, and human response is at least 0.5 s.

The apparatus may be modular with a belt and/or arrangement of the applicators providing an easy way to change treatment procedures and parameters before and/or during the treatment. One or more treatment applicators may be added or removed allowing for large scale treatment procedures, and modifying treatment parameters. Choosing suitable applicators may influence successful treatment. Each patient may have different body constitution with each patient consequently needing different parameters of a procedure and/or a different arrangement of treatment applicator(s), such as the number of applicators and/or types of applied therapy.

Large scale modularity by changing hardware and/or treatment pattern by placing of at least one applicator and/or other parts of the device, (e.g.: adding, removing, reorganization and/or changing of spacing between of at least one applicator and/or other part of the device) before and/or during the treatment allows actualization of the device and prevents obsolescence of the device. The belt may or may not contain supporting matrix. The belt may be flexible, whole or partly elastic and may be adapted to patient surface of arbitrary size and shape. This characteristic helps to provide optimal energy transfer from an applicator to the patient soft tissue. Improved contact with the patient skin or surface may decrease or prevent an edge effect, backscattering of delivered energy and/or provides better conditions for collecting feedback information. Supporting matrix may also be connected to upper side of the applicator, keep one or more applicators in touch with the patient surface, and not be in touch with the patient.

The belt may be a block of more than one applicator with and/or without supporting matrix and/or with or without spacing object. Location of individual applicators (optionally including different types of applicators) creates a hardware pattern. A computer and/or operator may choose several treatment therapies and procedures that can work simultaneously, with some overlay and/or sequentially during the treatment time and/or adjust one or more parameters of the procedure before and/or during the treatment.

Size of the applicator may be variable. Some of the applicator may have several square millimeters of active surface and some of them may have more than 10, 40, 50, 100, 200, 300, 500 centimeters square. Applicators may also have different shapes. Some of them may have active surface of symmetrical shape (e.g.: square, circular, elliptical, triangular, teardrop, rectangular, spidery and/or other types) and some of them may have asymmetrical shape of active surface.

Curvature of the active surface of the applicator may be different than curvature of other parts of the applicator. Active surface of the applicator may have regular (e.g.: convex, concave, flat, etc.) and/or irregular curvature (e.g.: partly spherical, pointy, wavy, with some ridge etc.), curvature of the active surface may also be composition of several different curvature and/or active surface of the applicator may have at some area different curvature than is curvature at another specific area of the same applicator. Curvature may create specific shape on the active surface of the applicator. Some types of applicator curvature may improve contact with the patient surface and/or modify pattern of deliver energy to the patient. Curvature of the active surface may also sets working distance of the applicator and/or may allow air (and/or liquid) flow under the applicator. In some embodiments the applicator curvature across its active surface may be changeable during the time and/or curvature may be used as massage elements, especially when active surface is designed with some pattern.

Massage of the patient soft tissue may be provided by suction mechanism that creates different air pressure above the patient skin and/or massage may be provided by different automatic mechanism than suction mechanism. Different manners of providing massage may be: mechanical massage by moving of at least one massage element; massage by switching between parts of the device that creates mechanical pressure, massage by stimulation muscle fibers by electrotherapy, massage by sound and/or ultrasound waves.

Active surface of the applicator may be designed from material that is able to adapt to any curvature of the body (e.g.: memory foam, elastic active surface of the applicator, and/or any other material). Active surface of the applicator may also contain one or more apertures of different sizes and shapes. Size and shape of one or more apertures may by variable during the time of the treatment. Applicators may have active surface from different types of materials, different curvature, size and/or shape in order to improve specific treatment (e.g.: improve energy transfer of specific treatment therapy into the soft tissue, improve contact of the applicator with patient body surface and/or other part of the device and/or in order to improve any parameter of the treatment. Active surface of the applicator may be modified before, during and/or after treatment procedure by interchangeable attachments and/or by changing between different types of thin spacing objects attached to active surface of the applicator.

Figure 21:
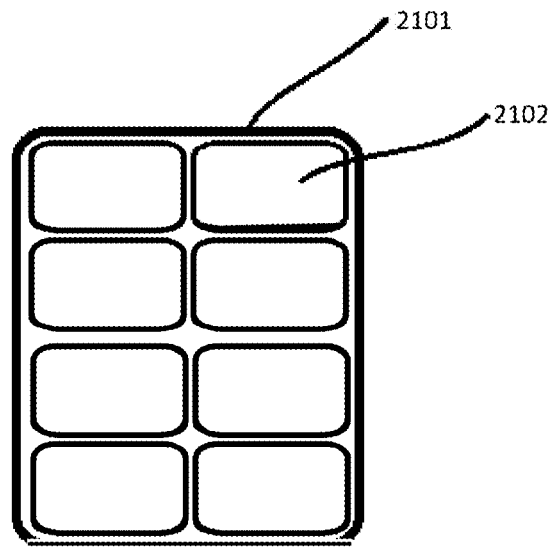
FIG. 21 is a schematic diagram of treatment elements in the applicator.

According another embodiment applicator may also create treatment pattern by switching on/off of some treatment elements included in the applicator. In FIG. 21 element number 2101 is the applicator's active surface with multiple treatment elements 2102. Applicator may contain different shapes of the treatment elements and number of the treatment elements in one applicator is not limited. Spacing between treatment elements may be different across the applicator's active surface. Treatment elements may also be movable during the treatment and/or spacing between treatment elements may also be variable during the time of the treatment. Switching on/off of some treatment elements during the time may be defined by protocol of the treatment procedure and may create multiple different types of the treatment pattern that may change during one treatment procedure. All of the treatment elements in one applicator may provide one therapy or in some other embodiment of the applicator, treatment elements of one applicator may provide different types of the therapies. Treatment pattern created by one applicator may also be created by moving of one or more treatment elements included in the applicator.

Attaching of one or more applicators to patient body, to spacing object, to supporting matrix and/or attaching of the supporting matrix to patient body, to spacing object and/or to other one or more parts of the supporting matrix and/or attaching other parts of the device together (e.g. treatment unit 2008 to a case or housing 2015 see FIG. 20) may be provide by one or more different manners and/or combination of manners described below. Attaching may be provided via adhesive polymer or copolymer (e.g. poly(styrene-ethylene-butylene-styrene) and/or others) which is located at the one or more contact sides of attaching parts of the device together and/or attaching one or more parts of the device to the patient surface.

In another embodiment parts of the device may be attached to patient body and/or to other parts of the device by a sticky layer between contact surfaces and/or by high adhesive layer applied on one or more contacts surfaces. Contact between parts of the device and/or between one or more parts of the device and patient surface may be provided by gravitational force, by high roughness of the contact surfaces, by electric forces, by magnetic forces, by rails, by elastic, partially elastic and/or non-elastic stripes, by Lace, by Velcro, zipper, by tacks, by creating lower air pressure between contact surfaces by suction mechanism, by interaction between polar and/or non-polar group of the contact surface, by fastening mechanism described below and/or by other physical, chemical, mechanical interaction between parts of the device and/or between patient surface. Some parts of the device may also be connected to each other by individual elements of a scaffold.

The belt may include supporting matrix that can hold one or more applicators and/or its treatment elements in touch with patient's body surface and/or it may also hold one or more applicators at an optimal working distance from the patient surface. The patient surface is typically the skin of the patient. However, the patient body surface may alternatively be some spacing object e.g.: clothing worn over the skin, a sheet, pad or other thin (0.1-2 mm) covering over the skin, and/or a thicker spacing object.

Spacing object may be located between any parts of the device and/or between patient and some parts of the device. Because of mechanical, structural, physical and/or chemical properties of this spacing object, spacing object may provide and/or improve attachment of any parts of the device and/or some parts of the device and patient body surface together.

The belt may encircle the patient's torso and/or limb, and optionally including a fastening mechanism that may have various embodiments and may help to fix applicator(s) to supporting matrix.

The supporting matrix may include fastening mechanism for attaching applicators to supporting matrix, for attaching some parts of the supporting matrix together, for attaching supporting matrix to spacing object and/or to patient's body and/or for attaching other parts of the device together. Fastening mechanism may also provide attaching one or more applicators to spacing object and/or to patient's body. Fastening mechanism may be e.g.: snap, clamp, some rails, adhesive polymer, pre-prepared holes, Velcro, zipper and/or other implemented fastening mechanisms and/or snap mechanisms) and/or may be provided by electromagnetic field, by magnetic field, by pressure lower than atmospheric pressure, by adhesive material, by interaction of chemical bounding interaction (interaction between polar and nonpolar groups) and/or others methods similar to method described above and/or other mechanisms.

The supporting matrix may contain fastening mechanism which may be permanent or removable from the supporting matrix. Position of the fastening mechanism may be variable and/or fixed before, during and/or after treatment. Fastening mechanisms may have various spacing between each other, different shapes, sizes and/or mechanism, how to be attached some of the applicators and/or how to be attached to supporting matrix and/or how to provide other types of the connection described above (based on physical, chemical and/or mechanical interaction). Fastening mechanism may be attached to supporting matrix and/or to arbitrary other part of the device at arbitrary location by similar manner as it is described above-attachment of the applicator to patient's body and/or to spacing object. Fastening mechanism may be also attached to supporting matrix and/or other parts of the device by mechanical connection.

One applicator may be attached across multiple fastening mechanisms (e.g.: applicators provide mechanical massage with movable and/or static element, RF therapy and/or other applicators provided different and/or multiple types of the therapies). It is not necessary that supporting matrix encircling whole patient torso and/or limb etc. In some embodiments applicators may be attached to both sides of the supporting matrix.

The belt may comprise applicators applied on the patient surface and/or a thin and/or a thicker spacing object and fixed by textile, polymeric and/or other strips. The strips may be at least partially elastic. The applicator(s) may be attached at the right working distance by one or more stripes located in front and/or back side of the applicator. Suitable elastic materials are elastomers or also elastic fabrics. The elastic belt material also adapts to respiratory movements and/or other movement of the patient.

The applicators may have different sizes and shapes, to improve treatment results and/or flexibility of the belt. Each applicator may be fixed to supporting matrix at arbitrary position e.g.: by inserting an applicator into the pocket in the support matrix, by Velcro and loop tape, by one or more magnets, by tacks or fasteners, fastening straps and/or by other fastening mechanism as may be seen in FIG. 19 and/or by other manner described above.

The supporting matrix may be attached to the patient by different way described above and/or by encircling patient body and connect some parts of supporting matrix to each other and/or by external positive pressure acting on supporting matrix in direction to the patient surface. Supporting matrix may be designed as one or combination of more pieces where at least one piece has elastic properties. Supporting matrix may be designed as elastic clothes (e.g. elastic trousers, sleeves, shirt etc.) to fix one or more applicators at optimal location on the patient body and/or at optimal working distance with the patient body at the right position. Supporting matrix may be fixed at specific body location of the patient body and/or may be movable along the patient body.

Some parts of the supporting matrix may be created of flexible, elastic and/or rigid materials e.g.: polymeric materials, ceramics, textile materials, conductive parts and/or other materials. The supporting matrix may be at least partially flexible and/or elastic to provide improved contact with the patient body and/or set appropriate working distance for one or more applicators.

The support matrix may also contain apertures of different sizes and shapes. The support matrix may contain cooling/heating elements, massage elements that may move across the belt area and/or one or more sensors. In some embodiment mechanism for moving with attached applicators and/or other part of the belt may be provided according defined pattern. A track or path for the applicator may be created by rails (e.g.: applicator may be moved along them by mechanical forces based on pressure and/or tensile forces) and/or by a path created from conductive elements and applicators may be moved along them by electric, magnetic and/or electromagnetic forces.

Moving of one or more applicators and/or other parts of the belt across the patient body may also be provided by moving of the supporting matrix. Move of the supporting matrix may be provided by expansion and/or shrinking of some parts of the supporting matrix and/or by moving with the supporting matrix along the spacing object (e.g. by mechanic, electric, magnetic and/or combination of these forces) and/or by attaching supporting matrix to an another movable parts of the device (e.g.: mechanical arm, construction on rails).

Figure 19:
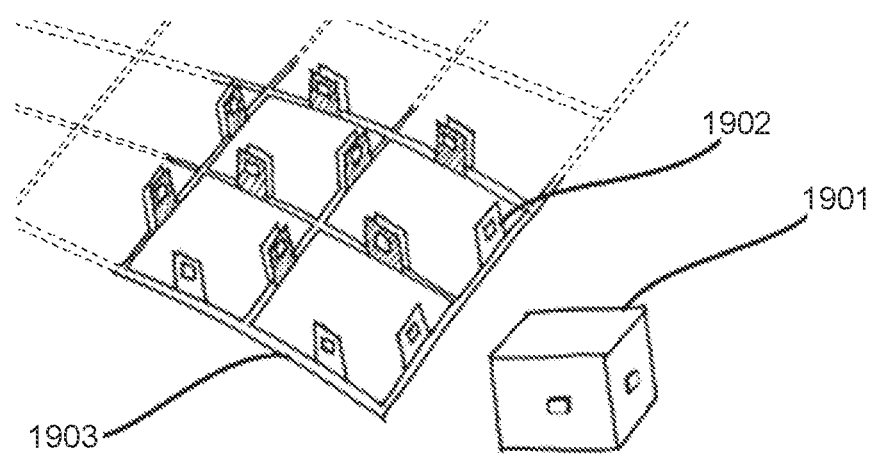
FIG. 19 is a partial perspective view of an embodiment of the belt providing hardware pattern.

The supporting matrix may have several embodiments. One of such embodiment is depicted in FIG. 19 where the support matrix consists of guiding scaffold 1903, with the one or more applicators 1901 attachable to the scaffold 1903 by fastening mechanism 1902. The supporting matrix may include conductive parts that may provide communication between applicators, communication between applicators and central control unit and/or communication between at least one applicator and treatment unit. Conductive parts in the supporting matrix may also provide power supply to the applicator(s). Applicator may also include one or more rechargeable batteries as a source of energy. These batteries may be recharged through the supporting matrix and/or through the spacing object.

In another embodiment belt may be a flexible textile and/or polymeric sheet. This sheet may contain conductive elements that may provide communication, power supply, determine of one or more applicators location and type, contact with the supporting matrix and/or patient surface, provide information about treatment protocol as was mentioned above and/or other features. In some embodiments supporting matrix may also include cooling and/or heating components. This embodiment of the belt may also include spacing object.

Feedback information may be collected by different types of sensors and may have different characters e.g.: biological, chemical, physical etc. One or more sensors may be located in the belt (in supporting matrix and/or in the one or more applicators) and/or externally out of the belt (e.g.: optical, sound and/or others located around a patient). One or more sensors may control parameters of the treatment procedure e.g.: intensity of delivered energy into the tissue, burst rate, changing parameters of the delivered signal and/or switching on/off of different treatment procedures and/or others. The device may contain different types of sensors for monitoring device parameters, monitoring of body biological, physical, chemical and/or other parameters (e.g. an electrochemical sensor; a biosensor; a biochemical sensor; a temperature sensor; sensor for measuring distance of applicator from the patient surface, from some area of the patient soft tissue and/or from other applicator (determine position of the device); a sensor for recognition of applicator orientation in 3D; rotational orientation sensor; a sorption sensor; a pH sensor; a voltage sensor; a detector of moving velocity and/or change of position; photo sensor; sensor measuring fluid viscosity; a camera; a sensor for measuring fluorescence of the patient surface; a sound detector; a current sensor; sensor for measuring of specific heat capacity of human/animal tissue; a sensor for measuring value of magnetic field; sensor for measuring impedance; permittivity; conductivity; susceptibility and/or any suitable sensor or sensors measuring biological parameters and/or combination thereof e.g.: sensor for measuring dermal tensile forces; sensor for measuring the activity of the muscle; a sensor for measuring muscle contraction forces; sensor for measuring pulse of the patient; a sensor measuring skin elasticity. The device may also include at least one contact sensor for monitoring applicator contact with body surface of the patient. Supporting matrix may also recognize type and/or location of the different one or more applicators attached to the supporting matrix.

As a result, so-called plug and play methods may be used to modify hardware pattern of the applicators attached to patient and/or to supporting matrix (sorting and/or choosing of the applicators). This plug and play method provides a large scale of modularity. The supporting matrix also may recognize which applicator is positioned or fixed in which slot in the supporting matrix and the control unit may assign and/or accept predefined treatment protocols. Recognition of the applicator may also be provided by one or more central control units and/or by any other one or more control units. Localization of the applicator may be provided by some specific sensors described below.

Figure 18:
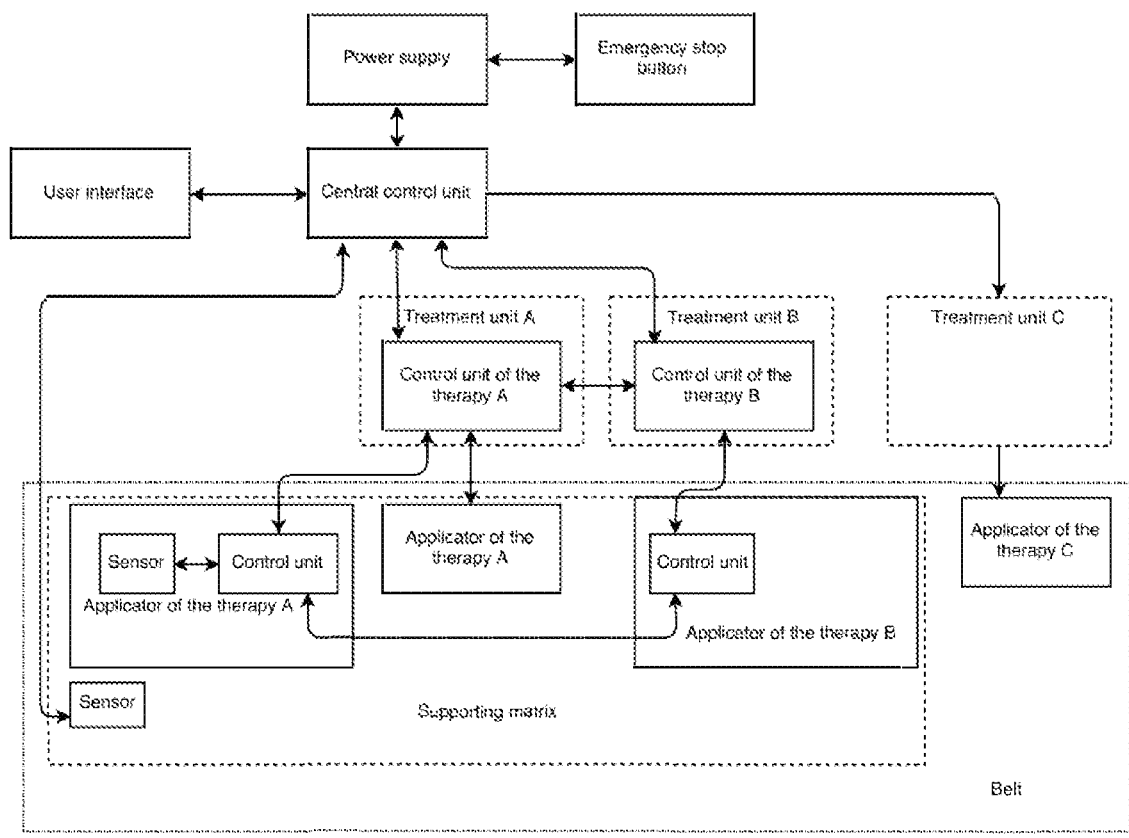
FIG. 18 is a schematic diagram of the present apparatus or system.

Applicators may be able to communicate with each other and/or with central control unit see FIG. 18 by wire and/or wirelessly. This communication may provide information from feedback sensors, about position of one or more applicators, 3D orientation of the applicator(s), information about contact of the applicator(s) with the patient, distance from the patient surface, parameters of the treatment procedure, parameters of each applicator and/or other information from one or more sensors. Data from a different applicator may provide complex information about the treatment and/or treated soft tissue. Information from the sensors may be used to determine which part of the patient is treated, determine the exact composition of treated soft tissue and/or changes in the soft tissue during the time of the treatment.

These sensors may cooperate with one or more applicators (e.g.: provided ultrasound, RF, electro-magnetic source of energy) and may be used as imaging device of surface and/or deeper layers of the patient soft tissue. Imaging system of the soft tissue before and/or during the treatment may improve safety of the treatment, determine when the treatment is complete, and/or monitor process and/or progress of the treatment. This processed data may be used for adjusting parameters of the treatment procedure, may activate other treatment therapies and/or one or more procedures (activate massage, cooling, heating and/or others) and/or change any other parameter of the treatment. This data may also warn operator and may be used as prevention of health risk.

Treatment procedures may include several instructions that define treatment of one applicator. Treatment procedures include e.g.: define one or more applied therapies, shapes and types of a delivered signal into the soft tissue (symmetrical; asymmetrical; polarized; non-polarized; continual or sequences of signal pulses; timing of the delivered signal; shape of the signal: sine, square, triangle, saw tooth and/or others), define pulse sequences intensity of delivered energy, polarization of delivered electro-magnetic signal, remaining time of treatment procedure, threshold parameters, time and/or sequence of heating/cooling of the soft tissue and/or other parameter that influence treating of the soft tissue by one applicator (e.g.: geometry and position if it is possible to change this parameters and/or other parameters).

Figure 17:
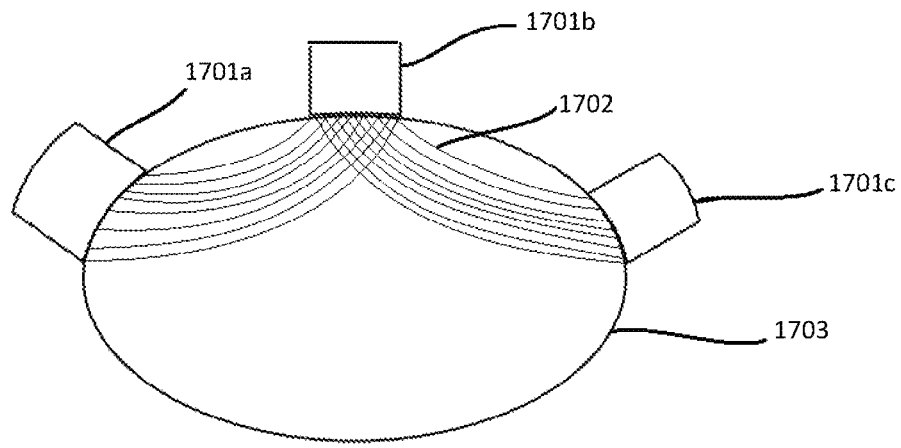
FIG. 17 is schematic representation of cooperation multiple applicators across the patient body.

Several applicators may cooperate with each other. FIG. 17 describes cooperation of multiple applicators 1701*a*, 1701*b*, 1701*c* that may provide some treatment therapy (e.g. multipolar RF therapy symbolized by field lines 1702 and/or others) to the patient 1703. Cooperation of multiple units may be used for different therapies (e.g.: RF, ultrasound, light, massage, cooling/heating, electrotherapy, magnetotherapy and/or other therapies) in order to provide bipolar and/or multipolar treatment across large patient area, better targeting of delivered therapy, better focusing of delivered signal, creating of some gradient in the soft tissue (e.g. thermal gradient, etc.), better homogeneity of provided therapy across large patient area and/or volume of the soft tissue.

Cooperation of multiple applicators and/or treatment elements may enlarge treatment variability (e.g. treatment depth, focusing), since the electrode of each applicator and/or treatment element may represents one pole of multipolar treatment.

In order to provide safe multipolar treatment across multiple applicators this process may be guided by one or more central control units and/or by at least one control unit of the treatment unit and/or by external control unit in cooperation with sensors and other information (e.g.: placement and distances between specific 5 types of the applicators). This method may provide safe and targeted treatment.

Communication between applicators, central control unit, other control units, user interface, and/or other parts of the device may be based on peer to peer principle and/or communication may be based on master/slave model where one of the units has higher priority than others and manages the treatment. Higher priority may also have a group of more than one control unit and/or the highest priority may be redirected to one or more others units during the treatment. Redirection of the highest priority may be based on feedback information, treatment protocol and/or operator guidance.

A central control unit which may be guided by internal protocol and/or by user interface. Based on this information the control unit in each applicator and/or control unit of the therapy (see FIG. 18) may change treatment parameters. FIG. 18 also symbolize mechanical Emergency stop button that unplug device or only parts of the device, that provides energy to the patient, from the power supply by manner that stops all therapies and switch off the device by safety way. Switching off one or more therapies and/or some parts or all parts of the device may be guided by control unit with the highest priority.

The operator may change and/or set one or more treatment parameters and procedures through the user interface located on base unit that may include central control unit and/or on the treatment unit that may include control unit of the therapy. The operator may change, set and/or adjust any treatment parameters and/or procedure before and/or whenever during the treatment. Software controls safety of the treatment parameters and if some of them are valued as dangerous, software warn the operator and propose safety one. If a sensor detects critical value of specific parameter (e.g.: temperature, time, dosage intensity and/or others), operator may be warned and/or the procedure and/or treatment parameters are changed according predefined safety protocol.

Software may include different specific safety protocols and others may be created. The user may also be able to select one or more of predefined treatment protocols and/or operator may create a new treatment protocol. Treatment protocol includes data about treatment (e.g.: treatment parameters, procedures, localization and/or orientation of each applicator, information about treated body and treated areas of the body). The control unit may be able to learn in order to modify and improve treatment protocols based on analysis of stored data from previous one or more treatments.

Figure 20:
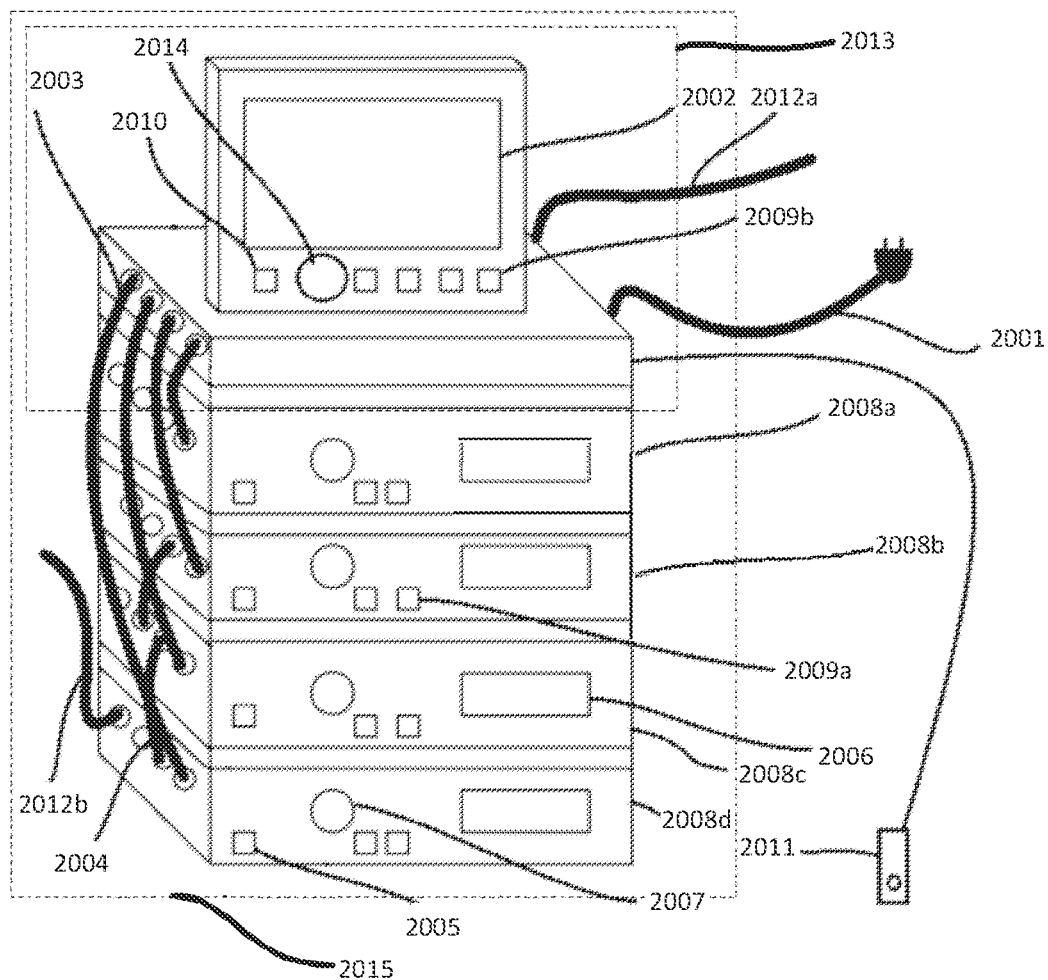
FIG. 20 is schematic representation of one embodiment device modularity

In FIG. 20 a case 2015 contains central unit 2013 of the case 2015 and one or more treatment unit (2008a-2008d) that may contain one or more control unit of the therapy. The central unit 2013 of the case 2015 as the only one may include one or more central control units. Case 2015 may include slots for specific treatment units. Treatment unit may be fixed in the right position by specific type of fastening mechanism that is described above. Connection between case and treatment unit may be wireless, by cable 2003, by contact pins, one or more magnets, one or more conductive parts and/or by chassis. Recognition of the treatment unit may be through specific impedance, RFID tag, pins, sequence of specific electrical and/or electromagnetic pulses measuring of magnetic field that may be specific for individual type of the treatment unit, software recognition and/or through other one or more mechanisms. Described system for recognition of the treatment unit may also be used for recognition of individual applicator.

According to still another embodiment the case 2015 may provide one or more treatment therapies without connecting to one or more treatment units 2008.

Central unit 2013 of the case 2015, applicator(s) and/or one or more treatment unit (2008a-2008d) may contain emulator software and/or hardware to provide communication between each other and/or an external device.

Number of units that are able to communicate between each other is not limited. Each of these units may provide software and/or hardware for controlling and/or providing one or more specific therapies.

The therapy (e.g. RF, ultrasound, and others) may be controlled through the specific treatment unit or units (2008a-2008d) for this therapy by human-machine interface, by some protocols that may be included in one or more central control units and/or other control units and/or through external protocol.

Human-machine interface may include user interface that may be included in one or more treatment units (e.g.: circle control element 2007 may have rotational and/or pushing controlling function treatment; some buttons 2009a, secondary display 2006 may be touch; button 2005 which signal if the unit 2008a-2008d is switch on or off and/or others) and/or user interface include in central unit 2013 of the case 2015 (e.g.: circle control element 2014; several buttons 2009b; primary display 2002 may be touch; emergency stop button 2010 and/or others). The device may also have external human machine interface. The device may also include external emergency stop button 2011 for the patient when the patient feels uncomfortable.

Information about attached applicators, parameters of the therapy(s) and/or procedure(s) may be displayed on the secondary and/or primary display. Some parameters of specific therapy may also be adjusted and/or changed by other one or more treatment units that are not intended for this therapy. Unit 2008a-2008d may be connected by cable 2012b and/or wirelessly to belt and control it. Unit 2008a-2008d may also be connected to other one or more treatment units by cable 2004 and/or wirelessly and/or may be connected to central unit of the case 2013, by cable 2003 and/or wirelessly.

Through the central unit 2013 of the case 2015 may be controlled all parameters of the treatment. The central unit 2013 of the case 2015 may be connected to belt wirelessly and/or by cable 2012a. Each part of the device that is needed to be provided by power supply may be connected to other part of the device that is powered and/or may be connected to power supply by cable 2001.

Separation of treatment unit(s), and/or other part of the device may be very effective system for improving modularity. During the time it is possible to invent new treatment devices, applicators, methods and/or protocols that can be in easy way implemented in new specific unit similar to unit 2008a-2008d and connect to presented method and device. The central control unit, control unit of the therapy and/or other control units may be designed for software update through the cable and/or wireless connection (e.g. through internet network, actualization device and/or other methods). The device may also be able to download new software, treatment protocols and/or other parts of the software. Device may also be interconnected with some other devices (e.g. computers, tablets, smart phones) that may help operator to control treatment and adjust it with limited manner. It may be also possible to check proper functioning through the internet by authorized person.

The device may also include counter. The counter is a part of the device that is able to count number of therapies, time of providing specific one or more therapies, parameters of treatment(s) and/or treated patient, number of cycles of specific one or more therapies and/or other measurable properties connected to the treatment. Data from the counter may be saved into the memory that may be accessible only for authorized one or more persons and/or data from the counter may be sent by network to external storage. The device may also communicate with one or more other devices and/or with human/machine interface and inform user and/or authorized person about actualization, service, about billing system, about wear of specific parts of the device etc.

The counter may also contain unit that is able to provide test of the functionality of the device and/or measuring response of some parts of the device.

The device may also be equipped or connected to some device that is capable to demonstrate patient process and/or progress of the treatment and/or compare running treatment with previous treatment of the same person or to other persons.

The present device and method may provide different types of energies in order to provide treatment as described above. The device preferably uses an RF treatment energy source.

Waves of the RF energy may be delivered in the range from 0.1 MHz to 2.5 GHz or from 0.1 MHz to 300 MHz or from 0.1 MHz to 100 MHz. The RF energy may be provided in one, two or more frequencies to a patient's body simultaneously or sequentially. Such energies may be provided by one or more different sources of energies e.g. based on capacitive and/or inductive RF electrodes.

According to one embodiment and a method of use, an experiment proved significantly improved treatment results when at least one monopolar electrode produced RF energy up to 1.5 MHz and at least one pair of bipolar electrodes produced RF energy in range from 20 MHz to 35 MHz.

According to another embodiment and method of use at least two different RF energies may be simultaneously provided to patient's body at frequencies in range from 25 MHz to 30 MHz.

According to another embodiment treatment RF energy may be modulated to frequencies in a range from 50 kHz to 1 MHz or from 50 kHz to 500 kHz or from 100 kHz to 300 MHz.

Different RF frequencies may be used during one treatment session, targeting different soft tissue structures and soft tissue depths.

According to another embodiment, RF waves in microwave range from 300 MHz to 300 GHz may have several benefits namely in combination with dielectric material 601a located between treatment energy source and patient's soft tissue surface. Advantages and parameters of treatment may be used as described in U.S. Provisional Application No. 62/331,072 incorporated herein by reference.

According to some embodiments, instead of RF electrodes, one or more waveguides and/or antennas may be used that enable the use of RF frequencies up to 2.5 GHz.

An electromagnetic field may be applied to the patient body in continual and/or pulse modes. Continual irradiation of a body area by RF may be at least 5 s or 20 s or 30 s or 60 s or 120 s or 240 s or 10 minutes or 20 minutes or more than 20 minutes or the most preferably more than 35 minutes.

The pulsed electromagnetic field may last between 50 μs to 100 s, in more preferred protocol pulse may last between 1 s to 70 s, and in the most preferred embodiment pulse may last between 3 s to 70 s.

An RF treatment energy source may be adjacent to the patient's soft tissue in contact mode where RF treatment energy source (electrode) is in contact with the patient's surface, indirect and/or in no-contact mode, i.e., with the electrode not in contact with the patient surface.

Energy flux density (energy flux density on the electrode surface) of the electromagnetic field in noncontact mode, where electrodes providing RF signal are spaced from the patient body by an air gap may be preferably in the range between 0.01 mW·mm$^{-2}$ and 10 W·mm$^{-2}$, more preferably in the range between 0.01 mW·mm$^{-2}$ and 1 W·mm$^{-2}$, most preferably in the range between 0.01 mW·mm$^{-2}$ and 400 mW·mm$^{-2}$.

Energy flux density of the electromagnetic field in contact mode (including the direct contact of electrodes coated by thin layer of insulator) may be preferably in the range between 0.01 mW·mm$^{-2}$ and 2000 mW·mm$^{-2}$, more preferably in the range between 0.01 mW·mm$^{-2}$ and 500 mW·mm$^{-2}$, most preferably in the range between 0.05 mW·mm$^{-2}$ and 280 mW·mm$^{-2}$.

Energy flux density of the electromagnetic field in non-contact mode where electrode is spaced from the patient body by dielectric material with beneficial dielectric parameters e.g.: using a spacing member such a flexible container holding a bolus of water, silicon and/or others dielectric materials) may be preferably in the range between 0.01 mW·mm$^{-2}$ and 500 mW·mm$^{-2}$, more preferably in the range between 0.01 mW·mm$^{-2}$ and 240 mW·mm$^{-2}$ or even more preferably in the range between 0.01 mW·mm$^{-2}$ and 60 mW·mm$^{-2}$ or the most preferably in the range between 0.05 mW·mm$^{-2}$ and 12 mW·mm$^{-2}$.

RF electrode may operate in capacitive and/or inductive mode. According to preferred embodiment capacitive mode providing selective and safe treatment may include RF-regulating system (see FIG. 11). RF-regulating system may be part of the energy generating unit 105, control unit 103 and/or may be located individually and may communicate with control unit 103.

Parameters of RF treatment energy may be also modulated (adjusted) as described in U.S. Provisional Application No. 62/333,666 incorporated herein by reference. According alternative embodiment applicator may be movable as described in U.S. Provisional Application No. 62/331,088 incorporated herein by reference.

Figure 22:
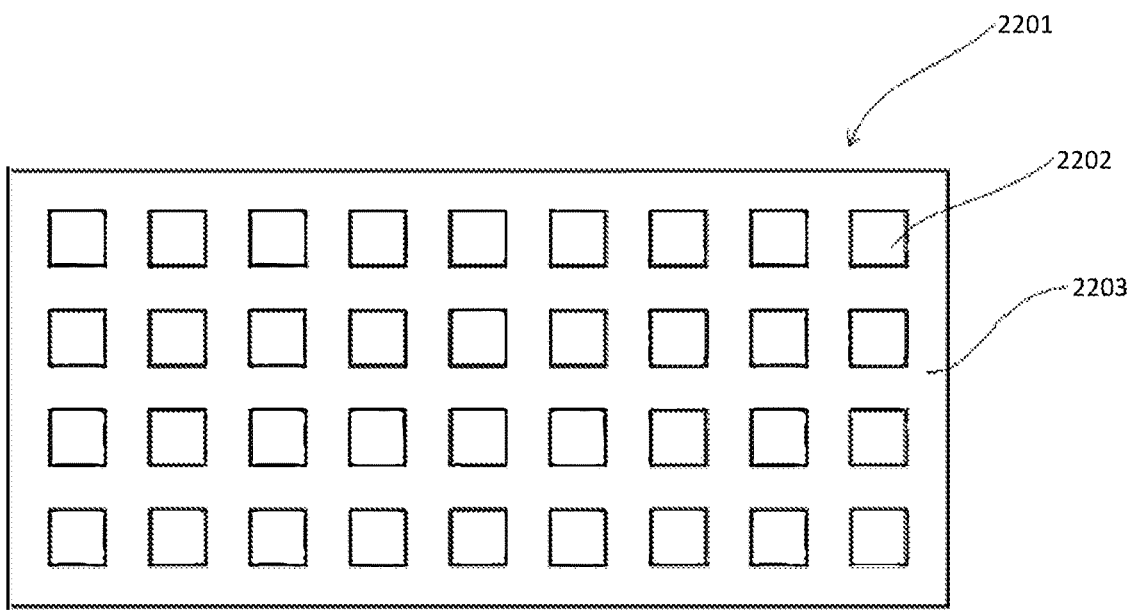
FIG. 22 is schematic diagram of arrangement of electrodes into a matrix.

As shown in FIG. 22, a system is provided for treating large areas or parts of the body 2201 with minimal need of personnel assistance during therapy. Multiple electrodes 2202 may be arranged adjacent to each other, with the electrode interconnected and partially separated from each other by carrier surface 2203. If the electrodes are made of rigid material the spacing between the electrodes allows for flexible positioning of the electrodes on the body 2201. However, preferably the electrodes are made from flexible material. The electrodes can be selectively switched on and off during treatment, optionally in a way so that adjoining electrodes are not powered on at the same time. This switching, if used, may be controlled by the microprocessor control unit and be set by the user in a user interface, or it may be set automatically based on treatment type.

The new methods include application of radio frequency waves of various waveforms that are delivered to the treated tissue. Some particular examples of these waveforms with varying parameters are shown in FIG. 23-28. The waveforms are generally described for one source of electromagnetic power. However, more than one source may work in these modes. The waveforms being just a schematic representation of field oscillations in time, they may be related to both electric and magnetic part of the electromagnetic wave. The peak amplitudes and instantaneous amplitudes shown in FIG. 23-28 can thus represent either the electric or the magnetic field strengths and for sake of simplicity, they will be denoted just as peak or instantaneous amplitudes in further descriptions.

Figure 23A:
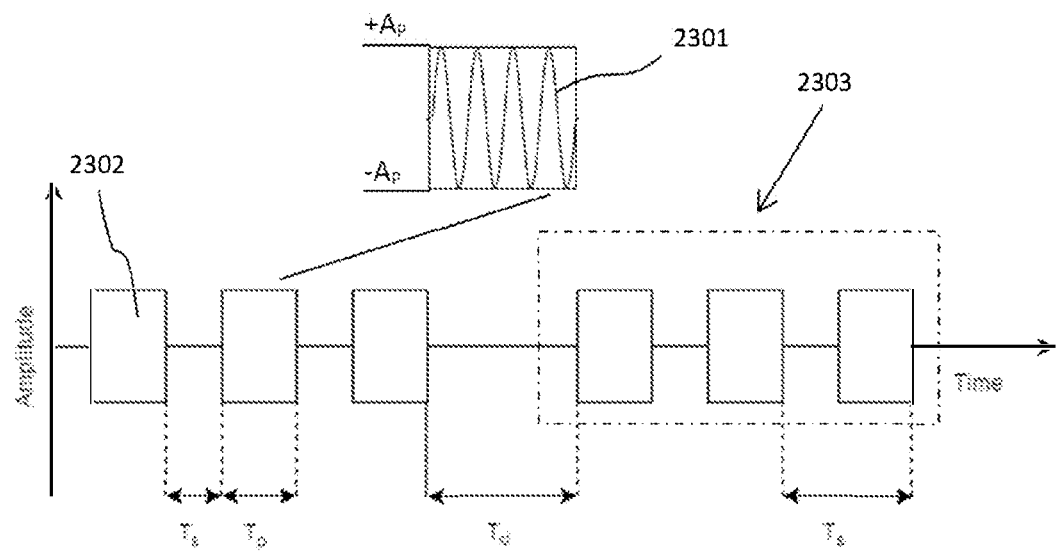
FIG. 23a is a plot of electromagnetic pulse sequences.

FIG. 23a is a schematic plot of instantaneous amplitude of an electromagnetic wave against time in the simplest pulsed mode. Pulse duration Tp determines the time when the source of radio frequency radiation is on. Within the pulses 2302, a sine wave 2301 of a predetermined frequency is delivered, oscillating between the positive and negative value of peak amplitude Ap. Pulse spacing Ts is the period when the source of radio frequency radiation is off between two subsequent pulses 2302. Cycle time Tc can then be expressed as Tc=Tp+Ts. Duty cycle D is the ratio of the ON time to the total ON plus OFF time for one complete cycle of operation, in other terms: D=TP/(TP+TS). A dwell time Td between two groupings of pulses may also be introduced. For the sake of simplicity, a grouping 2303 comprising only 3 pulses is shown in FIG. 23a. However, the real number of pulses per grouping is much higher, and in many applications, the pulses are delivered continuously, spaced by regular intervals Ts, i. e. with Td=0.

The peak amplitude Ap, the frequency, the pulse duration Tp and the pulse spacing Ts, and thus the duty cycle D, can be varied and/or adjusted during the therapy. The number of pulses per grouping of pulses and the dwell time between two subsequent groupings can be varied as well.

Peak amplitude and frequency values and their possible variations during the therapy will be discussed in the next sections.

Figure 23B:
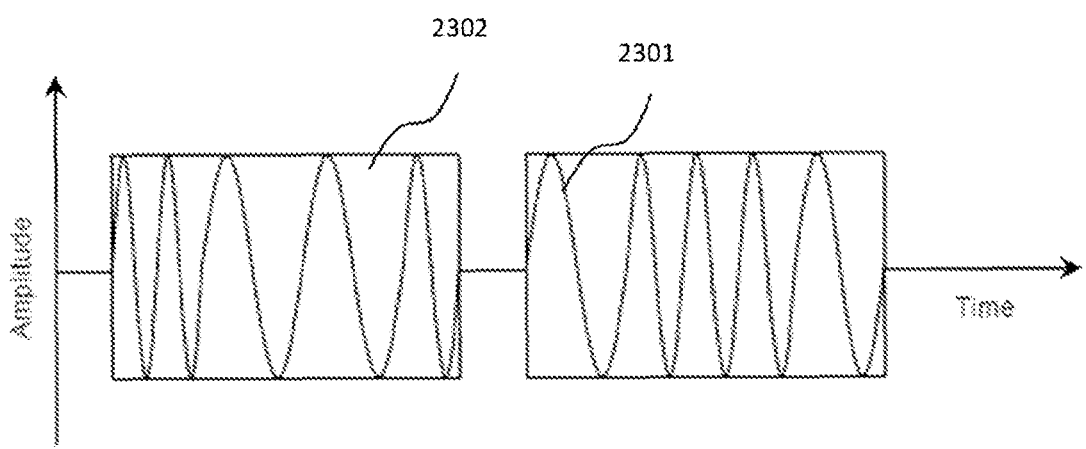
FIG. 23b is an example of frequency modulation within a pulse.

In special cases, the frequency can be modulated within the pulses 2302, as shown in FIG. 23b.

Figure 23C:
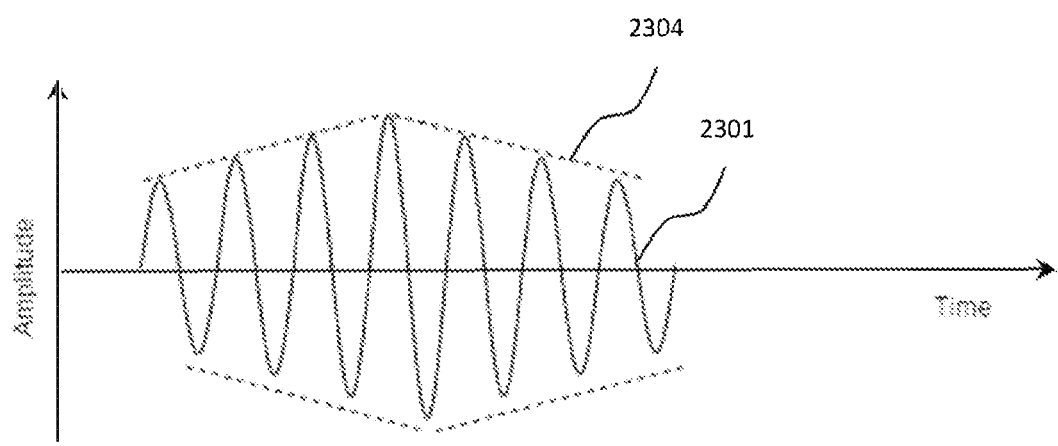
FIG. 23c is an example of amplitude modulation within a pulse.
Figure 23D:
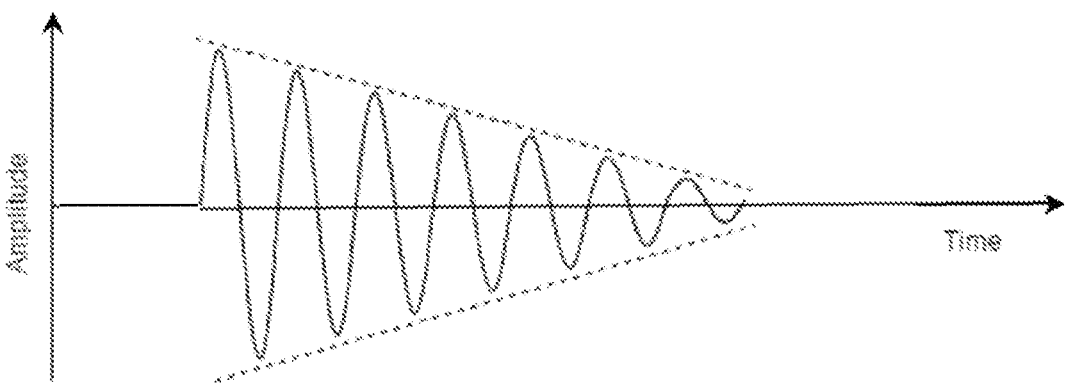
FIG. 23d shows one of the possible modifications of leading and trailing edges of a pulse envelope.

Amplitude modulation, i. e. the modulation where the peak amplitude Ap changes over time, can also be used in pulsed mode. In this case, signal envelope 2304 is defined as a smooth curve outlining the waveform extremities, as shown in FIG. 23c. Whereas the signal envelope in FIG. 23a is a rectangle, in FIG. 23c the signal envelope 2304 forms a part of a sine wave 2301. Other signal envelope forms are also possible, e. g. triangle, saw tooth or many others. Similarly, the envelope of an ideal rectangular pulse shown in FIG. 23a can be intentionally modified by changing the form of the leading edge from very steep to rising more slowly. The trailing edge can also decay more slowly, as shown in FIG. 23d.

Both frequency and amplitude modulation and the forms of envelopes and edges, can be varied according to the temperature and/or impedance feedback, previous experience and the desired therapeutic effect.

The pulses as shown in FIG. 23a are alternated with simple pauses. In another aspect of the invention, they can be alternated with active cooling of the adjacent parts of the body, which is useful especially for the treatment of tissues at depth.

Figure 24:
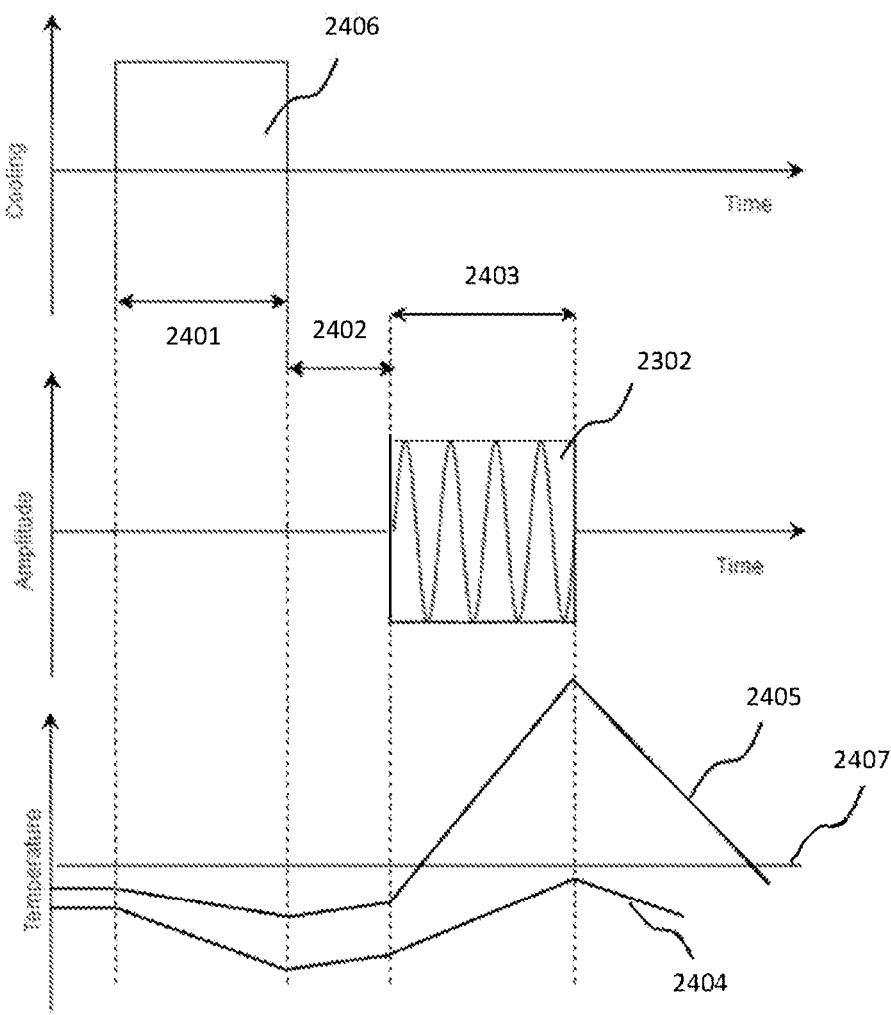
FIG. 24 is a plot of one example of pulsed cooling alternating with electromagnetic pulses, showing also the evolution in time of temperatures at surface and at depth.

FIG. 24 shows schematically an example of pulsed radio frequency heating and alternating cooling as a function of time, with resulting time evolution of the first temperature 2404 at the skin surface and of the second temperature 2405 at depth. It is only a schematic illustration of the procedure, the precise data depending on many tissue and electromagnetic radiation related parameters. The pulsed radio frequency heating 2302 is applied during time interval 2403, following the cooling time interval 2401. As an option, a short delay 2402 may follow the cooling period before the heating pulse starts. Such alternating sequences of cooling and heating may be periodically repeated.

When the surface of the skin is exposed to an active cooling 2406, the first temperature 2404 at the skin surface drops to a level determined by the cooling time interval 2401. The second temperature 2405 at depth is initially not significantly affected by the cooling and may drop only slightly. When the heating pulse is on, the second temperature 2405 at depth rises, while the surface tissue is still kept below the threshold 2407 for damage temperature, due to the precooling and/or to the depth and/or tissue selective parameters of radio frequency pulse.

Besides the pulsed cooling mode shown in FIG. 24, a permanent cooling is also possible. As another option, permanent cooling to a higher temperature (e.g. 36° C.) may be associated to a pulsed cooling to a lower temperature (e.g. 30° C.). As yet another option, permanent cooling to a lower temperature may be associated to a RF heating to a higher temperature.

Figure 25:
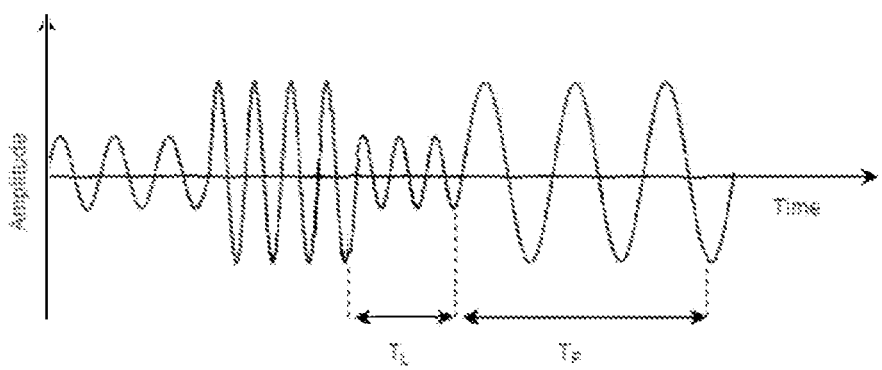
FIG. 25 is an example of preheating followed by pulses of higher power alternated with pulses of lower power.

In yet another aspect of the invention, radio frequency heating with lower power and/or different frequency and/or different wave amplitudes may also be applied during pulse spacing Ts periods, as shown in FIG. 25. The reduced power and/or modified frequency TL between the main pulses TF help to prevent overheating. Also, other structures at different depths can be heated by these intermittent radio frequency waves. One or more sources of radio frequency waves may be employed to achieve this effect.

Pulsed therapy is preferentially continuous, in the sense that the pulses follow each other fluently with regular pulse spacing Ts and the dwell time Td can be set to 0, as there is generally no need to interrupt the treatment for overheating, which is sometimes the case with continuous radio frequency waves.

Pulsed radio frequency mode, especially when used with temperature and/or impedance measurement feedback, offers the advantage of efficient heating and/or stimulation of the targets at depth, without the surrounding tissue destruction and painful sequelae. These side effects are sometimes associated with continuous radio frequency therapy when it is used to heat the deeper layers of the skin. As the tissue heating decreases rapidly with the distance from the radio frequency source, relatively high powers are necessary to achieve therapeutic temperature at deeper layers of the skin.

In continuous mode, these high powers can cause tissue destruction especially in tissues having higher water content and thus higher radio frequency wave absorption, as the epidermis or dermis. Standing waves leading to hot spots creation represent another drawback of the continuous radio frequency therapy. When the pulse therapy is properly adjusted, the hot spot creation is nearly excluded, and due to the pauses between the high power pulses, harmful heat-induced effects which would arise with the same high power applied in continuous mode, are avoided. The reason is that during the pauses between the high power pulses, the radio frequency heating works at reduced power or is completely off. Active cooling of the surrounding tissues can also be employed. The pulse spacing Ts provides time for heat elimination, generally keeping the surrounding tissues below the damage temperature. The preferred pulse spacing Ts is less than or equal to the thermal relaxation time of a targeted structure.

Figure 26:
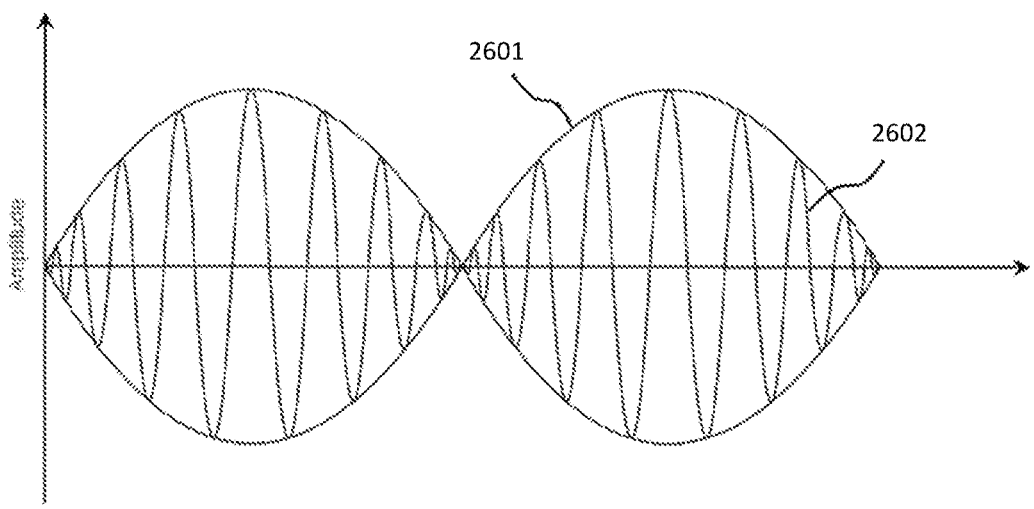
FIG. 26 illustrates an amplitude modulated wave having a sine envelope.
Figure 27:
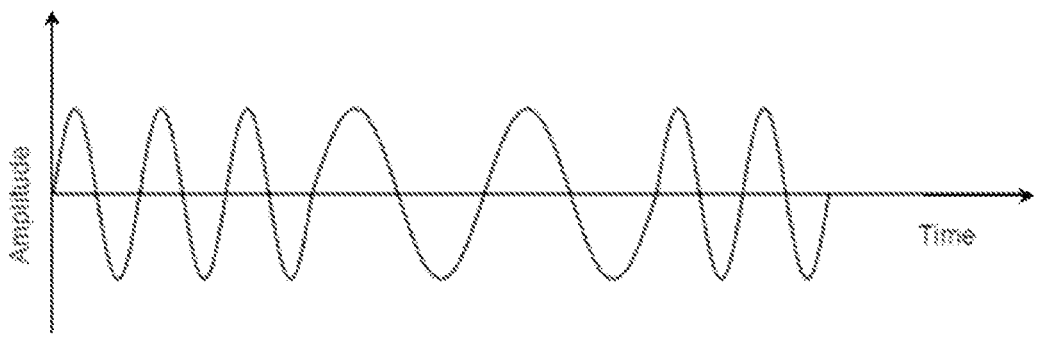
FIG. 27 illustrates a frequency modulated wave.

Amplitude or frequency modulation, as they were described within individual pulses in the pulsed regime, can be employed in continuous mode as well. This represents a supplementary tool to adjust the penetration and heating efficiency parameters of the radio frequency waves. An example of amplitude modulation of a continuous wave 2602 with a sine envelope 2601 is shown in FIG. 26. An example of frequency modulation of a continuous wave is shown in FIG. 27. Other envelope forms are also possible, as well as different indexes of the frequency modulation.

Even if there is no frequency modulation, the frequency can be advantageously adjusted to different values during different intervals of the treatment. This frequency variation may be used to enlarge the possibilities of all the above described modes, and also in continuous mode.

It has been found that the higher the frequency, the more enhanced the effect of power intensity on the tissue and the faster the heating, which is true in particular for polar tissues such as dermis, epidermis or muscles. The reason is that the high frequencies are strongly absorbed and thus quickly transformed into heat in polar tissues. As a result, microwave frequencies, e. g. 2.4-2.5 GHz, are well suited for epidermis and dermis tissue heating, and also for muscle diathermy if the power is sufficiently high even after absorption in the more superficial skin levels. However, in some conditions, e. g. for higher powers needed to penetrate really deep layers, the heating of superficial tissues by microwave frequencies might be excessive, which would discourage the use of these high-frequency microwaves in continuous mode without cooling. Proposed solutions to this problem include: lowering the frequency e. g. to 902-928 MHz or even lower, or switching on the active cooling or passing from the continuous mode to the pulsed mode.

It has been found that the depth of penetration decreases with frequency, and namely those frequencies of 902-928 MHz or lower can penetrate more deeply into the tissues than the microwave frequencies. The advantages of lower frequencies for diathermy include less severe standing waves and less resulting hot spots in the fat, and better knowledge of the absorbed energy for a large variation of skin layer thicknesses, as the temperature distribution in the tissues is more uniform at frequencies of 902-928 MHz or lower. However, heating at lower frequencies is slower.

The non-polar tissues, e.g. the adipose tissue, are also heated slightly faster at higher frequencies. The adipose tissue being situated just beneath the relatively thin layer of epidermis and dermis, the overall absorption of high frequency waves in these superficial layers is moderated and it appears that micro wave frequencies, e. g. 2.4-2.5 GHz, are well suited for fast adipose tissue diathermy. However, shorter frequency waves might also be attractive for adipose tissue heating in some cases.

The shorter frequency wavebands that may be used for frequency variation include the following ranges: 902-928 MHz, 433.05-434.79 MHz, 40.66-40.70 MHz, 26.957-27.283 MHz or 13.553-13.567 MHz.

In yet another aspect of the invention, the power of the radio frequency waves can also be advantageously adjusted. This adjustment can be performed in continuous mode or in any of the modes described above, including their mutual combination. It is well known that the power is linked to the amplitude of electric or magnetic field strength, these amplitudes being schematically plotted in FIGS. 23-28.

Figure 28A:
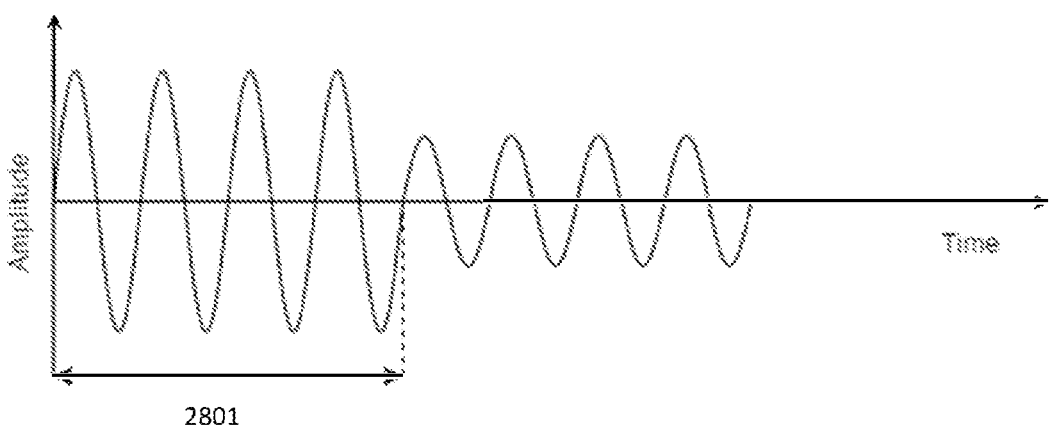
FIG. 28a shows an example of preheating with higher power level followed by continuous mode heating with lower power level.
Figure 28B:
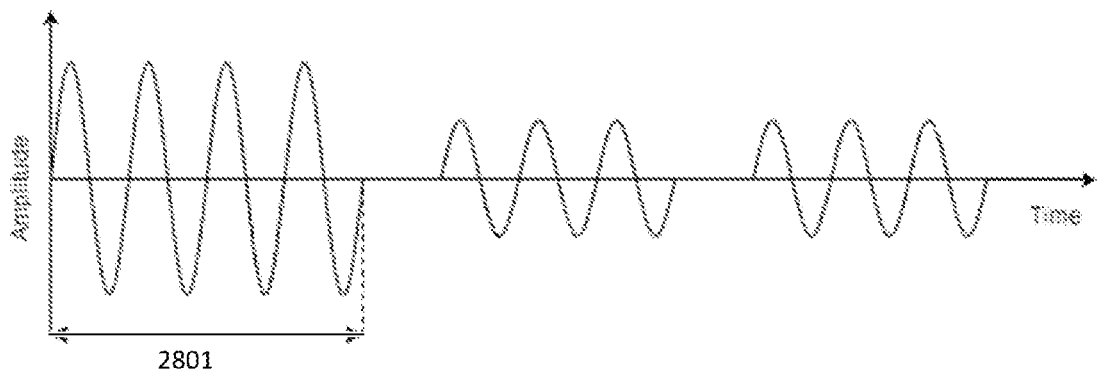
FIG. 28b shows an example of preheating with higher power level followed by pulsed mode heating with lower power level.

The power is adjusted according to the therapy process. Examples are shown in FIGS. 23c, 23d, 25, 26, 28a and 28b. For instance, in the case shown in FIGS. 28a and 28b, the power is temporarily increased at the beginning of the therapy, leading to a rapid increase in temperature. The therapeutic temperature can be reached in shorter time and the total duration of the therapy is thus optimized. Preheating interval 2801 is either predefined or dynamically adjusted according to the feedback measurements. Most often, the preheating stops when the therapeutic temperature is reached. Also, it can be stopped when a specific temperature gradient in the targeted tissue is achieved, or after a predetermined time. After the preheating, the treatment can continue at reduced power, as shown in the examples of FIG. 28a for continuous treatment, and in 28b for pulsed treatment. This reduced power is generally sufficient for maintaining the therapeutic temperature. This procedure helps to avoid overheating of the tissues. Also, it optimizes the temperature profile and makes the results of the therapy repeatable, given that the main part of therapy starts at well-defined conditions, most often with the targeted tissue preheated to a defined temperature. It is advantageous that the reduced power which is delivered after the preheating interval 2801, can be either predefined or dynamically adjusted according to the feedback measurements. In other cases, the therapy can be continued by switching to any of the above described modes or their combinations, according to the targeted therapeutic effect. Most often, the maintenance of the therapeutic temperature is sought, and the power applied within the modes following the preheating interval 2801 can be lowered.

When only a smaller temperature gradient in the targeted tissue is required, it is possible to start the diathermy by delivering a smaller power and preheat the targeted tissue to some temperature lower than the therapeutic one, as shown in FIG. 25. Then, the therapy can be continued by any of the above described modes.

All the above mentioned methods, i. e. the emission modes including pulsed mode, continuous mode, amplitude modulation mode, frequency modulation mode, frequency adjustment, power adjustment and different cooling modes, can be mutually combined.

For the purpose to utilize some of benefits of penetration, polarization, dispersion, targeting, filtering, absorption, changing of energy transfer properties and/or other manipulation with electromagnetic wave is advantageous to use microwave in the range of 300 MHz and 300 GHz which results from the used wave length. Wavelength has crucial influence for biological effect and modification of wave character Thanks to wavelength it is possible to influence polarization and/or other characteristics of the electromagnetic waves. Another benefit of microwave is that microwaves in comparison with short waves has shorter wavelength therefore more similar to size of some cells and/or molecular systems and/or structure and that is the reason why it is possible to directly and selectively influence this structure in desired manner. It is also known that microwave has dominant electrical component of electromagnetic radiation, which may be advantageously used for treating mostly subcutaneous fat and/or cellulite primarily by thermal heating According to still another embodiment, muscle stimulation or of other soft tissue structures, stimulation by electrical current and/or by magnetic field may be also used as type of soft tissue massage. Muscle stimulation may improve targeting of heating up of soft tissue, provide better homogeneity in delivered energy, prevent local hot spots, improve blood and lymph circulation and/or influence dielectric properties of specific soft tissue layers (e.g. may synergistically influence transfer of RF waves into the soft tissue). Repeated muscle contraction accelerates body metabolism, heats up adjoining soft tissues, stimulates secretion of several hormones, may change polarity of some soft tissue structures that influence transfer of RF energy into the soft tissue and/or may be beneficial for body shaping as reducing adipose cell volume, muscle building, muscle strengthening. Muscle contraction causes massage of adjoining soft tissue structure and cause massage of the deep soft tissue layers without affecting the surface of the patient.

Different nerves and soft tissue structures may be stimulated using interferential electrotherapy with a medium frequency in the range of 500 Hz to 12 kHz or in a more preferred embodiment in the range 500 to 8 kHz, in the most preferred embodiment in the range 500 to 6 kHz, creating pulse envelopes with frequencies for stimulation of the nerves and tissues e.g. sympathetic nerves (0.1-5 Hz), parasympathetic nerves (10-150 Hz), motor nerves (10-50 Hz), smooth muscle (0-10 Hz), sensor nerves (90-100 Hz), nociceptive fibers (90-150 Hz).

Muscle stimulation may be provided by e.g. intermittent direct currents, alternating currents (medium-frequency and TENS currents), faradic current as a method for multiple stimulation and/or others. Frequency of the currents and/or its envelope is typically in the range from 0.1 Hz to 200 Hz in preferred embodiment or from 0.1 Hz to 150 Hz in more preferred embodiment or from 0.1 to 140 Hz in the most preferred embodiment.

The method of nerve/muscle stimulation by magnetic field may use a peak to peak magnetic flux density on a coil surface at least 0.2 T, 0.4 T, 1.5 T, 2 T, at least 3 T, or up to 7 T. The repetition rate may be 1 Hz-700 Hz or more preferably 1 Hz-300 Hz or most preferably 1 Hz-200 Hz, with initial or successive treatments lasting several seconds or longer, for example, for at least 5, 10, 30, 60, 120 or 240 seconds, or longer. The pulse width is in the range of tens to hundreds of microseconds.

Stimulation of a patient's soft tissue by magnetic field and/or electric field may be used with or without contact of such treatment energy source with the patient's surface.

A treatment energy source may also provide another treatment by a generated magnetic field and/or electric current. Exemplary frequency ranges for individual types of treatment are:

2-10 Hz—endogenous opioid theory—chronic pain management;

60-100 Hz—gate control theory—acute pain management;

120-140 Hz—peripheral pattern theory—subacute pain management;

5 and 150 Hz—fracture healing;

45 Hz—joint mobilization;

2-70 Hz—myostimulation.

RF treatment energy source combined with at least partial muscle stimulation may have also other convenient parameters and effects as it is described in U.S. Provisional Application No. 62/340,398 incorporated herein by reference.

It is an object of the invention to provide an apparatus and method for improving skin viability, rejuvenation, tightening and body shaping, contouring and/or treatment of other skin and body conditions using application of RF energy and electrical stimulation to soft tissue.

The device may be composed of power supply, control unit, user interference, and one or more applicators, wherein the at least one applicator provides RF therapy and/or electrotherapy. The device may include a cooling mechanism. The patient's skin may be cooled to minimize discomfort and/or health risk, or to make therapy more effective and/or faster. Some components of the device may be cooled to prevent them from overheating.

RF (radio frequency) energy may selectively treat different tissues based on their impedance and localization. Applied RF field affects treated soft tissues mainly by a thermal effect. However, the RF field may also influence ions and partially charged molecules in the treated cells and molecular complexes.

Electrotherapy is founded on the effect where an electric current (a) passes through the body and/or (b) locally changes ion balance and/or (c) changes electric potentials in the soft tissue. The effect of electrotherapy may be muscle contraction and/or partial, local ionization of a soft tissue. Another effect may be influence formation and/or spreading of nerve stimulation. In some embodiments electrotherapy may not provide thermal therapy of soft tissue.

According to one embodiment RF energy and electrical stimulation may be used simultaneously or in sequence via one or more energy sources.

In order to improve the treatment effect, electrotherapy may be used in several ways: analgesia, tissue regeneration, relaxation, partly tissue ionization, muscle building, muscle strengthening and/or others as described below. Combinations of electrotherapy and RF therapy have desirable effects in soft tissue treatment.

Using electro-stimulation of skeletal muscle fibers and/or other soft tissue by using electrotherapy and application of an RF field has several synergistic benefits. Repeated contraction of muscle fibers improves lymphatic and blood circulation in local and peripheral tissue. Increased blood circulation has a positive effect on homogeneity and dissipation of delivered energy into the targeted tissue. Combined therapy (in simultaneous and/or sequential use) minimizes risk of creating hot spots and consecutive unwanted soft tissue injury during the treatment. Without being bound to the theory, it is believed that the increased blood flow in the target soft tissue and/or peripheral soft tissue has substantial influence on removal of cellulite and/or fat tissue.

Another method to reduce adipose cells is skin massaging by electro-stimulation. This method is based on improving of blood circulation and increasing fat metabolism. Improved effects of blood, lymphatic circulation and fat metabolism may be provided by skeletal muscle stimulation.

Electrotherapy may be provided simultaneously, with some overlay or sequentially, before and/or after application of RF therapy. Electrotherapy and RF therapy may be provided to the same and/or to the different target areas. Electrotherapy and/or RF therapy may be provided by different types of pulses and/or by continual stimulation. Energy of RF therapy and/or electrotherapy may be modulated in different ways (e.g. shape of the signal and the envelope-curve outlining the signal, polarization of the signal, intensity, frequency, time between one or more pulses, and/or other forms of modulation.

The advantages of electrotherapy is targeting energy into muscle fibers of a muscle group. Contracting muscle fibers may be used for internal massage of target and/or adjacent tissue. This massage phenomenon is beneficial to lymphatic and blood circulation that cause acceleration of metabolism. Faster metabolism provides a better treatment result and more effective treatment, which means a shorter therapy time, and the effect may be long lasting in comparison with prior art methods. Stimulation of lymphatic and/or blood circulation reduces health risk while removing fat and/or cellulite and also improves the therapy results.

A beneficial effect of the present methods is to treat cells in order to induce apoptotic death. Due to combined effect of the RF therapy and electrotherapy and increased blood and lymph circulation, the cells at the targeted area are treated more homogenously and cells are removed faster.

The present device has several possible embodiments based on invasive and/or non-invasive methods, wherein the applicator may also be adapted to operate in contact or non-contact mode with the skin of the patient.

An applicator includes one or more electrodes. The electrodes may be modularly connected to the applicator in order to vary the treatment surface, distance between electrodes and provide easier, effective, faster and/or safer treatment. Electrodes may be controlled individually and/or in a group. Controlling the electrode includes changing parameters of energy: intensity, flux density, time between pulses, shape of signal, type of produced therapy and/or switching on/off an individual electrode or electrodes.

The applicator and/or electrodes may be created from rigid or flexible material adaptable to curved body surfaces. Transfer of electrical and/or RF energy into the soft tissue and different parts of the patient may be based on capacitive, inductive and/or resistive energy transfer.

RF therapy provides electromagnetic field which heats soft tissue. Heat is produced as a resistive loss of electromagnetic energy. Warming of the tissue is based on impedance characteristics of the tissue. Heating and/or cooling of the soft tissue is important because the soft tissue dielectric and other parameters (e.g. permittivity, permeability, impedance, conductivity and/or other related dielectric parameters) change with changes in temperature and frequency of applied electromagnetic waves. While the conductivity of soft tissue increases with temperature, cooling of the soft tissue may result in less electrical conductivity. These properties may help with targeting of the delivered energy into the soft tissue. Heating and/or cooling during, before and/or after treatment may be provided by cooling/heating pads, plates, spacing objects and/or gels. Temperature targeting may differ with various therapies e.g.: neocolagenesis, neoelastogenesis, fat removal, or protecting of an area.

RF therapy can be applied to the soft tissue in various ways. The treatment system can use bipolar electrodes, where electrodes alternate between active and return function and where the thermal gradient beneath the electrodes is almost the same during treatment.

The system may alternatively use monopolar electrodes, where a so-called return electrode has a larger area than the so-called active electrode. The thermal gradient beneath the active electrode is therefore higher than beneath the return electrode A unipolar electrode may also optionally be used. During unipolar energy delivery there is one electrode, no grounding pad, and a large field of RF emitted in an omnidirectional field around a single electrode.

If more than one applicator is used, applicators may be positioned on opposite sides of the patient. A spacer may be positioned between one or more applicator and the skin of the patient. The electromagnetic waves may be transmitted in the range of range 6 765 to 6 795 kHz or 13 553 to 13 567 kHz or 26 957 kHz to 27 283 kHz or 40.66 to 40.7 MHz or 433.05 to 434.79 MHz or 902 to 928 MHz or 2 400 to 2 500 MHz or 5 725 to 5 875 MHz or 24 to 24.25 GHz or 61 to 61.5 GHz or 122 to 123 GHz or 244 GHz to 246 GHz from the applicator into the subcutaneous tissue. The temperature of the tissue surface may be increased to about 32-70° C. more preferably from 35-60° C. most preferably from 37-50° C.

Electromagnetic fields used for heating soft tissue may be a radiofrequency field or microwave field, typically in the range of 0.1 MHz to 25 GHz. Waves of the RF therapy may be delivered preferably in the range from 100 kHz to 3 500 kHz or 6 765 to 6 795 kHz or 13 553 to 13 567 kHz or 26 957 kHz to T1 283 kHz or 40.66 to 40.7 MHz or 433.05 to 434.79 MHz or 902 to 928 MHz or 2 400 to 2 500 MHz or 5 725 to 5 875 MHz or 24 to 24.25 GHz or 61 to 61.5 GHz or 122 to 123 GHz or 244 GHz to 246 GHz or optionally at other frequencies as well.

The main effects of electrotherapy are: analgesic, myorelaxation, iontophoresis, and at least partial muscle contraction and anti-edematous effect.

Each of these effects may be achieved by one or more types of electrotherapy: galvanic current, pulse direct current and alternating current.

Galvanic current (or "continuous") is a current that may have constant intensity and/or a non-zero absolute value of intensity at all times. It may be used mostly for iontophoresis, or for trophic stimulation (hyperemic) effect. Galvanic intermittent current may also be used. The galvanic component may be about 95% but due to interruption of the originally continuous intensity the frequency may reach 5-12 kHz, 5-9 kHz, or 5-8 kHz.

Pulse direct current (DC) is of variable intensity but only one polarity. The basic pulse shape may vary. It includes e.g. diadynamics, rectangular, triangular and exponential pulse of one polarity. Depending on the frequency and intensity it may have stimulatory, tropic, analgesic, myorelaxation, iontophoresis, at least partial muscle contraction and anti-edematous effects.

In Alternating Current (AC), the basic pulse shape may be rectangular, triangular, harmonic sinusoidal, exponential and/or other shapes and/or combinations of those mentioned above. It can be alternating, symmetric and/or asymmetric. Use of alternating currents in contact electrotherapy implies much lower stress on the tissue under the electrode. For these types of currents the capacitive component of skin resistance is involved, so that these currents are very well tolerated by patients.

AC therapies may be differentiated into five subtypes: TENS, Classic (four-pole) Interference, Two-pole Interference, Isoplanar Interference and Dipole Vector Field. The modularity of period and shape of the energy may vary.

Using interferential electrotherapy different nerves and soft tissue structures can be stimulated by a medium frequency of 500 Hz to 12 kHz, 500 to 8 kHz, or 500 to 6 kHz, creating pulse envelopes with frequencies for stimulation of nerves and tissues e.g. sympathetic nerves (0.1-5 Hz), parasympathetic nerves (10-150 Hz), motor nerves (10-50 Hz), smooth muscle (0-10 Hz), sensor nerves (90-100 Hz) nociceptive fibres (90-150 Hz).

Electrotherapy may provide stimulus with currents of frequency in the range from 0 Hz to 12 kHz, 0 Hz to 8 kHz or 0 Hz to 6 kHz.

Time between two pulses and/or time between two band of pulses (burst) may be variable depending on a function and adjustable with the type of therapy and type of the patient.

Analgesic effects may be achieved. The analgesia is beneficial during the treatment of high dose RF therapy and in order to make therapy more comfortable. Some highly sensitive individuals may feel discomfort and/or pain during the treatment therapy, even if the treatment runs within the range of safe threshold limits. Another beneficial effect is that if patient feels pain, muscle tone usually increases in the affected area. Long lasting muscle contraction may cause pain in the muscle for several days and/or damage muscle fibers. Long lasting muscle contraction is therefore not only uncomfortable, but it also may affect the blood and lymph circulation. Whereas the treatment may be improved by sufficient fluid circulation during and/or after the treatment.

In electrotherapy, it is important to understand the modulating factors influencing the perception and transfer of the painful stimulus. An analgesic effect may occur by stimulation of type A nerve fibres by frequency 50-150 Hz and/or type C-thin fibers by frequency 2-8 Hz.

For most analgesic effects it is possible to choose several types of currents e.g. diadynamic current, currents changing in long lasting period, bipolar amplitude modulated medium frequency currents, TENS and/or other interferential currents (in range of 0.1-1 kHz). Frequencies of the currents are described above.

A myorelaxation effect may be achieved. Myorelaxation effects cause at least a partial decrease in muscle fiber tone. Myorelaxative effects may be beneficial for improving homogeneity of delivered RF therapy and/or faster regeneration of the soft tissue and/or a more comfortable therapy. Long lasting permanent muscle contraction may slow body fluid circulation e.g. lymph and blood circulation, that has a therapy effect. Long lasting muscle contraction is also very exhausting. For better results, a comfortable therapy is needed because the psychological state of the patient has influence on human metabolism.

In order to provide myorelaxation amplitude modulated medium frequency currents, a frequency of the pulse envelope in range 0-300 Hz, 0-200 Hz or 0-150 Hz may be used. It is also possible to use TENS and/or others.

According to another embodiment muscle fibers stimulation may be achieved. Muscle stimulation increases muscle tone, muscle strengthening, restoration of feeling the muscle, relaxation of the musculature and/or stretching musculature.

Muscle stimulation increases a blood flow and lymph circulation. It may improve removing of treated cells and/or prevent creation of hot spots. Moreover internal massage stimulation of adjoining tissues improves homogeneity of tissue and dispersing of the delivered energy. During fat removal, the RF therapy may change the structure of the fat tissue. The muscle fiber stimulation may provide internal massage, which may be for obese patient more effective than classical massage.

Muscle stimulation may be provided by e.g. intermittent direct currents, alternating currents (medium-frequency and TENS currents), faradic current as a method for multiple stimulation and/or others. Frequency of the currents and/or its envelope is typically in the range from 0.1 Hz to 200 Hz, 0.1 Hz to 150 Hz, or from 0.1 to 140 Hz.

According to still another embodiment the electrostimulation may be provided in a combined manner where various treatments with various effects may be achieved. As an illustrative example, the electromagnetic stimulation may be dosed in trains where the first train of stimulation may achieve a different effect than second or other successive train of stimulation. Therefore, the treatment may provide muscle fibers stimulation followed by relaxation, during continual or pulsed radiofrequency thermal heating.

Current density of electrotherapy for nongalvanic current may be preferably lower than 10 $mA \cdot m^{-2}$, lower than 5 $mA \cdot m^{-2}$, lower than 4 $mA \cdot m^{-2}$, or lower than 1 $mA \cdot m^{-2}$. Galvanic current may be preferably lower than 1 $mA \cdot m^{-2}$, lower than 0.5 $mA \cdot m^{-2}$, or lower than 0.1 $mA \cdot m^{-2}$.

Energy flux density of RF therapy is preferably in the range of 0.01 $mW \cdot mm_{-2}$ to 10 000 $mW \cdot mm^{-2}$, 0.1 $mW \cdot mm_{-2}$ to 5 000 $mW \cdot mm^{-2}$, or 0.5 $mW \cdot mm_{-2}$ to 1 000 $mW \cdot mm^{-2}$.

The source of RF waves and/or electrotherapy may be at least one electrode. When the only one electrode is applied, the electrode may serve as both the RF and the electrotherapeutic source. The therapies may be applied together, successively or in overlap. The electrode may consist of electrode itself and coating, wherein the coating may not cover the whole surface of electrode.

Figure 29:
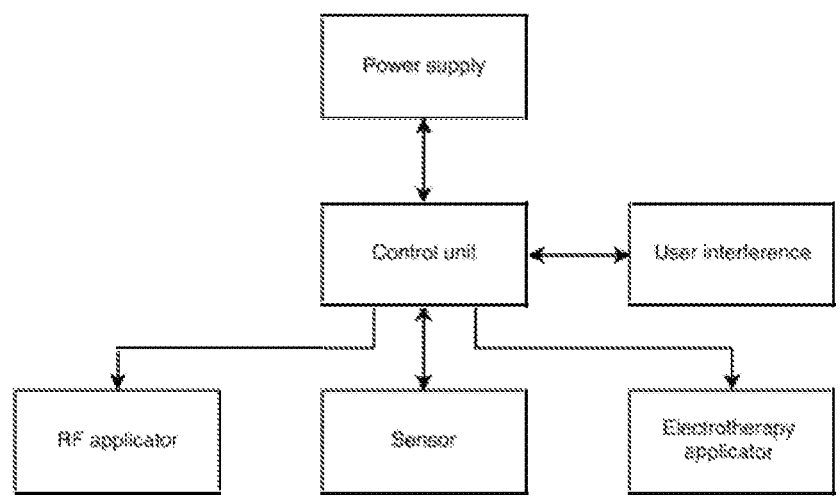
FIG. 29 is a schematic diagram of a treatment system.

In FIG. 29 the system has a power supply, control unit, user interference, one or more sensors and an applicator providing RF and an applicator providing electrotherapy. However, there may be only one applicator providing both RF therapy and electrotherapy.

The power supply may be managed by the control unit. Regulation of delivered energy may be controlled by the control unit. The control unit may also evaluate feedback information from one or more sensors, and/or treatment parameters from the user interface and/or by a predetermined protocol. The control unit may contain one or more cooperating units. Control and cooperation units are elements of the device influence treatment parameters of the therapy (e.g. therapy time, amount of delivered energy, burst timing, frequency of provided energy, intensity of energy, controlling switching on/off different group of electrode/s, shape of the pulses and others). The one or more control units may be located in the applicator and/or one or more control units may by located out of the applicator (e.g. in the case of the device).

The user interface may allow operator to change and/or set up the treatment parameters. Treatment parameters may be set up in the range of safe thresholds (e.g. individually for each therapy). Threshold treatment parameters may be operatively changed depending on therapy and/or detected parameters from the feedback sensors. Safe dosage of the delivered energy and/or dependence of each parameter may be pre-set. Course of treatments may be provided by computer and/or operator. Treatment may be guided manually, automatically and/or semi-automatically where some of the treatment parameters are set up manually A computer may change inappropriately set up parameters and/or alert the operator.

If treatment parameters are evaluated as safe, therapy may start. It may be possible to adjust parameters of the therapy or add therapy types e.g. galvanic current, pulse direct current and alternating current. Treatment may be time limited and stopped if values of one or more detected parameters reach their limits e.g. time, time and temperature. Safe thresholds may be dependent on treated body part or target area. The soft tissue to be treated may be classified by e.g. ultrasound, or from the information of backscattered radiofrequency wave.

The method may be carried out automatically or semi-automatically substantially without human control or can be carried only with human control, without or with any predetermined parameters (including sequences, shape of delivered pulses etc.).

The device may have one or more sensors providing feedback information in order to improve efficiency of the treatment and reduce health risk. Based on feedback treatment information, therapy parameters may be manually or automatically or semi-automatically optimized or therapy may be interrupted. Sensors also may control some properties of the device. The device may contain different types of sensors for monitoring device parameters and/or monitoring of body biological, physical, chemical and/or other parameters (e.g. a reactive sensor; an electrochemical sensor; a biosensor; a biochemical sensor; a temperature sensor; a sensor for measuring distance of the applicator from the patient skin, from some area of the patient soft tissue and/or from the other applicator; a sorption sensor; a pH sensor; a voltage sensor; a detector of moving velocity and/or change of position; photo sensor; sensor measuring viscosity; a camera; a sensor measuring fluorescence of the patient surface; a sound detector; a current sensor; sensor for measuring of specific heat capacity of human/animal tissue; sensor for measuring impedance; permittivity; conductivity; susceptibility and/or any suitable sensor or sensors measuring biological parameters and/or combination thereof e.g.: sensor for measuring dermal tensile forces; sensor for measuring the activity of the muscle; a muscle contraction forces; skin elasticity). The device may also include at least one contact sensor for monitoring of applicator and/or electrode or more electrodes contact with body surface.

Each sensor may provide feedback information to control energy delivery and/or other treatment parameters to improve efficiency of a treatment and/or reduce health risk and/or discomfort during the treatment. The treatment therapy parameters may be manually or automatically or semi-automatically optimized based on feedback information. If the treatment parameters are evaluated as not-safe, the treatment is stopped or the treatment parameters may be changed.

Treatment therapy may be guided with partially or fully predetermined treatment protocol or without predetermined treatment protocol. With the treatment carried automatically (allowing treatment without operator), semi-automatically and/or by operator. The operator may set up and/or adjust any parameter of treatment therapy.

In one embodiment applicator may be stationary adjacent to the patient surface. In another embodiment moving the applicator or multiple applicators may be advantageous.

Moving with the applicator may be provided automatically (provided without operator), semi-automatically (e.g. mechanical arm) and/or manually by operator.

Movement of the applicator may be straightforward, curvilinear, rotational, changing distance from the patient surface and/or may create some pattern. A plurality of applicators may move in a synchronized, randomized and/or independent manner. The applicator may be automatically and/or manually moved and rotate along every Cartesian coordinate.

The one or more applicators may be placed or moved in a chosen geometry pattern comprising of e.g. linear, wavy circular, elliptical, zigzag, polygonal, oval, irregular, curvilinear or their combination. This moving may be replicated by placing one or more stationary applicators in position and switching over relevant electrodes, without moving the applicators.

The same possible movements of one or more applicators may be considered for moving the electrodes.

According another embodiment the device may provide treatment by plasma and/or by combination of plasma with another treatment energy source e.g. RF treatment energy source. Plasma may be also supplemented with substances enhancing generation of plasma and/or treatment results as described in U.S. Provisional Application No. 62/409,665 incorporated herein by reference.

According to another embodiment treatment may be further influenced and improved by an active agent substance (e.g.: gas, gel, liquid, suspension) that may make treatment more comfortable (e.g. less painful), faster, treatment may have better results and/or may make treatment more targeted. Active agent may be supplied before during and/or after treatment automatically by the device itself and/or by a person supervising the treatment.

In addition, the supplied mixture (e.g. green tea extract) may include other substances. Application of the substance and/or mixture of the substances may provide patient with a more comfort and/or improve the treatment effect.

In one embodiment, the substance may modulate normal metabolism and/or basal metabolism rate of the patient's body. It may provide acceleration to the metabolism related to the apoptotic cells. Such substances may include alkaloids (e.g. xanthines), antithyroid agents, metformin, octreotide and a like.

In another embodiment, the substance may modulate efferocytosis, which is the process by which dying cells are removed by phagocytic cells. This may provide acceleration and improvement in the dead cells removal. Such substance may include prostaglandins and their analogues, modified lipids (e.g. lysophosphatidylserine, lipoxins, resolvins, protectins and/or maresins), lipoprotein lipase inhibitors, nitric oxide secretion stimulators, alkaloids (e.g. xanthines), aspirin, antioxidants (e.g. ascorbic acid), derivatives of carbohydrates and a like.

In another embodiment, the substance may modulate lipolysis rate. In case of application of electromagnetic energy to the adipocytes it may provide another way of removal of the adipose cells, which may be independent from the treatment method. Such substances may include terpens (e.g. forskolin), catecholamins, hormons (e.g. leptin, growth hormone and/or testosterone), alkaloids (e.g. synephrin), phosphodiesterase inhibitors (e.g. xanthins), polyphenols, peptides (e.g. natriuretic peptides), aminoacids and a like.

In another embodiment, the substance may modulate hydration of the patient. Such substances and/or mixtures may include xanthines, lactated Ringer's solution, physiological saline solution and a like.

In another embodiment, the substance may modulate circulatory system of the patient. This may provide the higher rate of blood circulation, which may result in faster cooling rate of the skin. Such substances may include catecholamines, alkaloids (e.g. xanthins), flavanols and a like.

In another embodiment, the substance may induce the reversible decrease or absence of sensation in the specific part of the patient's body. This may provide a certain level of comfort to heat-sensitive patient. Such substances may include lidocaine, benzocaine, menthol and a like.

In another embodiment, the substance may shield the electromagnetic radiation from the patient's body. This effect may be used for protection of sensitive parts of the human body. Such substances may include mixture containing metal nanoparticles, mixture containing polymer particles and a like.

In another embodiment, the substance may modulate the effect the electromagnetic radiation applied on the patient's body. This may accelerate removal of the desired tissue, for example by heating of the tissue and/or increasing the effect of the applied radiations. Such substances may include carotens, chlorophylls, flavanols and a like.

Substances may be used singularly or in various combinations with at least one other suitable substance. For example, lidocain providing local anesthesia may be combined with prilocaine to provide improved effect. The substance and/or mixture of the substances may be administered at different times during the tissue treatment. It may be administered before the treatment, during the treatment and after the treatment.

In another embodiment, the substance may be administered over seconds, hours or even days to accumulate in the desired tissue. The subsequent application of the electromagnetic radiation may modulate the action of the accumulated substance and/or be modulated by the action of the substance. According the example of this embodiment, a chromophore may be accumulated in the treated tissue, such as adipocytes, before the treatment. The chromophore may then absorb electromagnetic radiation and heat the tissue nearby.

Such active agents may influence the treatment therapy as described in U.S. Provisional Application No. 62/331,060 incorporated herein by reference.

Connection transferring high frequency (above 100 kHz) signal between individual parts of the device (e.g. connecting of the applicator or other devices) may be provided by special magnetic connection transferring high frequency signal or high frequency signal and data.

Such magnetic connection may be an easier, faster way to connect high frequency sources and may have longer durability than connector based on principal sinking or latching one part of connector to another part of connector.

Figure 9:
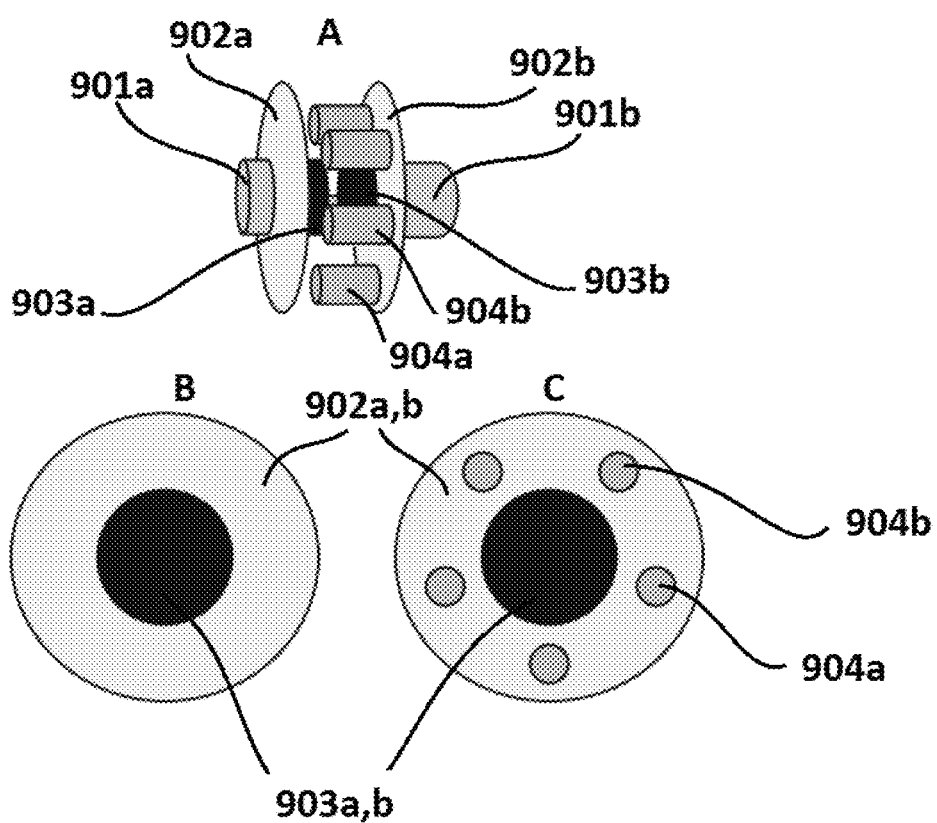
FIG. 9 illustrates high-frequency connector

One of possible embodiment of such a connection is illustrated in the FIG. 9A, FIG. 9B and FIG. 9C. FIG. 9A illustrates both parts of the connector connecting together a lower part of the connector and an upper part of the connector as depicted in FIG. 9B and FIG. 9C, respectively.

Connector includes supply cables 901*a* and 901*b* attached to conductive plates 902*a* and 902*b*. The upper and/or the lower part of the connector are attached to permanent or temporary magnet(s) 903*a*, 903*b* in order to provide connections between both parts. High frequency signals may be transferred between the lower and the upper connector part by a conductive connecting member(s) 904*a* and 904*b* rising from the lower and/or the upper part of the connector.

Conductive plates 902*a* and 902*b* may be replaced by more conductive elements located in the lower and the upper part of the connector.

The number of conductive connecting members 904, their size and shape may be variable. According one embodiment connecting members 904 may be formed as pins or cylinders (see FIG. 9). Diameter of such cylinder may be in range 0.1 mm to 5 cm or 0.1 mm to 1 cm or in range 0.1 mm to 5 mm. According another embodiment, cylinders may be replaced by conductive ring, Cylinders with at least partial spherical objects on one end and/or other shapes of conductive connecting member 904. Conductive connecting member(s) 904 is connected with supply cable(s) 901 by conductive plate(s) 901, directly or through other conductive or semi-conductive members. When connector is connected at least one conductive connecting member 904 is in contact with both parts of the connector. Conductive connecting member 904 may be from conductive or semi-conductive material(s).

High frequency signal is mostly transferred on the surface of the conductive connecting member 904. In order to minimize overheating of magnet(s) 903 providing attaching of both connector parts, and also in order to minimize inducting of electric or electromagnetic field acting against transferred high frequency signal in conductive connecting member(s) 904, conductive connecting members 904 are placed around the central magnet(s) 903 as it is illustrated in the FIG. 9.

Described type of high frequency connector may be used also as coaxial cable for information transfer.

According to another embodiment the method and the device described above may be used in combination with a method and a device of light therapy, described below. Such light method and the device may be implement in the applicator using vacuum and RF and/or may be used as separated applicator providing at least light therapy treatment as it is described below.

Figure 10:
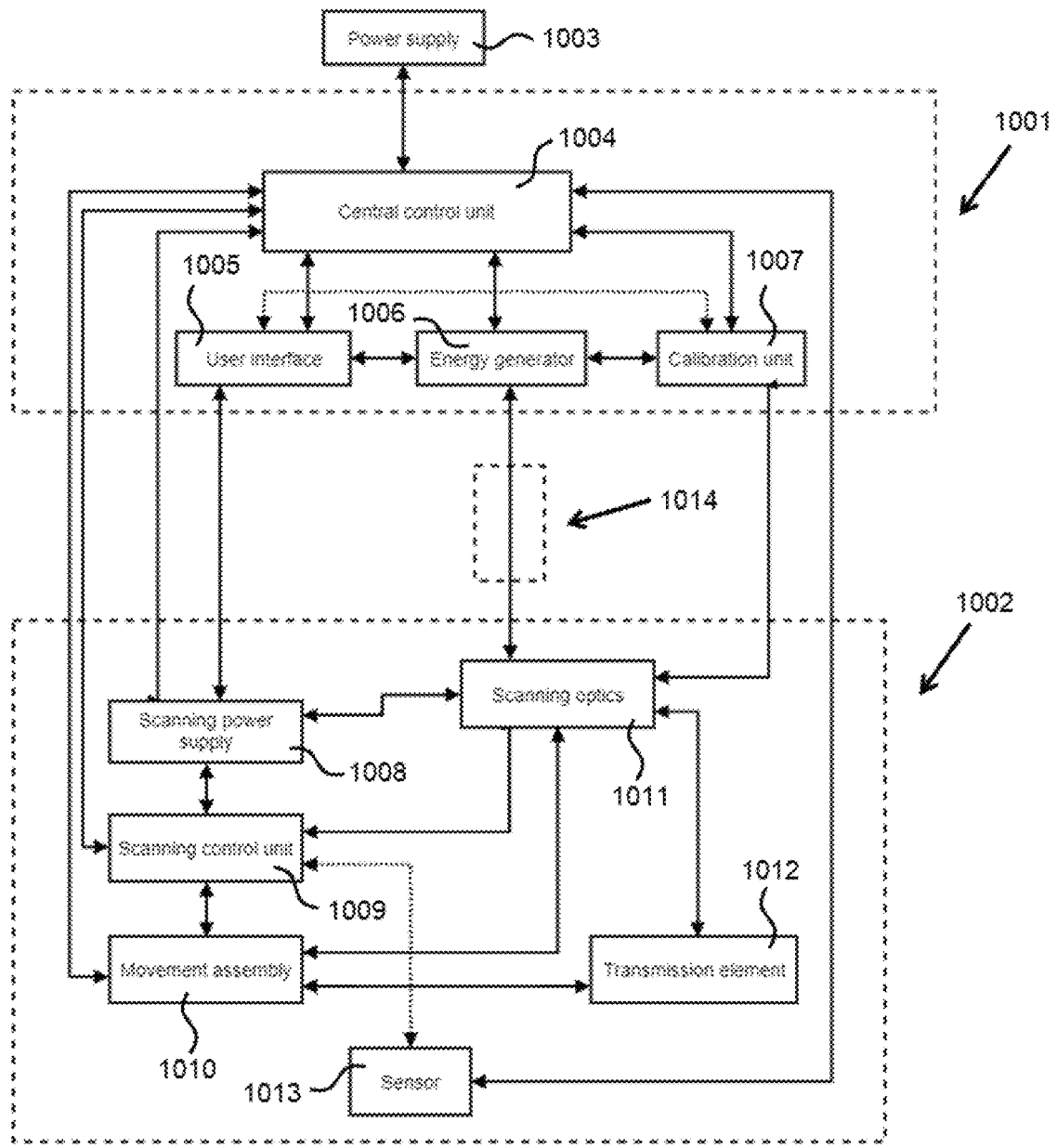
FIG. 10 is a diagram of an exemplary device

Referring now to FIG. 10, in one embodiment the device includes base 1001, handheld applicator 1014, and/or scanning unit 1002. Handheld applicator 1014 may be used for delivery of light energy from the base 1001 to the scanning device 1002. Base 1001 may include central control unit 1004, user interface 1005, energy generator 1006 and/or calibration unit 1007.

The central control unit 1004 may change the treatment parameters and/or control other parts of the device coupled to it. The method of operation may include the central control unit 1004 communicating with user interface 1005, energy generator 1006, power supply 1003 and/or calibration unit 1007. The central control unit 1004 may also communicate with a scanning power supply 1008, scanning optics 1011, scanning control unit 1009, movement assembly 1010 and/or transmission element 1012 located in the scanning unit 1002.

The device may include one or more energy generators. Energy generator 1006 may comprise, for example, a light emitting diode, a laser emitting diode, a flashlamp, a tungsten lamp, an incandescent lamp, a mercury arc, or any other light or energy source known in the art. Energy generator 1006 may generate coherent, incoherent, depolarized and/or polarized light. Coherent monochromatic light may include any type of laser, for example a chemical laser, a dye laser, a free-electron laser, a gas dynamic laser, a gas laser (for example an argon laser or carbon dioxide laser), an ion laser, a metal-vapor laser (for example a gold vapor laser and/or a copper vapor laser), a quantum well laser, a diode laser (for example comprising GaAs, AlGaSbAs, InGaAsP/InPm InGaAs), and/or a solid state laser (for example a ruby laser, a Nd:YAG laser, a NdCr:YAG laser, a Er:YAG laser, an Er:glass laser, a CTH:YAG laser, a Nd:YLF laser, a Nd:YVO4 laser, a Nd:YCOB laser, a Nd:Glass laser, a Ti:sapphire laser, a Tm:YAG laser, a Ho:YAG laser or an Er,Cr:YSGG laser). The energy generator may be cooled by air and/or water. Methods of operation may include energy generator 1006 communicating with user interface 1005, calibration unit 1007 and/or central control unit 1004. Energy generator 1006 may also communicate with scanning optics 1011, typically by providing the generated energy (for example light).

User interface 1005 may include an LCD panel or other suitable electronic display. User interface 1005 may be located on the base 1001, handheld applicator 1014, and/or scanning unit 1002. User interface 1005 may communicate with energy generator 1006, central control unit 1004 and/or calibration unit 1007. User interface 1005 may also communicate with scanning optics 1011 and scanning power supply 1008 located in the scanning unit 1002.

Calibration unit 1007 may be controlled by central control unit 1004. Calibration unit 1007 may check the stability of the output and/or the wavelength or wavelengths of the energy generator 1006. In case of instability, calibration unit 1007 may provide one or more human perceptible signals to the operator. The calibration unit 1007 may also provide information to the central control unit 1006 which may adjust or correct one or more parameters of energy generator 1006. Calibration unit 1007 may check input or output parameters of the energy the scanning optics 1011, located in the scanning unit 1002. Methods of operation may include the calibration unit 1007 communicating with user interface 1005 and/or central control unit 1004.

Calibration unit 1007, energy generator 1006 and/or user interface 1005 may be positioned in or on base 1001, handheld applicator 1014 or scanning unit 1002.

Embodiments of devices of the present invention may include one or more scanning units 1002 which may include scanning power supply 1008, scanning control unit 1009, movement assembly 1010, scanning optics 1011, sensor 1013 and/or transmission element 1012. In some embodiments, scanning unit 1002 may provide movement of the energy spot by changing one or more characteristics of the energy beam, including but not limited to the direction or intensity of the energy beam. A method of treatment may include control of the scanning unit 1002 through central control unit 1004 by the user interface 1005. The scanning unit 1002 may in some embodiments be positioned on a manually or automatically adjustable arm. The scanning unit may be tilted to any angle with respect to the tissue. During some embodiments of treatments using the system of the present invention, the scanning unit may remain in a set position and the energy spot may be moved by the optics inside the scanning unit. In some embodiments, the scanning unit may move continuously or discontinuously over the body and provide treatment by one or more treatment patterns.

The scanning power supply 1008 may provide electrical power to components of the present invention, including but not limited to scanning optics 1011, scanning control unit 1009, movement assembly 1010 and/or transmission element 1012. The scanning power supply may comprise a battery and/or a power grid. The scanning power supply 1008 may be coupled to power supply 1003. Alternatively, electrical power may be supplied from the power supply 1003 directly to some or all mentioned parts by the scanning power supply 1008.

The scanning optics 1011 may include one or more collimators, light deflecting elements (e.g. deflecting mirrors), focusing/defocusing elements (e.g. lenses) and/or filters to eliminate certain wavelengths of light. The scanning optics 1011 may be controlled according to an operator's needs through user interface 1005. The scanning optics 1011 may be controlled by central control unit 1004 and/or scanning control unit 1009. Both central control unit 1004 and scanning control unit 1009 may control one or parameters of the scanning optics, particularly of one or more deflecting elements. Parameters controlled may comprise the speed of movement of one deflecting element, which may be in the range of 0.01 mm/s to 500 mm/s, more preferably in the range of 0.05 mm/s to 200 mm/s, most preferably in the range of 0.1 mm/s to 150 mm/s.

Scanning control unit 1009 may control one or more treatment parameters. The scanning control unit 1009 may communicate with central control unit 1004, scanning power supply 1008, movement assembly 1010 and/or scanning optics 1011. The scanning control unit 1009 may be controlled through central control unit 1004 according to the operator's needs selected on the user interface 1005, or the scanning unit 1002 may include another user interface. In one embodiment, one or more functions of the scanning control unit 1009 may be assumed and/or overridden by central control unit 1004.

Movement assembly 1010 may cause movement of one or more energy spots on treated tissue. The movement assembly 1010 may communicate with scanning optics 1011 and cause movement of one or more light deflecting elements, which may be parts of the scanning optics 1011. The movement assembly 1010 may be controlled by central control unit 1004 and/or scanning control unit 1009. The movement assembly 1010 may also communicate with transmission element 1012. The movement assembly 1010 may comprise one or more motors and/or actuators. The movement assembly 1010 may provide angular and/or linear movement to the light deflecting elements of the scanning optics 1011. In some embodiments, the movement assembly 1010 may provide movement to the transmission element 1012.

Some energy may leave the scanning unit 1002 through the transmission element 1012. Transmission element 1012 may comprise one or more elements made from translucent materials, e.g. from glass, diamond, sapphire or transparent plastic. Transmission element 1012 may be connected to the movement assembly 1010, which may control focusing, defocusing, vertical or curvilinear movement or tilting of the transmission element 1012. Vertical movement of the transmission element 1012 may be used to change the energy spot size. Horizontal movement of the transmission element 1012 provided by movement assembly 1010 may be used to change one or more parameters of a light or energy beam delivered to the tissue. When the transmission element includes more elements made from translucent material, horizontal movement may be represented by movement of a separate element into the pathway to change one or more characteristics of the energy provided to tissue (e.g. focus, power output). Some disclosed configurations may be used for application of more than one energy beam to the tissue. Some configurations may include a scanning unit comprising more than one transmission elements 1012. In some embodiments, the one or more transmission elements 1012 are optionally covered by coverings, for example lens caps, controlled by movement assembly 1010.

The scanning unit 1002 and/or handheld applicator 1014 may include one or more sensors 1013, e.g. an ultrasound sensor, a gyroscope, a Hall sensor, a thermographic camera and/or an IR temperature sensor.

Additionally, the energy generator 1006 may be part of an energy generating module which can be removed from the base 1001, the handheld applicator 1014 or the scanning unit 1002. User may vary the wavelength of the energy by adding, replacing or removing at least one or more energy generating modules. The energy generating module may include at least one energy generator 1006 together or without calibration unit 1007 and identifier, which may communicate with central control unit 1009 and user interface 1005. Identifier may be an RFID tag, sequence of specific electrical pulses, measuring of magnetic field in/near the connection that may be specific for individual type of the energy generating module. After connection of the energy generating unit to the device, central control unit 1009 may identify the energy generating unit by the identifier.

The adjustable arm may be adjusted manually by user or automatically. In one embodiment, handheld applicator 1014 may be coupled to the scanning unit 1002 through adjustable arm including wave guide.

Figure 11A:
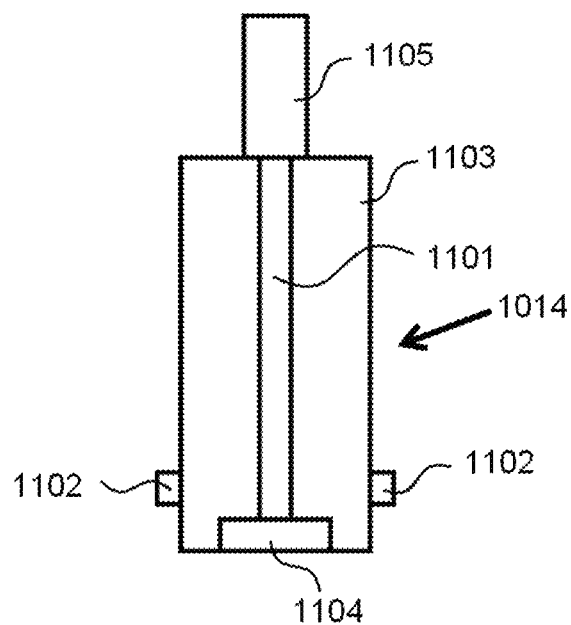
FIG. 11A is a schematic of an exemplary handheld applicator

FIG. 11A shows an exemplary handheld applicator 1014, comprising body 1103, light waveguide 1101, sensor 1102 and/or translucent element 1104. Flexible light waveguide 1105 may connect the handheld applicator 1014 with the base 1001. Light waveguide 1101 may be encased in the body 1103 and may provide an energy path where the energy path leaves the handheld applicator 1014 through the translucent element 1104. In some embodiments, translucent element 1104 is similar to transmission element 1012 of the scanning unit 1002.

Figure 11B:
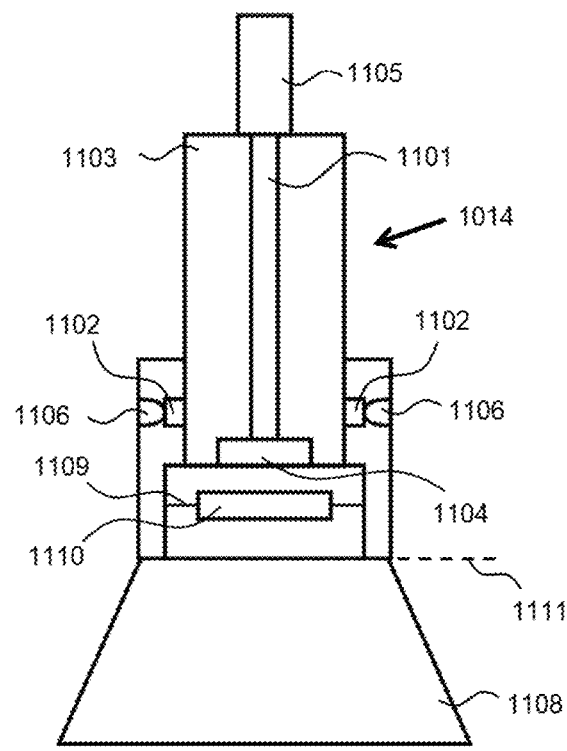
FIG. 11B is another example of a handheld applicator

FIG. 11B shows handheld applicator 1014 coupled to a zooming assembly including lens 1110, focusing mechanism 1109, spacer 1108 and emitters 1106. The handheld applicator 1014 may control the energy spot size by manipulation of the lens 1110. Lens 1110 may be moved by focusing mechanism 1109, which may comprise a screwing mechanism. The zooming assembly may include spacer 1108, which may have length (i.e. from the tissue to the lowest lens position marked as 1111) in a range of 0.05 cm to 50 cm, more preferably in the range of 0.1 cm to 35 cm, most preferably in the range of 0.15 to 10 cm. The zooming assembly may also include focusing mechanism 1109.

A handheld applicator of the present invention may include one or more sensors 1102 for gathering measurements from the surrounding environment and/or from the one or more emitters 1106. Emitters 1106 (e.g. magnet), located on scanning unit 1002, may provide information to sensor 1102 (e.g. a Hall sensor). Based on the emitted and recognized information, the central control unit may identify particular types of handheld applicators and scanning units. Methods of recognizing the type or configuration of the handheld applicator may alternatively include RFID, data communication or other methods known in the art. The central control unit may enable, disable, or adjust one or more treatment parameters according to the handheld applicator recognized and the scanning unit recognized. Also, the central control unit 1004 may limit treatment parameters according to the recognized zooming assembly included with the handheld applicator and/or scanning unit 1002. Sensors 1102 together with emitter 1106 may also ensure correct attachment of the handheld applicator 1014 with scanning unit 1002 and/or the zooming assembly. Methods of operation may therefore include any human perceptible signal and/or ceasing of treatment (for example by shutting down the energy source) when the attached handheld device or its settings are not correct.

Figure 12A:
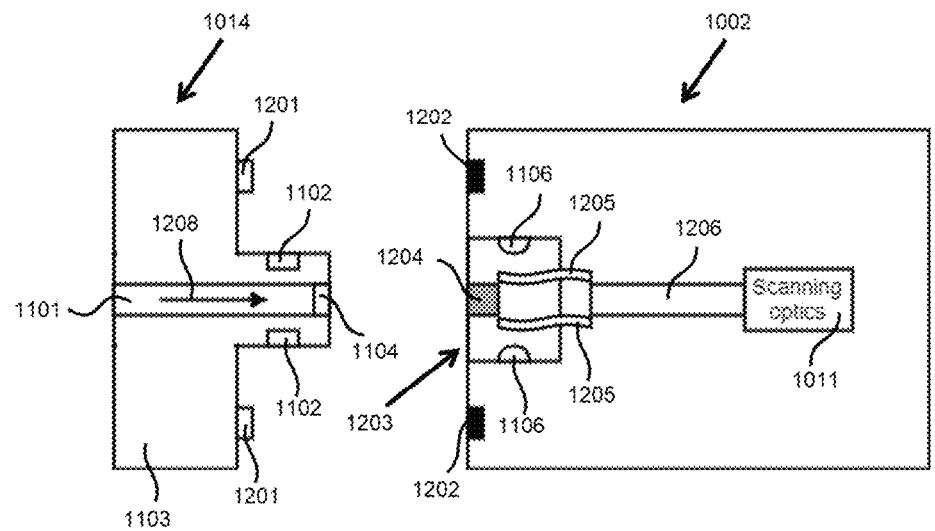
FIG. 12A is an example of a handheld applicator disconnected from a scanning unit

Handheld applicator 1014 may be connected to the scanning unit 1002 via an attaching mechanism. FIG. 12A shows handheld applicator 1014 separated from scanning unit

1002. Handheld applicator 1014 as shown includes light waveguide 1101 guiding the light (represented by arrow 1208), encased in the handheld applicator body 1103. In some embodiments, handheld applicator 1014 contains at least one pin 1201. In the exemplary embodiment, the handheld applicator includes two pins 1201. The exemplary partial view of scanning unit 1002 includes recesses 1202 for insertion of pins 1201, connector 1203, sealing element 1204, at least one movement element 1205 (e.g. a spring), scanning light waveguide 1206, and scanning optics 1011. Movement element 1205 (e.g. spring) may be placed in a dust-proof cylinder.

Figure 12B:
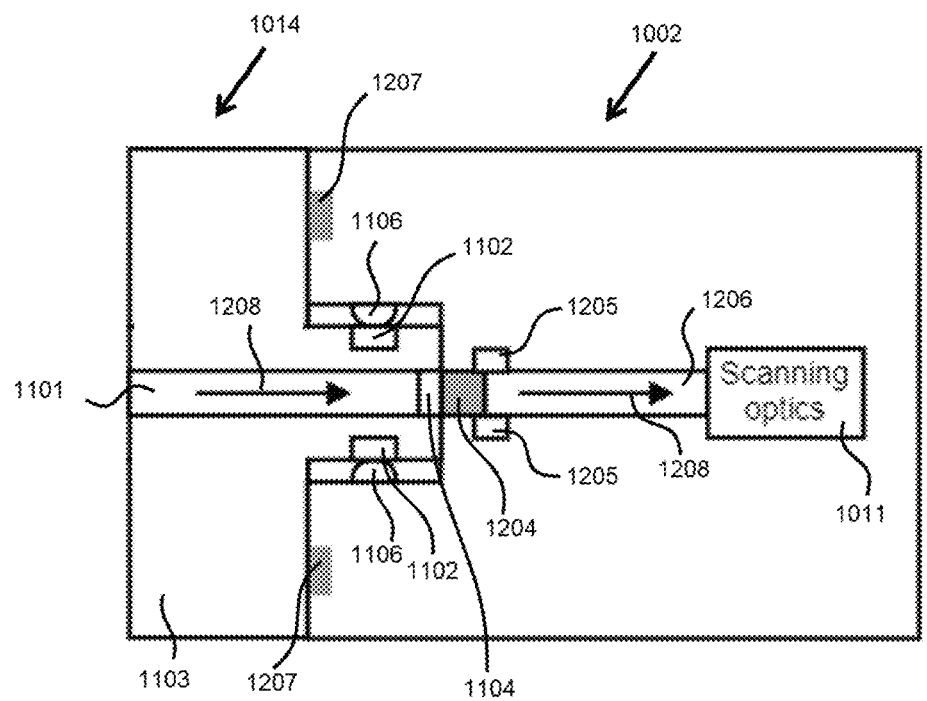
FIG. 12B is an example of a handheld applicator connected to a scanning unit

FIG. 12B shows the handheld applicator 1014 connected to the scanning unit 1002 by connector 1203. The sealing element 1204 may be moved inside the scanning unit 1002 adjacent and/or in direct contact with scanning light waveguide 1206. As a result, the sealing element 1204 is part of the newly created light wave path including light waveguide 1101, translucent element 1104, sealing element 1204 and scanning light waveguide 1206. Light 1208 may be transmitted through the newly created wave path of the scanning optics 1011. Movement of the sealing element 1204 is controlled by movement element 1205 (shown as compressed springs). Alternatively, the movement elements 1205 may move the sealing element 1204 aside from the light waveguide.

The handheld applicator is secured in the connected position shown in FIG. 12B by insertion of the pins 1201 into the recesses 1202 creating locked pins 1207. In the exemplary embodiment, handheld applicator 1014 may be rotated during the insertion into the scanning unit 1002 until the pins 1201 mate with the recesses 1202. During release, rotation of the handheld applicator in the opposite direction may loosen the locked pins 1207 and the movement elements 1205 may provide assisted release of the handheld applicator 1014 from the scanning unit 1002. Alternatively, the handheld applicator 1014 may be secured to scanning unit 1002 by other mechanisms including magnetic force, electromagnets, friction, latching or any other suitable connection method known in the art.

The sealing element 1204 may comprise for example glass, diamond, sapphire or plastic tightly positioned in the connector 1203 in the dust-proof cylinder. The sealing element 1204 may provide a dust-proof barrier to the scanning unit 1002. Because the sealing element 1204 is fixed in place when the handheld applicator 1014 and scanning unit 1002 are connected, the sealing element may prevent transfer of any contamination and/or dust into the scanning unit 1002.

Devices and methods of the present invention may provide distance control. Distance control may be used to maintain a predetermined distance between the treated tissue and scanning unit 1002 and/or handheld applicator 1014. In an exemplary embodiment, the distance may be measured by sound reflection, for example using an ultrasonic transmitter and detector placed on and scanning unit 1002 and/or handheld applicator 1014. Measured distance may be provided to the central control unit 1004, which may change one or more treatment parameters according to measured distance. The ultrasound or other distance sensor may also measure the temperature of the treated tissue, and the central control unit 1004 may change one or more treatment parameters according to the measured temperature.

Temperature of the treated tissue may be measured by a thermographic camera and/or an IR temperature sensor. The measured temperature may be communicated to the central control unit 1004, which may then change one or more treatment parameters according to measured temperature of the treated tissue. Sensors measuring temperature may measure the temperature as a relative measurement, for example as a difference between the temperature recorded at the beginning of the treatment and the temperature recorded during the treatment. The sensor may also communicate with calibration unit 1007 and provide values of the absolute temperature of the treated tissue.

A method of treatment may include treatment of one or more treatment areas using one or more treatment patterns. Treatment of the treatment area using one or more treatment patterns may be repeated more than one time. The treatment area may be defined as an area where the energy spot is moved during a treatment session, together with adjacent tissue. Treatment patterns may be defined as tissue surface paths followed by the energy spot on the treatment area during one treatment cycle.

Methods of treatment according to the present invention may include following steps: choosing of the body part to be treated; mapping the tissue surface using one or more sensors; proposing and modifying the shape and dimensions of one or more treatment areas; selection of the shape and dimensions of one or more treatment patterns; setting of threshold values of treatment parameters; setting of threshold ranges; choosing a treatment mode; transferring energy to the tissue; measuring treatment parameters and/or tissue characteristics (e.g. color, shape and/or depth); changing one or more treatment parameters or thresholds based on measured characteristics; and returning one or more elements of information as a result of the treatment.

The order of the steps may vary. In some embodiments, one or more of the steps may be omitted or repeated.

Body parts to be treated may be chosen by the patient, the operator and/or the device. The patient and/or operator may choose the body part to be treated for aesthetic or medical reasons. Devices may choose the body part to be treated according to information received from one or more sensors. For example, the ultrasound sensor may provide information about the thickness of adipose tissue, or a camera may provide information about presence of aesthetic problems (for example cellulite).

Mapping of tissue problems may be provided by camera and/or ultrasound sensor. In case of camera, a tissue problem may be recognized by comparing the colors observed in the treatment area with the colors of corresponding reference tissue. In the case of an ultrasonic sensor, tissue problems may be recognized by comparing the parameters (e.g. amplitude, frequency, period and/or reflection angle) of reflected mechanical waves from the treatment area with the parameters of reflected waves from a reference tissue area. Reference tissue areas may be an untreated tissue area chosen by the operator and/or device. Color and/or parameters of reflected mechanical waves may be measured before and/or after the mapping. The color and/or parameters of the reference tissue may be measured during the mapping by the same sensor and/or a different sensor.

In some embodiments, the shape and dimensions of the treatment area may be selected separately. Shapes may be selected from a predefined set of shapes, or shapes may be created by the operator and/or device. Additionally, shapes may be proposed by device according to the chosen body part. The shape of the treatment pattern may be created according to an image of the tissue problem captured by a camera. After selecting a shape, in some embodiments the shape may be further modified by the operator and/or the patient by dividing the shape into a plurality of segments (e.g. smaller surface partitions and/or borderlines), or by converting the to another shape. The creation of a new shape, modification of one or more dimensions, division of created shapes and/or movement of segments may be executed using the user interface 1006. Dimensions of the treatment area may be in the range of 1×1 cm to 180×180 cm and may have a total area from 1 cm2 to 32 400 cm2, 15 000 cm2, 10 000 cm2 or 2500 cm2. Dimensions of the treatment pattern may be in the range of 0.01 cm2 to 5000 cm2 or 0.1 cm2 to 2000 cm2 or 1 cm2 to 500 cm2.

Figure 13:
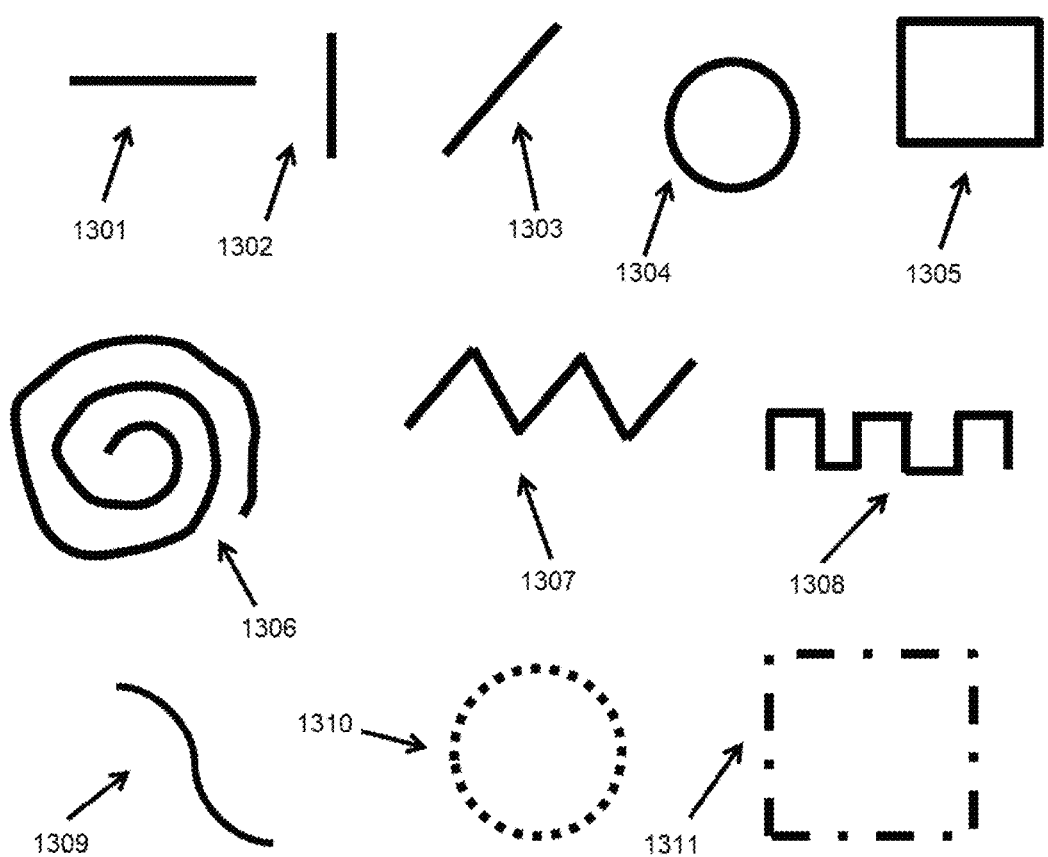
FIG. 13 shows examples of treatment patterns

Examples of treatment patterns on the tissue surface are shown in FIG. 13, and include linear horizontal 1301, linear vertical 1302, linear diagonal 1303, circular 1304, rectangular 1305, spiral 1306, zigzag 1307, tooth-like 1308 and/or S-shape 1309. Treatment patterns may be delivered in defined points and/or intervals, as shown in patterns 1310 and 1311. Alternatively, the treatment patterns may be implemented beneath the surface of the tissue.

Figure 14A:
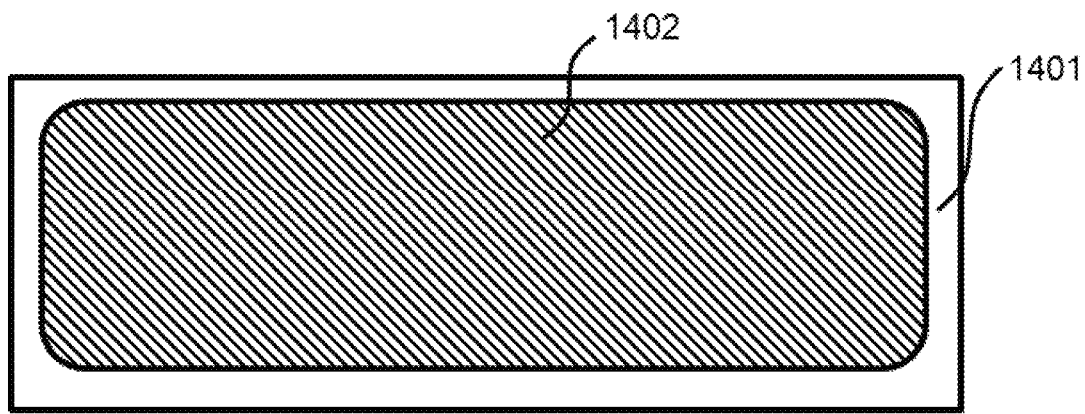
FIG. 14A is an example of a treatment area and treatment pattern
Figure 14B:
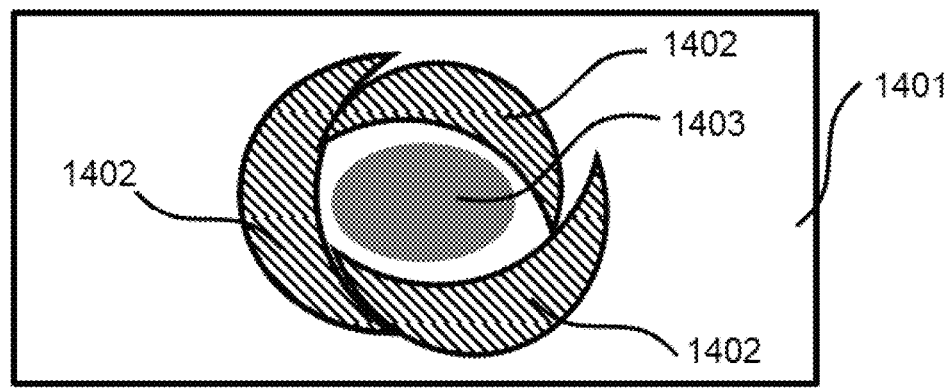
FIG. 14B is another example of a treatment area and treatment pattern

FIG. 14A shows treatment area 1401 with treatment pattern 1402. Treatment pattern 1402 is shown as a large surface pattern, which may be advantageous in areas of tissue free from any substantial unevenness. FIG. 14B shows treatment area 1401 with uneven region 1403 and three overlapping treatment patterns 1402 surrounding the uneven region 1403.

Methods of setting threshold values may include choosing one or more threshold values of one or more treatment parameters, and using those threshold values to determining values for other treatment parameters. Threshold values may include, for example, the surface temperature of the treated tissue. Other relevant threshold values include, but are not limited to, the distance between the tissue and the scanning unit or handheld applicator, the total energy output to at least part of the treated tissue area, the energy flux transferred to at least part of the treatment area, and the scanning speed of the scanning unit 1002 and/or handheld applicator 1014. Treatment methods of the present invention may include the steps of increasing one or more threshold values until the patient and/or operator stops the increase. During the increase of the threshold value, the central control unit 1004 may in some embodiments adapt at least one other treatment parameter based on the increasing threshold value. The threshold value may be set before treatment or it may be changed during treatment according to one or more parameters measured by sensor or sensors 1013 (e.g. distance and/or temperature of the treated tissue). When the one or more threshold values of treatment parameters are set, other treatment parameters may be modified by the device.

Setting of threshold ranges may include setting of one or more tolerances around a threshold value. Threshold tolerances of the present invention may be about 25%, more preferably 20%, even more preferably about 15%, most preferably 10% surrounding the threshold value. Methods of the present invention may include setting tolerances for other treatment parameters which have no set threshold value. Such tolerances may promote homogeneity of treatment.

Selection of treatment modes may include the selection of a treatment provided by scanning unit 1002 and/or manual treatment provided by handheld applicator 1014. Large, smooth treatment areas may be treated by using scanning unit 1002, while uneven treatment areas may be treated using handheld applicator 1014. Scanning unit 1002 may also be used for treatment of uneven treatment areas, because the device may include adjustment of treatment parameters according to other steps of the method. In some embodiments, it is possible to combine the use of scanning unit 1002 and handheld applicator 1014. For example, treatment pattern 1402 on FIG. 14A may be provided by scanning unit 1002, while treatment patterns 1402 on FIG. 14B may be provided by a handheld applicator 1014. The operator may use the scanning unit for treatment of large or smooth areas of the tissue, while the handheld applicator may be used for treatment of the areas not treated by the scanning unit. Switching from the handheld applicator to the more effective scanning unit by connecting the former to the latter provides the operator a versatile device for complex treatments. Both modes of treatment may be provided by one device.

Transfer of energy to the tissue may include irradiation of the tissue with light, Also, in some embodiments, a camera may provide information about the position of the energy spot on the surface of the tissue.

Measuring of treatment parameters and/or characteristics of a tissue problem may include measurements provided by one or more sensors 1013. Treatment parameters may be measured continuously or in discrete time intervals. In some embodiments, methods of the present invention include processing the measurement, for example by transmitting the measurements from the one or more sensors 1013 to the central control unit 1004. Sensor 1013 may measure a treatment parameter with a set threshold value and/or threshold range. Measurement of the tissue temperature may be done by temperature sensor and measured tissue temperature may be communicated to the central control unit 1004. Measurements of characteristics of the tissue problem may include measurement of its color, shape, depth and/or temperature on the edge of the tissue problem. Characteristics of the tissue problem may be measured using a camera and/or ultrasonic sensor similarly to methods used in mapping the color irregularity.

In response to measured values of treatment parameters, a controller of the present invention may select from a set of options including continuing treatment, providing a human perceptible signal, setting a new threshold value and/or threshold range, ceasing treatment, or adjusting one or more treatment parameters to a set threshold in order to be in the range. For example, when the temperature of the treated tissue is out of threshold temperature range, the central control unit 1004 may cease the energy transfer and/or change one or more treatment parameters (e.g. energy spot size, energy spot shape, duration of the treatment, output of the energy, direction of the movement of the energy spot and/or scanning speed) in order to bring the temperature of the treated tissue back to within tolerance of the set target value and/or within the threshold range.

In another example, the set threshold value may be the distance of the treated tissue from scanning unit or handheld applicator. Because the presence of unevenness on the treated tissue may bring the scanning unit and/or handheld applicator closer to the treated tissue, the controller may respond by adjusting the distance in order to keep the actual distance as close as possible to the set threshold value. In alternate embodiments, the controller may emit a human perceptible signal, cease the treatment and/or change one or more treatment parameters (e.g. output of the energy and/or energy spot size) in order to compensate for the change in distance. Changing one or more treatment parameters may lead to a change in a threshold value. Changing one or more treatment parameters according to the distance of the treated tissue from scanning unit or handheld applicator may be advantageous for treatment of less approachable curved parts of the body (e.g. flanks, legs and/or hips).

In still another example, two threshold values representing the temperature of the treated tissue during the treatment and distance between the tissue and scanning unit or handheld applicator may be set. When the temperature of treated tissue and the distance are different from the set threshold values (e.g. because of the tissue is uneven or the light source is non-homogenous), responses may include ceasing operation, emitting a human perceptible signal, changing one or more treatment parameters (e.g., the output of the energy, the energy spot size, the scanning speed, the direction of movement of the energy spot, the treatment pattern, the wavelength or wavelengths of the energy, the frequency and/or the energy flux) in order to bring the measured parameters of the treated tissue closer to the set threshold values and/or into the tolerance provided by threshold ranges.

Response to a measured characteristic of the tissue problem may include ceasing treatment and/or changing treatment parameters. For example, a response may include decreasing the scanning speed, changing the treatment pattern, and/or repeated movement of the energy spot over the tissue problem when the tissue problem retains the color during treatment. In another example when the energy spot is moved to a differently colored part of tissue problem (e.g. a tattoo), the wavelength of the applied light may be changed, for example to provide a different treatment to differently-colored pigment and/or ink. In still another example, a response may include changing the power output, energy spot size, wavelength of the energy and/or the distance between the tissue and the scanning unit when at least part of the tissue problem is located deeper than anticipated during initial mapping of the tissue problem. In still another example, a response may include changing the treatment pattern together with changing the wavelength of the applied light. In such cases, when the color of the already-treated tissue problem changes during and/or after the treatment, the energy spot may be repeatedly moved over the tissue problem, while the applied light has different wavelengths matching the different color of the tissue problem.

Response to changes or lack of changes in shape of the tissue problem may include ceasing treatment and/or changing one or more treatment parameters. For example, when the shape of the tissue problem changes, the treatment parameter and/or energy spot size may be changed in order to match new shape of the tissue problem. In other embodiments, the output power of the energy and/or scanning speed may be changed.

Methods of treatment may further include ceasing operation of the device and/or emitting a human perceptible signal according to the information from and ultrasound sensor and/or a gyroscope if an error occurs. Errors detected may include, but are not limited to, movement of the patient sensed by ultrasonic sensor, a change in the distance between the scanning unit and the tissue, or movement of the scanning unit itself sensed by a gyroscope or accelerometer. An ultrasonic sensor and/or a gyroscope may then provide such information to a controller. The controller may process the information and cease the operation of device and/or emit a human perceptible signal (e.g. sound, change of scanning color).

Other sensors 1013 may comprise a sensor measuring oxygenation of the blood. An oxygenation sensor may be of a contact type, or preferably a noncontact type. Examples of oxygenation sensors include, but are not limited to, a Clark electrode, an RGB camera, a spectrophotometer, or one or more CCD cameras with specific filters (e.g. 520 nm and/or 660 nm). In some embodiments, oxygenation sensors of the present invention provide information about blood flow and healing of the tissue. Oxygenation of the tissue may also be measured by a diffuse correlation spectroscopy flow-oximeter. Methods may include measurement of oxygenation of the blood in blood vessels in and/or close to the treatment area. Oxygenation of the blood may be measured in blood vessels in and/or close to the treatment pattern. Oxygenation sensors may provide information to the central control unit 1004. The central control unit 1004 may include a proportional controller which may cease the transfer of energy when the blood oxygen level drops below an oxygenation limit having a value of 98%, more preferably 96.5%, most preferably 95%. In some embodiments, the central control unit 1004 may include a PD and/or a PID controller which may adjust one or more treatment parameters. In some embodiments, when the blood oxygen level drops below a limit, possible responses include ceasing operation, decreasing and/or increasing output power, changing the wavelength of the energy and/or changing the energy generator. Power output may be decreased in order to decrease tissue temperature and/or the level of tissue damage (for example ablation or coagulation). Changes to wavelength may include changing the wavelength to one of or close to red light, which may enhance blood oxygenation. Changes of the energy generator may include changes to the energy generator (e.g. red light) which may enhance blood oxygenation. In some embodiments, the response may include changes to one or more other treatment parameters.

The scanning unit may move over the tissue and stop in one or more predefined and/or random positions. Treatment durations may be in the range of 5 seconds to 90 minutes, more preferably in the range of 10 seconds to 75 minutes, most preferably in the range of 30 seconds to 60 minutes. The distance of the scanning unit from the tissue may be in the range of 0.5 cm to 100 cm, 1 cm to 80 cm or 3 cm to 65 cm. Scanning speed, defined as the distance traversed by the scanner in a given unit of time, may be in the range of 0.01 cm/s to 150 cm/s, more preferably in the range of 0.05 cm/s to 100 cm/s, most preferably in the range of 0.1 cm/s to 80 cm/s.

Applied energy may be electromagnetic energy, e.g. gamma radiation, X-rays, UV energy, light, IR energy, radiofrequency energy and/or microwave energy. Light may be coherent, depolarized, polarized, monochromatic or polychromatic. The wavelength of the light may be in the range of 200 nm to 15000 nm, more preferably in the range of 250 nm to 10000 nm, even more preferably in the range of 300 nm to 5000 nm, most preferably in the range of 400 nm to 3000 nm.

Light may be also applied in a narrower spectral band. In some embodiments, light is applied in spectral bands representing different colors of the visible part of the electromagnetic spectrum. The wavelength of the applied light may be close to 254 nm, 405 nm, 450 nm, 532 nm, 560 nm, 575 nm, 635 nm, 660 nm, 685 nm, 808 nm, 830 nm, 880 nm, 915 nm, 970 nm, 980 nm, 10060 nm, 10064 nm, 1320 nm, 1440 nm 1470 nm, 1540 nm, 1550 nm, 1565 nm, 2940 nm, 11600 nm. Term "close to" refers to a range within 20%, more preferably 15%, most preferably 10% of the nominal wavelength. In some embodiments, light in the range of 620 to 750 nm is used for local circulation enhancement and restoration of connective tissue. Light in the range of 400 to 500 nm may be used to kill bacteria; light in the range of 560 to 600 nm may be used to stimulate tissue rejuvenation. In some embodiments, the wavelength may be changed during treatment. Methods of treatment may include application of a targeting beam of any visible (e.g. red, blue, green or violet) color.

Light may be applied in one or more beams. One beam may include light of more than one wavelength, e.g. when the light is provided by sources of different color and intensity One beam may provide an energy spot having an energy spot size defined as a surface of tissue irradiated by one beam of light. One light source may provide one or more energy spots e.g. by splitting one beam into a plurality of beams. The energy spot size may be in the range of 0.001 cm$^2$ to 600 cm$^2$, more preferably in the range of 0.005 cm$^2$ to 300 cm$^2$, most preferably in the range of 0.01 cm$^2$ to 100 cm$^2$. Energy spots of different and/or the same wavelength may be overlaid or may be separated. Two or more beams of light may be applied to the same spot in the same time or with a time gap ranging from 0.1 us to 30 seconds. Energy spots may be separated by at least 1% of their diameter, and in some embodiments energy spots closely follow each other and/or are separated by a gap ranging from 0.1 cm to 20 cm. Energy spots of the present invention may have any shape, e.g. a circular shape. In application methods using more than one energy beam, the controller may control the treatment parameters of each energy beam independently.

Light energy output may be up to 300, 250, 150 or 100 W. Light may be applied in a continuous manner or in pulses having a duration in the range of 10 µs to 5 seconds, more preferably in the range of 25 µs to 4 seconds, most preferably in the range of 40 µs to 2.5 seconds. In addition, pulses may have a duration in the range of 1 fs to 10 µs. Pulse frequency may be in the range of 0.2 Hz to 100 kHz, more preferably in the range of 0.25 Hz to 40 kHz, most preferably in the range of 0.4 Hz to 25 kHz. Energy flux provided by light may be in the range of 0.005 W·cm$^{-2}$ to 75 W√cm$^{-2}$, more preferably in the range of 0.01 W·cm$^{-2}$ to 60 W·cm$^{-2}$, and most preferably in the range of 0.01 W·cm$^{-2}$ to 50 W·cm$^{-2}$.

Applied light may be low level light. Output power may be in the range of 0.1 mW to 600 mW, more preferably in the range of 1 mW to 500 mW, even more preferably in the range of 1.5 mW to 475 mW, most preferably in the range of 3 mW to 450 mW.

Applied light may be high level light. In this case, the output of the source may be in the range of 0.1 W to 300 W, more preferably in the range of 0.2 W to 75 W, most preferably in the range of 0.35 W to 60 W.

Figure 15A:
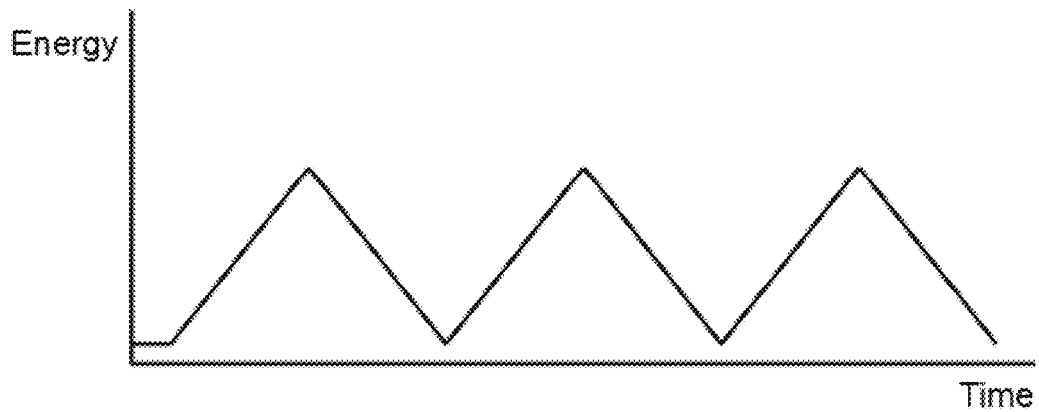
FIG. 15A is an example of energy distribution
Figure 15B:
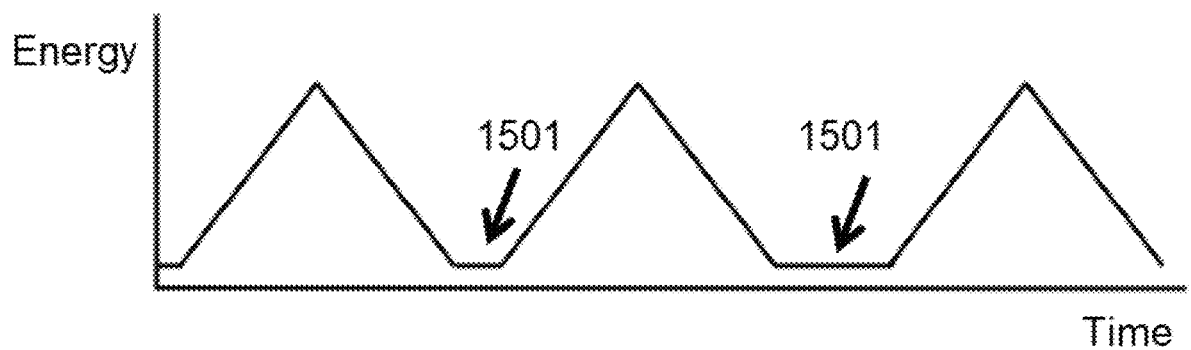
FIG. 15B is another example of energy distribution
Figure 15C:
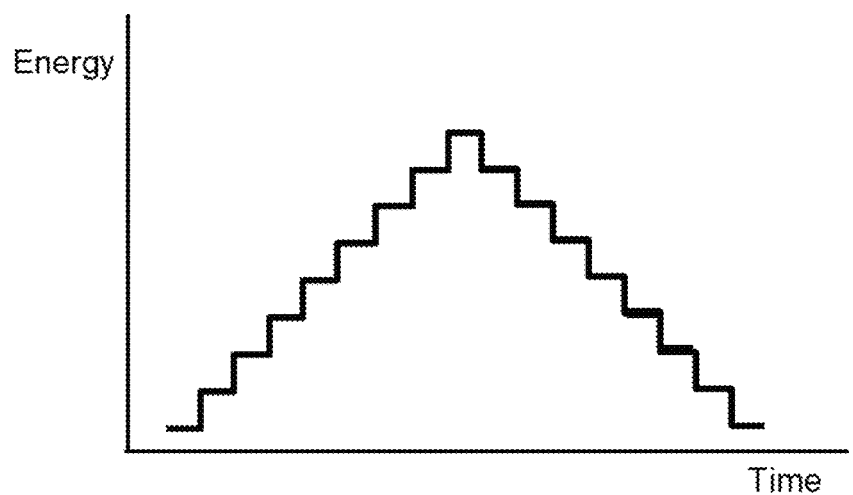
FIG. 15C is another example of energy distribution

The energy output of light over time may have triangular waveform shown in the FIGS. 15A-C. As shown on the FIG. 15A, each triangular wave may follow closely after the previous one. Alternatively, as shown in FIG. 15B, the triangular waves may be separated from one another by intervals 1501 of the same and/or different lengths. In some embodiments, the waveforms comprise multiple small steps of increasing and decreasing output, wherein the steps resemble a triangular shape, as shown on FIG. 6C.

Methods of treatment may include autonomous treatment provided by the device, including the steps of choosing the body part to be treated; mapping the tissue problem with the sensor; initializing and automatically modifying the shapes and dimensions of one or more treatment areas; selecting the shapes and dimensions of one or more treatment patterns; setting threshold values of treatment parameters; setting threshold ranges of one or more sensed parameters; choosing the treatment mode; transferring energy to the tissue; measuring the treatment parameters and/or characteristics of the tissue problems (e.g. color, shape and/or depth); and responding to measurement.

Methods of treatment may include autonomous treatment methods. When autonomous treatment is provided, almost all steps of the treatment are directed by the device. Either the operator or the patient may choose the part of the body to be treated. All other steps including initializing and automatically modifying the shape and dimensions of the one or more treatment areas, selecting the shape and dimensions of one or more treatment patterns, setting threshold values of treatment parameters, setting the threshold ranges, transferring energy to the tissue, measuring treatment parameters and/or characteristics of tissue problems, and/or responding to measurement, may be performed autonomously by the device, where the method may include correction and/or modification of the operation of the device by the device itself according to the measured information from the sensors. During the autonomous treatment methods, the adjustable arm may be operated automatically according to treatment program.

Methods of treatment may include semiautonomous treatment. When a semiautonomous treatment is provided, the device may provide autonomous treatment with possible correction and/or modification of its operation by the operator and/or patient during the treatment. The correction and/or modification of the operation may be performed according to the measured information from the sensors, the patient's needs and/or the operator's needs. During the autonomous treatment methods, the adjustable arm may be operated automatically according to corrections and/or modification provided by the operator. Method of treatment may include application of light providing a fractional treatment generating thermally damaged tissue. Thermal damage may be ablative or non-ablative (e.g. coagulation). Thermally damaged tissue may be located at least in one of the epidermis, dermis and/or hypodermis. Fractional treatment may generate thermally damaged tissue with channels, wherein channels may be opened in epidermis and reach into epidermis, dermis and/or hypodermis. Alternatively, thermally damaged tissue may be located only in one or more skin layers, but without opening channels in epidermis. Regions of thermally damaged tissue may be separated by untreated tissue.

Methods of treatment may include application of two or more wavelengths of light. Two or more wavelength may be generated by one energy generator, e.g. by differently stimulated optical fibre). Two or more wavelengths may be generated by two or more energy generators, Methods of treatment may include application of time-shifted light (e.g. a second laser). The scanning unit 1002 and/or handheld applicator 1014 may include a crystal located in the propagation path of the second laser beam, which may cause a time-shift of light propagation. The time-shifted laser light may be transmitted later than the first laser light. Therefore both lasers, particularly in pulse mode, may treat the same energy spot (i.e. the surface of the tissue irradiated by the energy spot). Such an arrangement may be used for providing improved healing and/or rejuvenation to treated tissue. Similarly, more than one energy beam may be used for removal of color irregularity, ablation of tissue and/or skin tightening. The second light with a different wavelength may provide a healing effect.

In one embodiment, a combination of first and second light may provide fractional treatment and non-ablative fractional treatment. The first light providing fractional treatment may have wavelength in the range of about 1300 nm to about 1600 nm or about 1440 nm to 1550 nm. Alternatively, the first light may have wavelength in the range of about 2700 nm to 3100 nm or about 2900 nm to 3000 nm. The second light providing wound healing stimulation may have wavelength in the range of 600 nm to 1200 nm. Alternatively, the second light may have wavelength in the range of about 1000 nm to 1200 nm. When the first light is applied before the second light, the tissue is firstly ablated and then the healing of thermally damaged tissue is stimulated. When the first light and the second light are applied simultaneously, the tissue is ablated in the same time as the healing of thermally damaged tissue is stimulated.

In another embodiment, a combination of first and second light may provide ablative fractional treatment and coagulation. The first light providing ablative fractional treatment may have wavelength in the range of about 2700 nm to about 3100 nm or about 2900 nm to 3000 nm. The second light providing coagulation may have wavelength in the range of about 1300 nm to about 1600 nm or about 1440 nm to 1550 nm. When the first light is applied before the second light, the tissue is firstly ablated and then the thermally damaged tissue or/the untreated tissue may be further coagulated to enhance the treatment effect. When the first light and the second light are applied simultaneously, the tissue is ablated and coagulated in the same time. When the second light is applied before the first light, the ablation of the tissue by the first light may last shorter time than coagulation itself, eliminating pain or inconvenience.

In another embodiment, a combination of first and second light may provide fractional treatment and pain relief. The first light providing fractional treatment may have wavelength in the range of about 1300 nm to about 1600 nm or about 1440 nm to 1550 nm. Alternatively, the first light may have wavelength in the range of about 2700 nm to 3100 nm or about 2900 nm to 3000 nm. Second light providing pain relief may have wavelength in the range of about 1000 nm to about 1200 nm or about 1040 nm to 1080 nm. When the first light is applied before the second light, the tissue is firstly ablated and then the pain of the fractional treatment is eliminated. When the first light and the second light are applied simultaneously, the tissue is ablated and the pain of the treatment is eliminated in the same time.

Figure 16A:
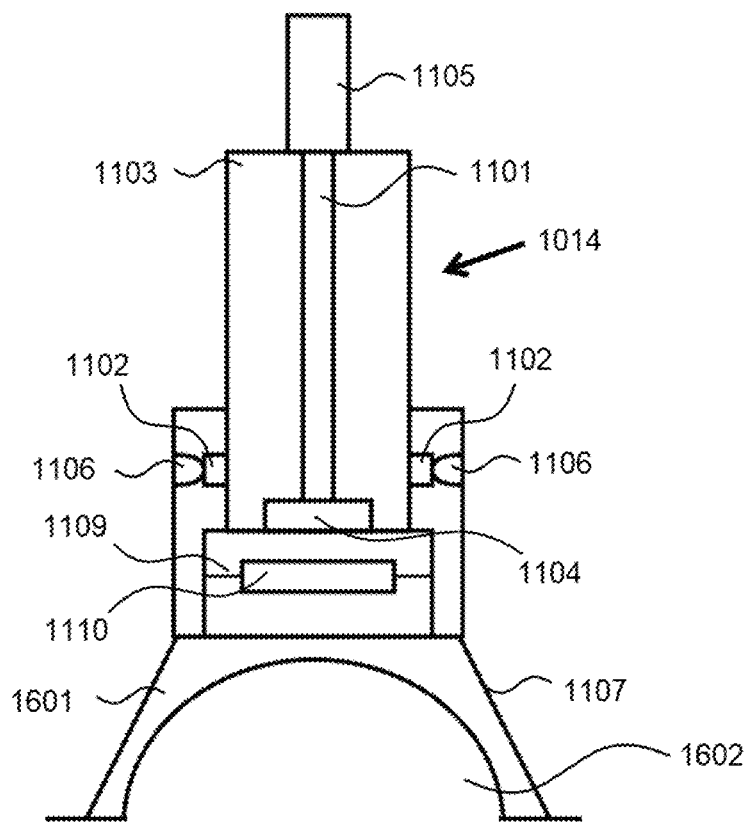
FIG. 16A is an example of device using negative pressure

Methods of treatment may also include application of a negative pressure before, during and/or after treatment by the energy. An exemplary handheld applicator capable of providing negative pressure is shown in FIG. 16A, where the handheld applicator may include one or more cavities 1601 formed by walls 1107. Walls 1107 may form a vacuum edge or vacuum cup defining magnitude of patient's skin protrusion, pressure value needed for attaching applicator to patient's body and other properties. Vacuum mask may have a circular, rectangular or other symmetrical or asymmetrical shape. The tissue 1602 may be sucked into the cavity 1601 by negative pressure generated by a source of negative pressure (not shown). Suitable sources of negative pressure include a vacuum pump located inside the device and/or external to the device but fluidly connected to cavity 1601. Negative pressure may create a skin protrusion which may move the tissue closer to the lens 1110. Negative pressure may also provide an analgesic effect. The negative pressure may be lower to room pressure in the range of 100 Pa to 2 MPa, 3000 Pa to 400 kPa, or 4000 to 100 kPa. Deflection of the tissue caused by negative pressure may be in the range of 0.2 mm to 8 mm or 0.5 mm to 60 mm or 1 mm to 50 mm or 1.5 mm to 35 mm. Pressure value under the applicator may be changed compared to pressure in the room during the treatment in range from 0.1 to 100 kPa or from 0.2 kPa to 70 kPa or from 0.5 kPa to 20 kPa or from 1 kPa to 10 kPa or from 2 kPa to 8 kPa. The negative pressure may be pulsed and/or continuous. Continuous pressure means that the pressure amplitude is continually maintained after reaching the desired negative pressure. Pulsed pressure means that the pressure amplitude varies, for example according to a pre-determined pattern, during the therapy. Use of pulsed pressure may decrease inconvenience related to negative pressure by repeating pulses of tissue protrusions at one treated site, when the energy may be applied. The duration of one pressure pulse may be in the range of 0.1 seconds to 1200 seconds, more preferably in the range of 0.1 seconds to 60 seconds, most preferably in the range of 0.1 seconds to 10 seconds wherein the pulse duration is measured between the beginnings of successive increases or decreases of negative pressure values. In case of using pulsed pressure the ratio of Ph/PI where Ph is value of highest pressure value a PI is lowest pressure value during one cycle of repeated pressure alteration may be in range from 1.1 to 30 or from 1.1 to 10 or from 1.1. to 5.

Figure 16B:
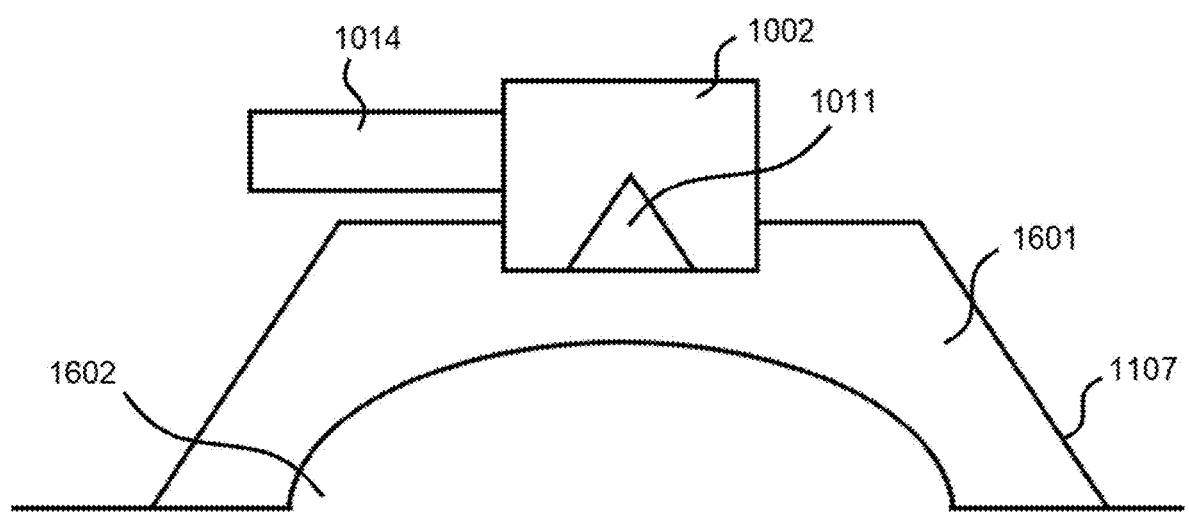
FIG. 16B is another example of device using negative pressure

An exemplary apparatus including the scanning unit 1002 is shown in FIG. 16B. Handheld applicator 1014 is connected to the scanning unit 1002 includes scanning optics 1011. Tissue 1602 is shown to be sucked into cavity 1601 formed by walls 1107. Walls 1107 may form a vacuum mask or vacuum cup defining magnitude of patient's skin protrusion, pressure value needed for attaching applicator to patient's body and other properties. Vacuum edge may have a circular, rectangular or other symmetrical or asymmetrical shape.

The scanning unit 1002, particularly the output of the scanning optics 1011 may be located inside the cavity 1601 and/or outside of the cavity 1601. When the output of the scanning optics 1011 is located inside the cavity 1601, the scanning unit may be stationary in respect to the tissue. Alternatively, the scanning unit may be mobile in respect to the tissue in all dimensional axis by coupling to manually or automatically adjustable arm. When the output of the scanning optics 1011 is outside the cavity 1601, the walls 1107 may be manufactured from transparent material allowing the transfer of the light energy.

Vacuum edge may be manufactured from dielectric material, which may be rigid, at least partly shape adaptive and/or at least partly elastic. Dielectric material from at least partly shape adaptive material may provide flexibility to adapt applicator surface to patient's surface and improve contact of the dielectric material with electrode and/or the patient body. Shape adaptive material(s) may also improve energy transfer from scanning unit and/or handheld applicator to patient's tissue.

Stiffness of the dielectric material may be in range shore A5 to shore D80 or shore A5 to shore A80 or shore A10 to shore A50 or shore A10 to shore A30. Dielectric material may be made of different polymeric characterization. Vacuum mask may cover the area in the range from 1 cm$^2$ to 32 400 cm$^2$, 15 000 cm$^2$, 10 000 cm$^2$ or 2500 cm$^2$. Vacuum mask may cover at least part or whole abdomen, love handle, thighs, arm. Vacuum mask may also cover whole torso of body.

Negative pressure or vacuum (lower air pressure than is air pressure in the room) may be used for attaching of the applicator to a certain patient's body part, may regulate contact area size of dielectric material under the treatment energy source with the patient's surface, may provide massage of the patient's soft tissue, may help to reduce creation of hot spots and edge effect, may increase body liquids circulation and/or different protrusion shapes Methods of treatment may also include application of a mechanical energy before, during and/or after treatment by the light energy. Mechanical stimulation may be represented by ultrasound energy. Ultrasound energy may provide focused and/or unfocused heating, cavitation, microbubbles formation, muscle stimulation, stimulation of healing process, blood flow stimulation and/or stimulation of inflammatory response. The frequency of the ultrasound energy may be in the range of 20 kHz to 25 GHz, more preferably in the range of 20 kHz to 1 GHz, even more preferably in the range from 50 kHz to 250 MHz, most preferably in the range of 100 kHz to 100 MHz. Energy flux provided ultrasound energy may be in the range of 0.001 W·cm$^{-2}$ to 500 W·cm$^{-2}$, more preferably in the range of 0.005 W·cm$^{-2}$ to 350 W·cm$^{-2}$, most preferably in the range of 0.05 W·cm$^{-2}$ to 250 W·cm$^{-2}$.

Mechanical stimulation may be represented by shock wave energy providing pain relief, blood flow enhancement, myorelaxation and/or mechanical stimulation. Shock wave energy may be generated by electrohydraulic, piezoelectric, electromagnetic, pneumatic and/or ballistic generator located internally or externally to the applicator. The repetition rate of shock wave energy may be in the range of 0.1 Hz to 1000 Hz, more preferably in the range of 0.1 Hz to 750 Hz, even more preferably in the range of 0.5 Hz to 600 Hz most preferably in the range of 1 Hz to 500 Hz. Energy flux provided by shock wave energy may be in the range between 0.0001 W·cm$^{-2}$ and 50 W·cm$^{-2}$, more preferably in the range between 0.0001 W·cm-2 and 35 W·cm-2, most preferably in the range between 0.0001 W·cm$^{-2}$ and 25 W·cm$^{-2}$.

In one embodiment ballistic shock waves may be used. Ballistic shock waves may be generated by striking of a projectile inside a guiding tube to a percussion guide, The projectile may be accelerated by pressurized gas, spring, electric field, magnetic field or other technique. The repetition rate of the ballistic shock wave may be in the range of 0.1 Hz to 150 Hz or 0.5 Hz to 100 Hz or 1 Hz to 60 Hz.

In another embodiment ultrasound shock waves may be used. Ultrasound shock waves may be generated by one or more piezoelements. At least onepieolement may have a volume in a range of 1.5 cm$^3$ to 160 cm$^3$ or 1.5 cm$^3$ to 60 cm$^3$ or 3.5 cm$^3$ to 35 cm$^3$ or 3.5 cm$^3$ to 20 cm$^3$. The diameter of the piezoelement may be in a range from 1 cm to 20 cm or 2 to 15 cm or 6 cm to 10 cm. The frequency of the provided ultrasound shock waves may be in a range from 1 Hz to 25 Hz or 2 Hz to 20 Hz or 2 Hz to 15 Hz or 4 Hz to 14 Hz. The duration of one ultrasound shock wave pulse may be in a range of 200 ns to 4 us to 2.5 us or 800 ns to 1.5 us. The pulse width of a ultrasound shock wave pulse positive phase may be in a range of 05 us to 3 us or 0.7 us to 2 us or 0.8 us to 1.7 us.

Methods of treatment also include application of a radiofrequency energy before, during and/or after treatment by the light energy. Radiofrequency energy may heat the adipose tissue and/or hypodermis tissue, while the light may be used for treatment of dermis and/or epidermis. Radiofrequency energy may be transmitted into the tissue without physical contact with the patient, same as light. Contactless application enables simultaneous treatments of large areas of human body. In the present contactless methods, the skin may be sufficiently cooled passively by circulating air.

Radiofrequency energy may be provided to the skin by at least one capacitive electrode generating an electromagnetic field. Electrode polarity may continuously fluctuate and induce an electromagnetic field inside tissue. Selective treating in the skin occurs due to dielectric losses. An inductive electrode may alternatively be used. The treatment system for creating the electromagnetic field can use bipolar electrodes, where electrodes alternate between active and return function and where the thermal gradient beneath electrodes is during treatment almost the same. The system may alternatively use monopolar electrodes, where the return electrode has sufficiently large area in contact with skin of patient and is typically positioned a relative larger distance from the active electrode. A unipolar electrode may also optionally be used.

The radiofrequency energy may be applied in continuous or pulse mode. Using a pulse mode of radio frequency treatment, the treatment is local and the power is typically limited to about 1000 W. With the pulse mode, a high frequency field is applied in short intervals (typically in the range of 50 μs to 500 ms) and on various pulse frequencies (typically in the range of 50 to 1500 Hz). The maximum output during the continuous method is typically limited to 400 W. The frequency of radiofrequency energy generated by (HF) generator may be in the range of 10 kHz to 300 GHz, more preferably in the range of 300 kHz to 10 GHz, most 20 preferably in the range of 400 kHz to 6 GHz. In another embodiment, the radiofrequency energy may be in the range of 100 kHz to 550 MHz, more preferably in the range of 250 kHz to 500 MHz, even more preferably in the range of 350 kHz to 100 MHz, most preferably in the range of 500 kHz to 80 MHz. The frequency of radiofrequency energy may be at 13.56 or 40.68 or 27.12 MHz or 2.45 GHz. The HF generator may include balun transformer. The HF energy generator may include or be coupled to transmatch to adjust the input impedance to the impedance of the treated tissue in order to maximize the power transfer. The temperature of treated tissue may be increased to 37-69° C., more preferably to 37-59° C., most preferably to 37-49° C. by radiofrequency energy.

An air gap or material with high air permeability may be placed between the skin and the applicator. This arrangement uses the human thermoregulatory system for cooling and avoids the need of artificial cooling of the skin. Optionally, the skin may be cooled via a stream of chilled or ambient temperature air. The human thermoregulatory system enables perspiration and other bodily fluids to evaporate and cool the surrounding skin. The application of electromagnetic waves is contactless, therefore sweat accumulation and/or hot spot creation are avoided. Cooling of the patient's skin may optionally use airflow circulation using a stream of cooled or ambient temperature air. Cooling can be provided by positioning an air moving device proximate to the skin. The air moving device may be attached to or implemented into the applicator. Air moving device may be any kind of fan, ventilator or blower. The blower may include an air tube connected to air source for moving air through the air tube to the patient's skin. The air source may alternatively be cooled to provide cooled air. Alternatively, air suction may be also used as an active cooling method.

The sum of energy flux density of the radio frequency waves and the optical waves applied to the patient during therapy, where the therapy means simultaneous, successive or overlap treatment or treatments may last up to 120 minutes, more preferably up to 60 minutes, most preferably up to 30 minutes, is in the range of 0.0025 W·cm$^{-2}$ and 120 W·cm$^{-2}$, more preferably in the range of 0.005 W·cm$^{-2}$ and 90 W·cm$^{-2}$, most preferably in the range of 0.01 W·cm$^{-1}$ and 60 W·cm$^{-2}$. The energy flux density of optical waves constitutes at least 1%, more preferably at least 3% and most preferably at least 5% of the sum of energy flux density.

Methods of treatment may include cooling of the treated and/or untreated tissue before, during and/or after the treatment by the light energy. Cooling of tissue may protect the tissue from damage of epithelial layer, overheating, burning of tissue or painful treatment. Cooling of hypodermis may provide disruption of adipose tissue. Cooling of dermis or hypodermis may also provide decrease in blood circulation contributing to slower heat dissipation of light energy.

Cooling may be provided by cooling element. Cooling element may include a coolant reservoir, an active solid cooling element and/or a cooled element. The coolant reservoir may include coolant, which may be sprayed onto and/or into tissue and/or used to cooling the cooled element. Coolant may include saline, glycerol, water, alcohol, water/alcohol mixture, cold air and/or liquid nitrogen. The temperature of the coolant may be in the range of −200° C. to 37° C. The cooled element may include thermal conductive material e.g. glass, gel, ice slurry and/or metal. The active solid cooling element may include an Peltier element including active side cooling the tissue and passive side which may be cooled by liquid (e.g. water), gas coolant (e.g. air), coolant and/or another Peltier element. The temperature of the cooling element during the active treatment may be in the range of −80° C. to 37° C. or −70° C. to 37° C. or −60° C. to 35° C. The temperature of the tissue may be decreased under the 37° C. The temperature of the tissue may be decreased in the range of −30° C. to 35° C. The tissue may stay cooled for time interval of at least 1, 5, 30 or 60 minutes.

In one embodiment, the temperature of treated adipose tissue during one cooling cycle may be in the range of −10° C. to 37° C. or −5° C. to 20° C. or −3° C. to 15° C. while the temperature of dermis and/or epidermis is maintained in the temperature range of −5° C. to 15° or around the temperature of about 0° C. In another embodiment, the temperature of treated collagen tissue during one cooling cycle may be in the range of −80° C. to 37° C. or −75° C. to 20° C. or −70° C. to 15° C. while the temperature of dermis and/or epidermis is maintained in the temperature range of −5° C. to 15° or around the temperature of about 0° C. The foregoing description of preferred embodiments has been presented for purposes of illustration and description. It is not intended to be exhaustive or to limit the invention to the precise form disclosed. Modification and variations are possible in light of the above teachings or may be acquired from practice of the invention. All mentioned embodiments may be combined. The embodiments described explain the principles of the invention and its practical application to enable one skilled in the art to utilize the invention. Various modifications as are suited to a particular use are contemplated. It is intended that the scope of the invention be defined by the claims appended hereto and their equivalents.

What is claimed is:

1. A device for a soft tissue treatment of a patient, comprising:
   an applicator comprising an electrode,
   wherein the electrode is configured to provide both a radiofrequency energy and a pulsed electric current to a face of the patient;
   a fastening mechanism configured to fix the applicator to the face; and
   a control unit comprising a microprocessor configured to control the radiofrequency energy and the pulsed electric current,
   wherein the radiofrequency energy has a frequency in a range of 0.1 MHz to 25 GHz and causes a heating of soft tissue of the face,
   wherein the pulsed electric current is provided within a series of envelopes, wherein the envelopes repeat with a frequency in a range of 0.1 Hz to 140 Hz, and
   wherein the pulsed electric current causes contraction of a muscle within the face.

2. The device of claim 1, wherein the radiofrequency energy is provided in pulses with a pulse duration in a range of 50 μs to 100 s.

3. The device of claim 2, wherein the frequency of the radiofrequency energy is in a range of 500 kHz to 80 MHz.

4. The device of claim 3, wherein the pulsed electric current has a pulse frequency in a range of 0.1 Hz to 200 Hz.

5. The device of claim 4, wherein the fastening mechanism comprises a belt configured to attach the applicator in contact with the face of the patient.

6. The device of claim 5, further comprising a temperature control system, wherein the temperature control system is configured to control the radiofrequency energy applied such that a temperature of an epidermis of the face of the patient is maintained in a range of 37° C. to 50° C.

7. The device of claim 6, wherein the electrode is configured to apply the radiofrequency energy and the pulsed electric current to the soft tissue of the face sequentially.

8. The device of claim 7, wherein the temperature control system comprises at least one sensor configured to monitor one of a temperature of the soft tissue, a temperature of any part of the applicator, an impedance of the face, or a conductivity of the face.

9. The device of claim 8, wherein the control unit is configured to automatically change at least one of a frequency, an output power, or a pulse duration of at least one of the radiofrequency energy or the pulsed electric current based on information from the at least one sensor.

10. A method of a soft tissue treatment of a patient comprising:
    placing an applicator to a surface of a face of the patient, the applicator comprising an electrode;
    fixing the applicator in contact with the face by a fastening mechanism;
    applying a radiofrequency energy with a frequency in a range of 0.1 MHz to 25 GHz provided by the electrode to a treatment area of the face and causing a heating of soft tissue within the treatment area;
    applying an electrotherapy to the treatment area by a pulsed electric current provided by the electrode and causing contraction of a muscle within the treatment area, wherein the pulsed electric current is provided within a series of envelopes, and wherein the envelopes repeat with a frequency in a range of 0.1 Hz to 140 Hz; and
    controlling the heating of the soft tissue by the radiofrequency energy and parameters of the envelope of the pulsed electric current provided by the electrode.

11. The method of claim 10, wherein the treatment area is in a range of 1 cm$^2$ to 500 cm$^2$.

12. The method of claim 10, further comprising applying the electrotherapy after the radiofrequency energy.

13. The method of claim 10, further comprising providing the radiofrequency energy in pulses with an energy flux density on a surface of the electrode in a range of 0.01 mW·mm$^{-2}$ to 10 W·mm$^{-2}$.

14. The method of claim 10, wherein the pulsed electric current comprises series of rectangular shaped pulses.

15. The method of claim 10, wherein the fastening mechanism comprises a belt.

16. The method of claim 15, further comprising applying a gel to the treatment area to improve a transfer of the radiofrequency energy or the pulsed electric current.

17. A device for a treatment of a face of a patient comprising:
- an applicator comprising an array of electrodes;
- a fastening mechanism configured to fix the applicator to the face of the patient;
- a control unit comprising a microprocessor configured to control the array of electrodes;
- a radiofrequency electrode from the array of electrodes configured to provide a radiofrequency energy with a frequency in a range of 100 kHz to 100 MHz to cause a heating of soft tissue of a treatment area of the face, wherein the radiofrequency energy is provided in pulses with a pulse duration in a range of 50 µs to 100 s; and
- an electrotherapy electrode from the array of electrodes configured to provide a pulsed electric current with a pulse frequency in a range of 0.1 Hz to 200 Hz to cause contraction of a muscle within the treatment area of the face,
- wherein the control unit is configured to provide one or more predefined treatment protocols for selection by an operator via a user interface,
- wherein the predefined treatment protocol comprises an envelope of the pulsed electric current,
  - wherein the pulsed electric current is modulated in an amplitude or a frequency within the envelope, and
  - wherein a shape of the envelope is formed by a modulation of the amplitude of consecutive pulses of the pulsed electric current contained in the envelope, and
- wherein the control unit is configured to switch on and off at least one of the radiofrequency electrode or the electrotherapy electrode from the array of electrodes based on a treatment pattern of a selected treatment protocol from the one or more predefined treatment protocols.

18. The device of claim 17, wherein successive envelopes repeat in a frequency in a range of 0.1 to 140 Hz.

19. A method of a treatment of a body part of a patient comprising:
- placing an applicator on a surface of the body part, the applicator comprising a plurality of electrodes;
- fixing the applicator in contact with the body part by a fastening mechanism;
- selecting one or more predefined treatment protocols by an operator of the device via a user interface, wherein each treatment protocol comprises a treatment pattern including providing a radiofrequency energy and a pulsed electric current;
- applying, in accordance with one of the selected treatment protocols, the radiofrequency energy to soft tissue of the body part by a radiofrequency electrode from the plurality of electrodes to cause a heating of the soft tissue,
  - wherein the radiofrequency energy is modulated in an amplitude or a frequency to establish a radiofrequency envelope;
- applying, in accordance with one of the selected treatment protocols, the pulsed electric current to the soft tissue of the body part by an electrotherapy electrode from the plurality of electrodes to cause contraction of a muscle within the body part,
  - wherein the pulsed electric current is provided within a series of envelopes modulated in an amplitude or a frequency; and
- switching between on and off states of the radiofrequency electrode and the electrotherapy electrode according to the treatment pattern of the selected treatment protocol.

20. The method of claim 19, wherein the pulsed electric current has a pulse frequency in a range of 0 Hz to 12 kHz.

21. The method of claim 20, wherein the soft tissue comprises one of skin, fat, connective tissue, nervous tissue, or muscle.

22. The method of claim 21, wherein the body part is at least one of a face or a neck.

23. A device for a treatment of a face of a patient, comprising:
- an applicator comprising an array of electrodes;
- a fastening mechanism configured to fix the applicator to the face of the patient;
- a control unit comprising a microprocessor configured to control the array of electrodes in groups;
- a radiofrequency electrode from the array of electrodes configured to provide a radiofrequency energy with a frequency in a range of 100 kHz to 100 MHz and an energy flux density on a surface of the radiofrequency electrode in a range of 0.01 mW·mm$^{-2}$ to 500 mW·mm$^{-2}$ to cause a heating of soft tissue of a treatment area of the face; and
- an electrotherapy electrode from the array of electrodes configured to provide a pulsed electric current with a pulse frequency in a range of 0.1 Hz to 200 Hz to cause contraction of a muscle within the treatment area of the face,
- wherein the control unit is configured to provide one or more predefined treatment protocols for selection by an operator via a user interface, and
- wherein the control unit is configured to switch on and off at least one of the radiofrequency electrode or the electrotherapy electrode from the array of electrodes based on a treatment pattern of a selected treatment protocol from the one or more predefined treatment protocols.

24. A device for a treatment of a face of a patient, comprising:
- an applicator comprising an array of electrodes;
- a fastening mechanism configured to fix the applicator to the face of the patient;
- a control unit comprising a microprocessor configured to control the array of electrodes in groups;
- a radiofrequency electrode from the array of electrodes configured to provide a radiofrequency energy with a frequency in a range of 100 kHz to 100 MHz to cause a heating of soft tissue of a treatment area of the face; and
- an electrotherapy electrode from the array of electrodes configured to provide a pulsed electric current with a pulse frequency in a range of 0.1 Hz to 200 Hz to cause contraction of a muscle within the treatment area of the face,
- wherein the control unit is configured to provide one or more predefined treatment protocols for selection by an operator via a user interface,
- wherein the control unit is configured to switch on and off the at least one radiofrequency electrode or the electrotherapy electrode from the array of electrodes based on a treatment pattern of a selected treatment protocol from the one or more predefined treatment protocols, and
- wherein the one or more predefined treatment protocols are configured to provide the pulsed electric current after the heating by the radiofrequency energy.

* * * * *

UNITED STATES PATENT AND TRADEMARK OFFICE
CERTIFICATE OF CORRECTION

| | |
|---|---|
| PATENT NO. | : 11,602,629 B2 |
| APPLICATION NO. | : 17/671273 |
| DATED | : March 14, 2023 |
| INVENTOR(S) | : Schwarz et al. |

It is certified that error appears in the above-identified patent and that said Letters Patent is hereby corrected as shown below:

In the Claims

In Column 64, Claim 10, Line 29, delete "patient" and insert -- patient, --, therefor.

In Column 64, Claim 10, Line 47, delete "envelope" and insert -- envelopes --, therefor.

In Column 65, Claim 17, Line 1, delete "patient" and insert -- patient, --, therefor.

In Column 65, Claim 19, Line 37, delete "patient" and insert -- patient, --, therefor.

Signed and Sealed this
Second Day of May, 2023

Katherine Kelly Vidal
*Director of the United States Patent and Trademark Office*